(12) United States Patent
Kerns et al.

(10) Patent No.: US 10,981,875 B2
(45) Date of Patent: Apr. 20, 2021

(54) QUINOLONE-BASED COMPOUNDS WITH ANTICANCER ACTIVITY

(71) Applicants: Regents of the University of Minnesota, Minneapolis, MN (US); University of Iowa Research Foundation, Iowa City, IA (US)

(72) Inventors: Robert J. Kerns, Iowa City, IA (US); Tyrell Towle, Denver, CO (US); Hiroshi Hiasa, Minneapolis, MN (US)

(73) Assignees: Regents of the University of Minnesota, Minneapolis, MN (US); University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 16/467,929

(22) PCT Filed: Dec. 8, 2017

(86) PCT No.: PCT/US2017/065448
§ 371 (c)(1),
(2) Date: Jun. 7, 2019

(87) PCT Pub. No.: WO2018/107112
PCT Pub. Date: Jun. 14, 2018

(65) Prior Publication Data
US 2020/0071273 A1    Mar. 5, 2020

Related U.S. Application Data

(60) Provisional application No. 62/432,430, filed on Dec. 9, 2016.

(51) Int. Cl.
| | |
|---|---|
| *C07D 215/56* | (2006.01) |
| *C07D 413/14* | (2006.01) |
| *C07D 471/04* | (2006.01) |
| *C07D 401/04* | (2006.01) |
| *C07D 401/14* | (2006.01) |
| *A61P 35/00* | (2006.01) |

(52) U.S. Cl.
CPC ......... *C07D 215/56* (2013.01); *C07D 413/14* (2013.01); *C07D 471/04* (2013.01)

(58) Field of Classification Search
CPC .. C07D 215/56; C07D 471/04; C07D 413/14; C07D 401/04; C07D 401/14
See application file for complete search history.

(56) References Cited

U.S. PATENT DOCUMENTS

| | | | |
|---|---|---|---|
| 6,136,823 A | 10/2000 | Sakae et al. | |
| 2003/0232818 A1 | 12/2003 | Anderson et al. | |

FOREIGN PATENT DOCUMENTS

| | | | | |
|---|---|---|---|---|
| CN | 103183676 B | * | 4/2015 | |
| WO | WO-2007106537 A2 | * | 9/2007 | ........... C07D 498/06 |
| WO | WO-2018107112 | | 6/2018 | |

OTHER PUBLICATIONS

Baraldi, P., "Pyrazolo [4, 3-e] 1, 2, 4-triazolo [1, 5-c] pyrimidine derivatives: A new pharmacological tool for the characterization of the human A3 adenosine receptor." Drug development research 52.1-2 (2001): 406-415.*
Nandi, S., "Activity Prediction of Some Nontested Anticancer Compounds Using Ga-Based PLS Regression Models." Chemical biology & drug design 78.4 (2011): 587-595.*
Tse-Dinh, Y-C., "Bacterial topoisomerase I as a target for discovery of antibacterial compounds." Nucleic acids research 37.3 (2009): 731-737.*
Kathiravan, M.K., "Topoisomerase as target for antibacterial and anticancer drug discovery." Journal of enzyme inhibition and medicinal chemistry 28.3 (2013): 419-435.*
Lim, C., "Benzo [b] thiophene-2-carboxamide derivatives as potent urotensin-II receptor antagonists." Bioorganic & medicinal chemistry letters 26.19 (2016): 4684-4686.*
"Acrolein", Pubmed Compound Summary for 7847, U.S. National Library of Medicine, (Sep. 16, 2004), 1-10.
"Formaldehyde", Pubmed Compound Summary for 712, U.S. National Library of Medicine, (Sep. 16, 2004), 1-10.
"International Application Serial No. PCT/US2017/065448, International Search Report dated Apr. 16, 2018", 5 pgs.
"International Application Serial No. PCT/US2017/065448, Invitation to Pay Add'l Fees and Partial Search Rpt dated Feb. 13, 2018", 3 pgs.
"International Application Serial No. PCT/US2017/065448, Written Opinion dated Apr. 16, 2018", 6 pgs.
"N-Formylformamide", Pubmed Compound Summary for 28961, U.S. National Library of Medicine, (Jul. 19, 2005), 1-17.
"SCHEMBL7672985", Pubmed Compound Summary for 88183736, U.S. National Library of Medicine, (Feb. 12, 2015), 1-11.
Abdel-Aziz, et al., "Novel N-4-piperazinyl-ciprofloxacin-chalcone hybrids: Synthesis, physicochemical properties, anticancer and topoisomerase I and II inhibitory activity", European Journal of Medicinal Chemistry, vol. 69, (Sep. 12, 2013), 427-438.
Delgado, Justine L., et al., "Probing structural requirements for human topoisomerase I inhibition by a novel N1-Biphenyl fluoroquinolone", European Journal of Medicinal Chemistry, 172 (2019) 109-130, (2019), 109-130.
Kathiravan, et al., "Topoisomerase as target for antibacterial and anticancer drug discovery", Journal of Enzyme Inhibition and Medicinal Chemistry, vol. 28, (Mar. 1, 2012), 419-435.
Lentz, Sarah R.C., et al., "A novel N1-biphenyl fluoroquinolone with anti-proliferative activity prevents human topoisomerase I from bindingto DNA", Center for Biocatalysis and Bioprocessing and of the NIH-sponsored Predoctoral Training Program in Biotechnology (GM008365)., 1-17.

(Continued)

*Primary Examiner* — John M Mauro
(74) *Attorney, Agent, or Firm* — Schwegman Lundberg & Woessner, P.A.

(57) ABSTRACT

Embodiments are directed to compounds of the formulae (I), (Ia), (Ib), (II), (IIa) (III), (IV), (V), and (VI); methods for treating cancer with one or more compounds of the formulae (I), (Ia), (Ib), (II), (IIa); (III), (IV), (V), and (VI); and methods for inhibiting a human topoisomerase with one or more compounds of the formulae (I), (Ia), (Ib), (II), (IIa); (III), (IV), (V), and (VI).

20 Claims, 1 Drawing Sheet

(56) References Cited

OTHER PUBLICATIONS

Oppegard, Lisa M., et al., "Novel N-1 substituted fluoroquinolones inhibit human topoisomerase I activity and exhibit anti-proliferative activity", Invest New Drugs (2019) 37:378-383, (2019), 378-383.

Towle, Tyrell R., et al., "Design, synthesis, and evaluation of novelN-1 fluoroquinolone derivatives: Probing forbindingcontact with the active site tyrosine of gyrase", Bioorganic & Medicinal Chemistry Letters 28 (2018) 1903-1910, (2018), 1903-1910.

International Application Serial No. PCT/US2017/065448 International Prelirrlinary Report on Patentability dated Jun. 20, 2019, 8 pgs.

* cited by examiner

QUINOLONE-BASED COMPOUNDS WITH ANTICANCER ACTIVITY

CROSS-REFERENCE TO RELATED APPLICATIONS

This application is a U.S. national stage application filed under 35 U.S.C. 371 from International Application Serial No. PCT/US2017/065448, filed on Dec. 9, 2016, and published as WO 2018/107112 on Jun. 14, 2018 which application claims the benefit from U.S. Provisional Appl. Ser. No. 62/432,430, filed Dec. 9, 2016, the entirety of which application is incorporated by reference as if fully set forth herein.

STATEMENT OF GOVERNMENT SUPPORT

This invention was made with government support under grants R01 AI087671 and TR000114 awarded by the National Institutes of Health. The government has certain rights in the invention.

BACKGROUND

Topoisomerases are proven therapeutic targets of anticancer drugs. A number of topoisomerase inhibitors have been developed but clinically successful topoisomerase inhibitors, such as etoposide, doxorubicin, and irinotecan, target a covalent topoisomerase-DNA catalytic intermediate and generate DNA breaks. This unique mechanism of cell killing, which is often referred as to "topoisomerase poisoning," is also the cause of therapy-related acute myeloid leukemia that develops after treatment with topoisomerase II inhibitors. Thus, there is an unmet need to explore new small molecules that inhibit topoisomerases through different mechanisms to develop novel anticancer agents with better safety profiles.

BRIEF DESCRIPTION OF THE FIGURES

The drawings illustrate generally, by way of example, but not by way of limitation, various embodiments discussed herein.

DESCRIPTION

Figure 1:
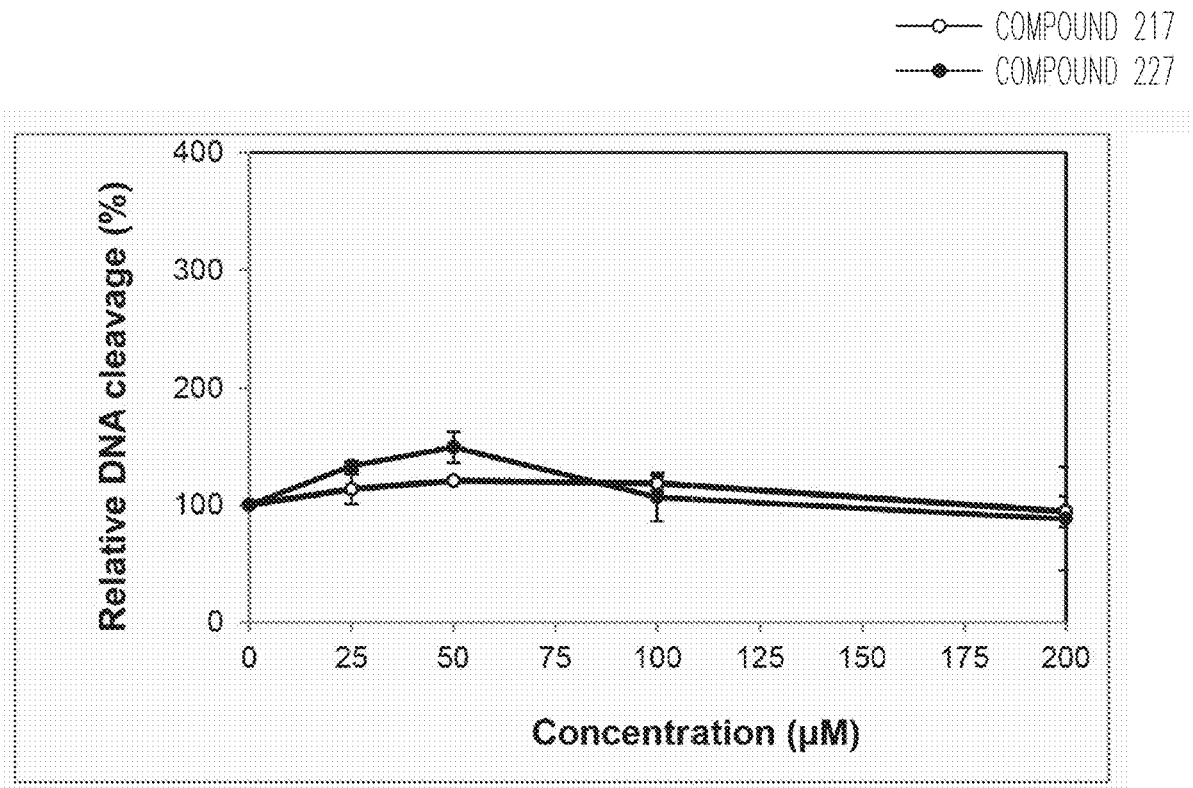
FIG. 1 is a plot of the relative DNA cleavage (%) as a function of the concentration of the compounds "217" and "227."

While the disclosed subject matter will be described in conjunction with the enumerated claims, it will be understood that the exemplified subject matter is not intended to limit the claims to the disclosed subject matter.

The inventors recently discovered that two fluoroquinolones, UITT-III-217 (217) and UITT-III-227 (227):

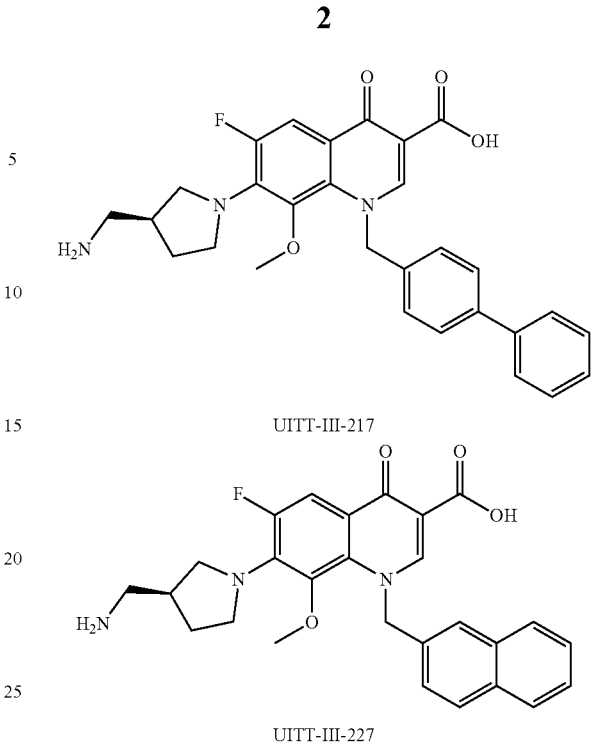

can inhibit human topoisomerase II without generating DNA double-strand breaks. Unexpectedly, these, and other compounds described herein, are active against human topoisomerase I and can be more active against human topoisomerase I than human topoisomerase II. The compounds of the various embodiments described herein are therefore new chemical entities that act through a mechanism different from topoisomerase poisons. This novel mechanism suggests that structural requirements of fluoroquinolones are not essential for the anticancer activity of the compounds of the various embodiments described herein, and allows the utilization of larger variations in the chemical structures of the compounds, to design further analogs.

Based on the abilities of compounds such as 217 and 227 to intercalate into DNA, and the lack of structural similarities between topoisomerase I and topoisomerase II, it is likely that the compounds of the various embodiments described herein intercalate into DNA, or otherwise bind DNA by some other mechanism (e.g., a combination of intercalation and minor groove binding), and inhibit the catalytic activities of topoisomerase I and topoisomerase II. For example, the National Cancer Institute's (NCI) 60 Developmental Therapeutics Program (DTP) Human Tumor Cell Line Screen demonstrated significant growth inhibition for 217 and 227 (the mean $GI_{50}$ value of 217 and 227 to be 1.9 µM and 3.1 µM, respectively) against the 60 cancer cell lines used in the screen, with the strongest growth inhibition seen in leukemia and colon cancer panels. An in vivo toxicity study showed that the intraperitoneal administration of 217 and 227 at up to 30 mg/kg for 3 weeks was well-tolerated and did not have any significant effect on animal weight gain. A proof of concept in vivo efficacy study showed that 217 inhibited the proliferation of colon cancer in vivo as well as fluorouracil (5-FU), a standard of care treatment for colon cancer. Compound 227 exhibited activity but was not as effective as 217 in this xenograft model. These results suggest that 217 and 227, and other compounds of the various embodiments described herein, might serve as lead compounds for the successful development of novel anticancer agents against colon cancer and potentially other cancers.

Because the compounds of the various embodiments described herein do not generate DNA double-strand breaks that lead to the development of therapy-related acute myeloid leukemia, the compounds will have a better safety profile. Furthermore, because their mechanisms are different from currently-available topoisomerase-targeting anticancer drugs, the compounds of the various embodiments described herein may be effective against etoposide- and other drug-resistant cancers.

Various embodiments are directed to a compound of the formula (I):

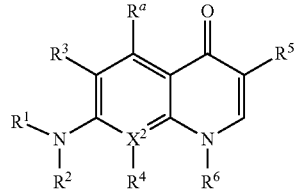

or a pharmaceutically acceptable salt, polymorph, prodrug, solvate or clathrate thereof, wherein:

$R^a$ is halo, nitro, cyano, optionally substituted alkyl, optionally substituted alkoxy, optionally substituted aryl, optionally substituted aryloxy, optionally substituted heteroaryl, or $NR^{a'}R^{a''}$, wherein $R^{a'}$ and $R^{a''}$ are each, independently, H or optionally substituted alkyl;

$R^1$ and $R^2$ are each independently H, optionally substituted alkyl, optionally substituted aryl, optionally substituted arylalkyl or $R^1$ and $R^2$, together with the nitrogen atom to which they are attached, form an optionally substituted heterocyclyl group;

$R^3$ is H or halo;

$R^4$ is H, halo, optionally substituted alkyl or optionally substituted alkoxy, but $R^4$ is absent if $X^2$ is N;

$X^2$ is N or C;

$R^5$ is H, OH, optionally substituted alkoxy, $—C(O)R^{5'}$ (wherein $R^{5'}$ is H, OH, optionally substituted alkyl, optionally substituted aryl, optionally substituted alkoxy or $—N(R^{5''})_2$, wherein each $R^{5''}$ is, independently, H, OH, optionally substituted alkoxy, optionally substituted alkyl or optionally substituted arylalkyl) or $—N(R^{5''})_2$; and $R^6$ is the group -L-$R^{6'}$, wherein L is a linker group and $R^{6'}$ is a group having sufficient "steric bulk" such that the compound of the formula (I) is (a) not a topoisomerase II poison, (b) inhibits topoisomerase I and topoisomerase II and/or (c) inhibits topoisomerase I to a greater extent than topoisomerase II. The group $R^6$ has all the features (a)-(c). $X^2$ can be C and $R^4$ is therefore present. $R^{6'}$ can be a group comprising at least two aryl groups (including fused groups), an aryl group and a heterocyclyl group (including fused groups) or two heterocyclyl groups (including fused groups), each of which can be optionally substituted with one or more substituents described herein. Non-limiting examples of aryl and heterocyclyl groups, including fused groups, are provided herein. They include, for example, biphenyl groups, naphthyl groups, and quinolinyl groups, each of which can be optionally substituted with one or more substituents described herein. Other suitable $R^6$ groups include the groups:

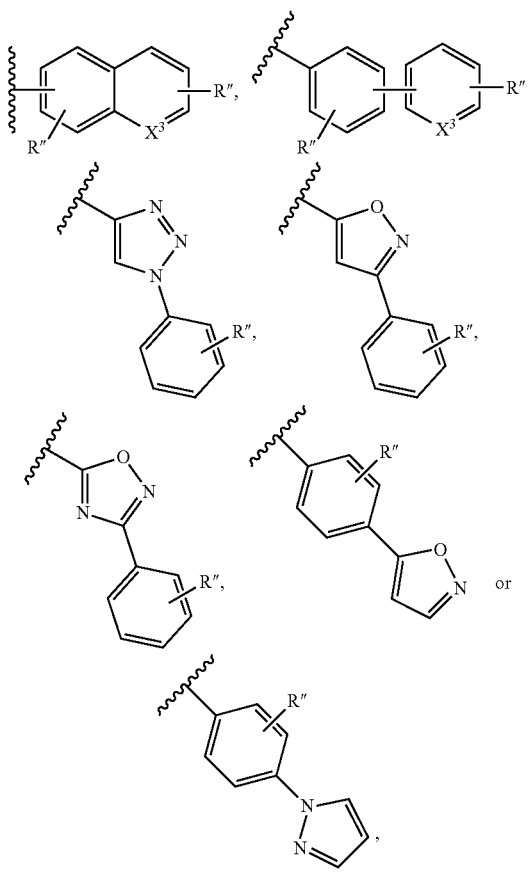

wherein each R" is, independently H or halo and $X^3$ is N or CH.

Non-limiting examples of suitable divalent linkers, -L-, include acyl groups (e.g., $—C(O)—$); hydrocarbylene groups, such as $(C_1-C_{22})$hydrocarbylene groups; hydrocarbyleneacyl groups, such as $(C_2-C_{22})$hydrocarbyleneacyl groups; and the like. Examples of $(C_1-C_{22})$hydrocarbylene groups include divalent aryl, alkyl, and cycloalkyl groups, each of which can be optionally substituted with one or more substituents described herein.

Examples of groups that can be formed by $R^1$ and $R^2$ include the groups:

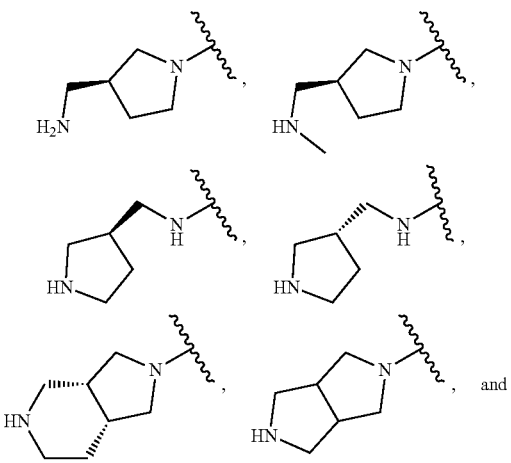

and

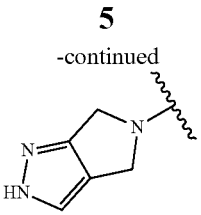

each of which can be optionally substituted with one or more substituents described herein.

Various other embodiments are directed to a compound of the formula (Ia):

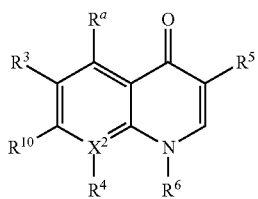

(Ia)

or a pharmaceutically acceptable salt, polymorph, prodrug, solvate or clathrate thereof, wherein:

$X^2$, $R^a$, $R^3$, $R^4$, $R^5$, and $R^6$ are as defined for compounds of the formula (I); and $R^{10}$ is aryl,

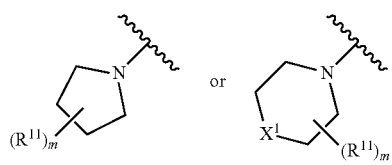

wherein each $R^{11}$ is H, —N($R^{5''}$)$_2$ (wherein $R^{5''}$ is defined herein), C(O)N(R)$_2$ (wherein each R group is, independently, hydrogen, alkyl, acyl, cycloalkyl, aryl, aralkyl, heterocyclyl, heteroaryl, or heteroarylalkyl), optionally substituted alkyl or two adjacent $R^{11}$ groups, together with the atoms to which they are attached form an optionally substituted cycloalkyl group or an optionally substituted heterocylcyl group; m is an integer from 1 to 3; and $X^1$ is O or $NR^{12}$, wherein $R^{12}$ is H or optionally substituted alkyl or $R^{12}$ and an adjacent $R^{11}$ group, together with the atoms to which they are attached, form an optionally substituted heterocyclyl group. $X^2$ can be C and $R^4$ is therefore present.

Examples of $R^{10}$ groups include the groups:

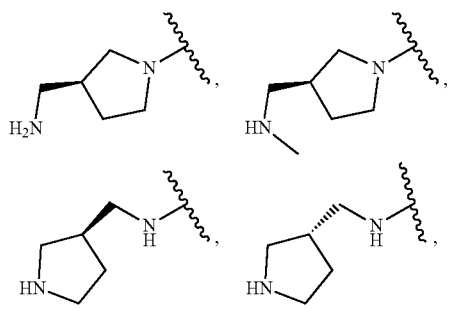

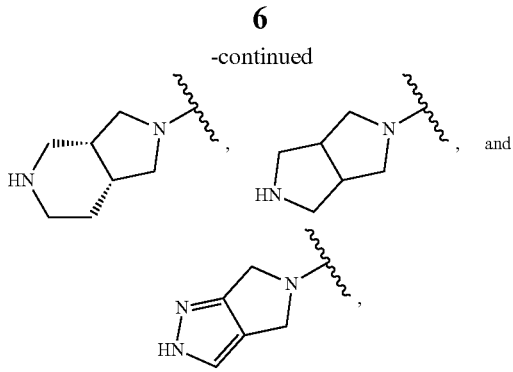

each of which can be optionally substituted with one or more substituents described herein.

Various other embodiments are directed to a compound of the formula (Ib):

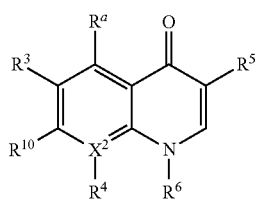

(Ib)

or a pharmaceutically acceptable salt, polymorph, prodrug, solvate or clathrate thereof, wherein:

$R^a$ is optionally substituted alkyl or $NH_2$;

$X^2$, $R^3$, $R^4$, and $R^5$ are as defined for compounds of the formula (I) and (Ia);

$R^6$ is —(CH$_2$)$_n$—$R^{6''}$ or —C(O)$R^{6''}$ wherein n is an integer from 1 to 3 (e.g., 1) and $R^{6''}$ is an aryl or heteroaryl group. Examples of aryl and heteroaryl groups represented by $R^{6''}$ include:

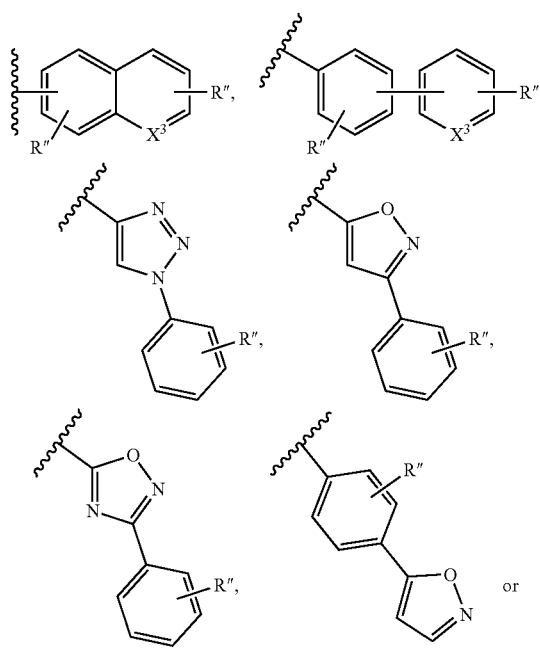

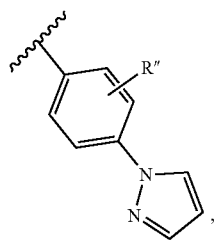

wherein each R'' is, independently H or halo and $X^3$ is N or CH; and $R^{10}$ is aryl,

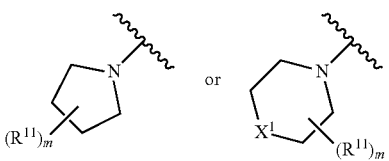

wherein each $R^{11}$ is H, C(O)N(R)$_2$ (wherein each R group is, independently, hydrogen, alkyl, acyl, cycloalkyl, aryl, aralkyl, heterocyclyl, heteroaryl, or heteroarylalkyl), optionally substituted alkyl or two adjacent $R^{11}$ groups, together with the atoms to which they are attached form an optionally substituted cycloalkyl group or an optionally substituted heterocylcyl group; m is an integer from 1 to 3; and $X^1$ is O or $NR^{12}$, wherein $R^{12}$ is H or optionally substituted alkyl or $R^{12}$ and an adjacent $R^{11}$ group, together with the atoms to which they are attached, form an optionally substituted heterocyclyl group. $X^2$ can be C and $R^4$ is therefore present.

$R^{6''}$ can be:

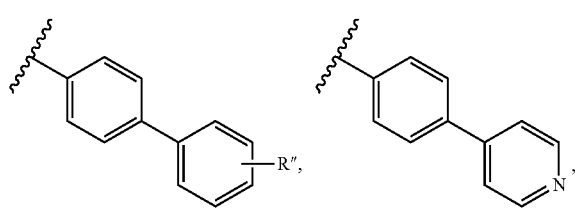

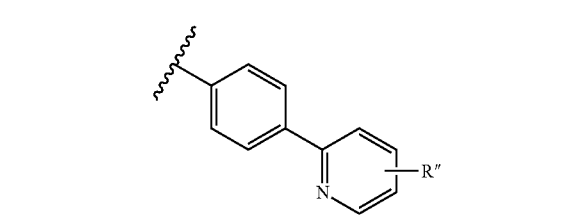

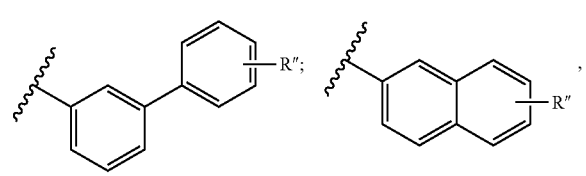

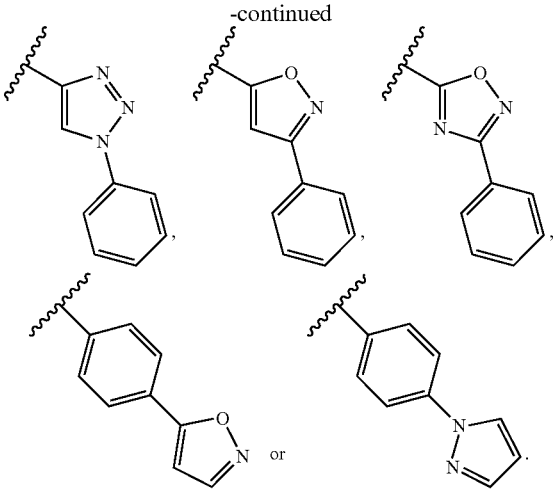

Compounds where $R^{6''}$ comprises a heteroatom (e.g., N and O) have been found to be more water soluble than their all-carbon counterparts, to the point that compounds where $R^{6''}$ comprises a heteroatom can be dosed at 30 mg/kg or more.

Various other embodiments are directed to a compound of the formula (II):

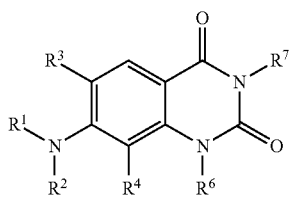

(II)

or a pharmaceutically acceptable salt, polymorph, prodrug, solvate or clathrate thereof, wherein:
$R^1$—$R^4$ and $R^6$ are as defined for compounds of the formula (I) and (Ib); and
$R^7$ is H, OH, optionally substituted alkoxy, optionally substituted alkyl or $NR^8R^9$, wherein $R^8$ and $R^9$ are each independently H, optionally substituted alkyl, optionally substituted aryl or optionally substituted arylalkyl.

Various other embodiments are directed to a compound of the formula (IIa):

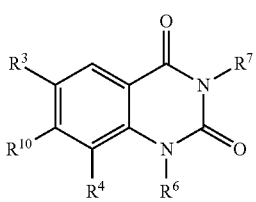

(IIa)

or a pharmaceutically acceptable salt, polymorph, prodrug, solvate or clathrate thereof, wherein:
$R^3$, $R^4$, and $R^6$ are as defined for compounds of the formula (I), (Ia), and (Ib);
$R^7$ is H, optionally substituted alkyl or $NR^8R^9$, wherein $R^8$ and $R^9$ are each independently H, optionally substituted alkyl, optionally substituted aryl or optionally substituted arylalkyl; and $R^{10}$ is aryl,

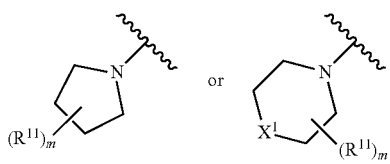

wherein each $R^{11}$ is H, $C(O)N(R)_2$ (wherein each R group is, independently, hydrogen, alkyl, acyl, cycloalkyl, aryl, aralkyl, heterocyclyl, heteroaryl, or heteroarylalkyl), optionally substituted alkyl or two adjacent $R^{11}$ groups, together with the atoms to which they are attached form an optionally substituted cycloalkyl group or an optionally substituted heterocylcyl group; m is an integer from 1 to 3; and $X^1$ is O or $NR^{12}$, wherein $R^{12}$ is H or optionally substituted alkyl or $R^{12}$ and an adjacent $R^{11}$ group, together with the atoms to which they are attached, form an optionally substituted heterocyclyl group.

Various other embodiments are directed to a compound of the formula (III) and (IV):

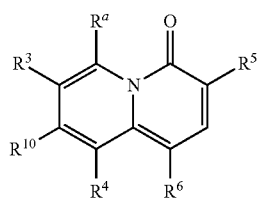

(III)

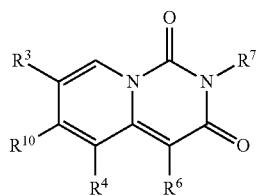

(IV)

wherein the groups $R^a$, $R^3$—$R^7$, and $R^{10}$ are as defined for the compounds of the formulae (I), (Ia), (Ib), (II), and (IIa).

In the compounds of the formulae (I), (Ia), (Ib), (II), (IIa), (III) or (IV) $R^3$ can be halo (e.g., fluoro). $R^3$ can also be H.

In the compounds of the formulae (I), (Ia), (Ib), (II), (IIa), (III) or (IV), $R^4$ can be alkoxy (e.g., methoxy). $R^4$ can also be H.

In the compounds of the formulae (I), (Ia), (Ib) or (III), $R^5$ can be —$C(O)R^{5'}$. $R^{5'}$ can be OH or optionally substituted alkoxy.

In the compounds of the formulae (I), (Ia), (II), (IIa), (III) or (IV), $R^6$ can be optionally substituted arylalkyl. In some embodiments, however, $R^6$ is not a benzyl group. But $R^6$ can be a biphenyl or a naphthyl group.

In the compounds of the formulae (II) and (IIa), $R^7$ can be $NR^8R^9$. $R^8$ can be H. And $R^8$ and $R^9$ can be H.

In the compounds of the formula (I), when $R^6$ is:

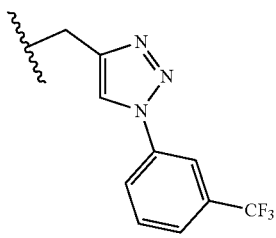 [SMILES: *Cc1cn(-c2cccc(C(F)(F)F)c2)nn1]

$R^1$ and $R^2$, together with the nitrogen atom to which they are attached, form an optionally substituted pyrrolidinyl group.

In the compounds of the formulae (Ia), (Ib), (IIa), (III) or (IV), $R^{11}$ can be optionally substituted alkyl. $R^{11}$ can be alkyl substituted with $NR^{13}R^{14}$, wherein $R^{13}$ and $R^{14}$ are each independently H, optionally substituted alkyl, optionally substituted aryl, optionally substituted arylalkyl or $R^{13}$ and $R^{14}$, together with the nitrogen atom to which they are attached, form an optionally substituted heterocyclyl group. $R^{13}$ can be H. $R^{13}$ and $R^{14}$ can be H.

In the compounds of the formulae (Ia), (Ib), (IIa), (III) or (IV), $R^{11}$ can be alkyl substituted with $OR^{13}$, wherein $R^{13}$ is H, optionally substituted alkyl, optionally substituted aryl or optionally substituted arylalkyl.

In the compounds of the formulae (Ia), (Ib), (IIa), (III) or (IV), $R^{11}$ can be $C(O)N(R)_2$, wherein each R group is, independently, hydrogen, alkyl, acyl, cycloalkyl, aryl, aralkyl, heterocyclyl, heteroaryl, or heteroarylalkyl. At least one R in the $C(O)N(R)_2$ group can be H. The $C(O)N(R)_2$ group can be a $C(O)NH_2$ group.

Compounds of the formulae (I), (Ia), (Ib), (II), (IIa), (III) or (IV) include compounds of the formulae (V) and (VI):

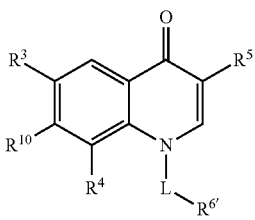

(V)

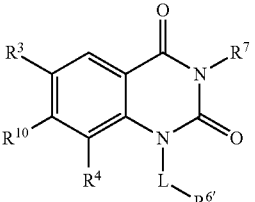

(VI)

wherein $R^3$, $R^4$, and $R^7$ are as defined for compounds of the formula (I); L is —$(CH_2)_n$—, wherein n is an integer from 1 to 3 (e.g., 1); $R^{6'}$ is:

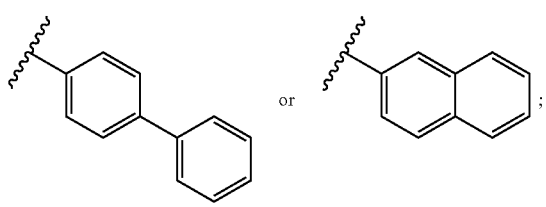 [SMILES: *c1ccc(-c2ccccc2)cc1 ; *c1ccc2ccccc2c1]

and

R¹⁰ is:

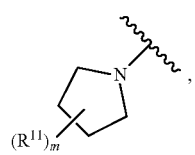

wherein R¹¹ is C(O)N(R)₂ (wherein each R group is, independently, hydrogen, alkyl, acyl, cycloalkyl, aryl, aralkyl, heterocyclyl, heteroaryl, or heteroarylalkyl), alkyl substituted with —OR or alkyl substituted with —N(R)₂. In the compound of the formula (V), R⁵ can be —C(O)OH. In the compound of the formula (VI), R⁷ can be —NH₂. In the compounds of the formula (V) or (VI), R³ can be halo (e.g., fluoro). In the compounds of the formula (V) or (VI), R⁴ can optionally substituted alkoxy (e.g., methoxy). In the compounds of the formula (V) or (VI), R¹¹ can be alkyl substituted with —N(R)₂. R¹¹ can be alkyl substituted with —NRH (e.g., R¹¹ is —CH₂NHCH₃). In the compounds of the formula (V) or (VI), R¹¹ can be alkyl substituted with —OR. R¹¹ can be alkyl substituted with —OH (e.g., R¹¹ is —CH₂OH). R¹¹ can be —C(O)N(R)₂. R¹¹ can be —C(O)NH₂.

Representative compounds of the formulae (I), (Ia), (Ib), (II), (IIa), (V) or (VI) include compounds of the formulae:

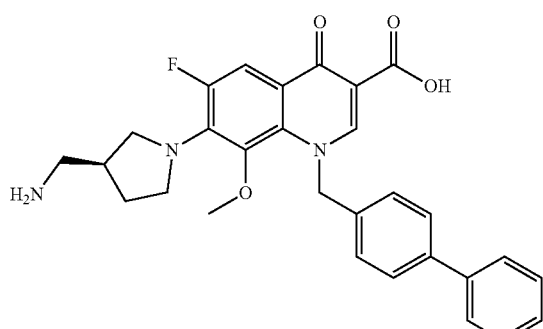

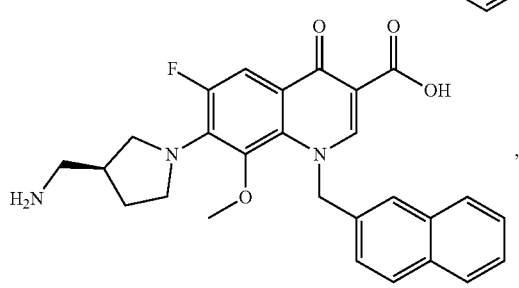

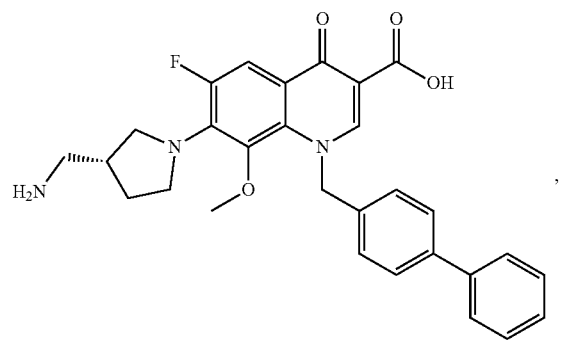

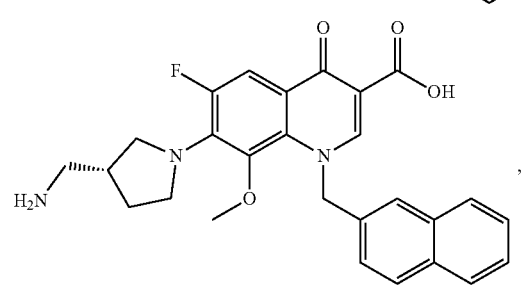

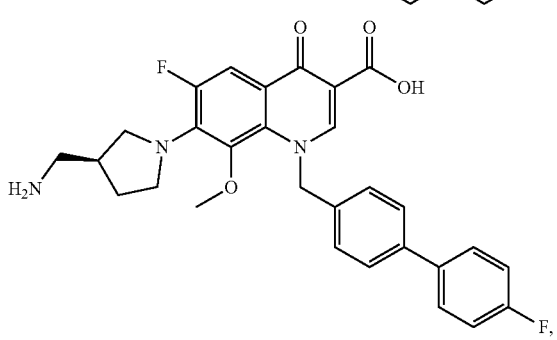

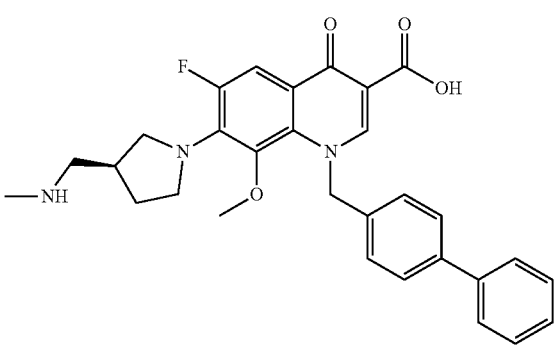

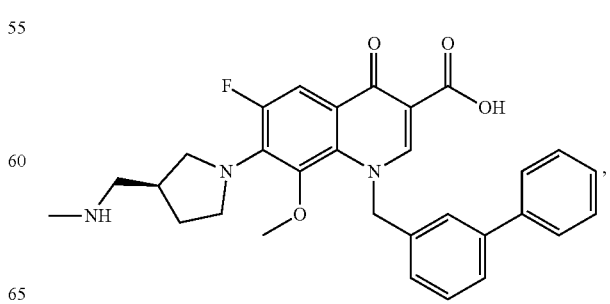

-continued
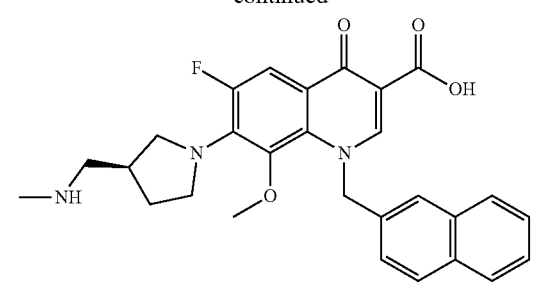
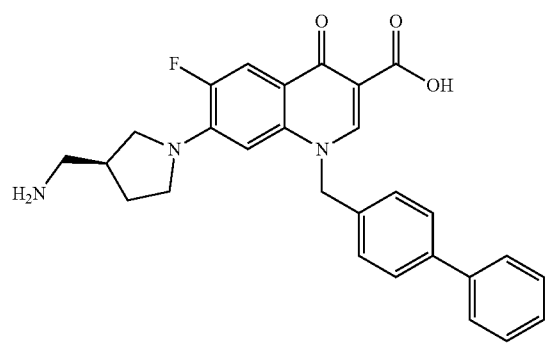
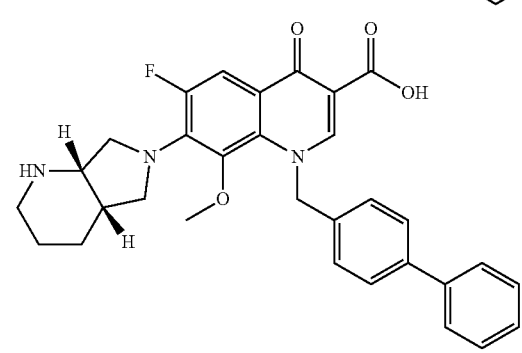
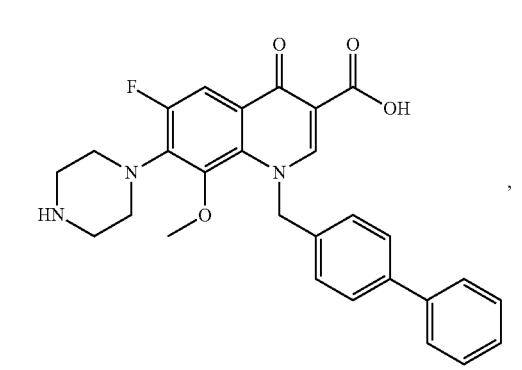
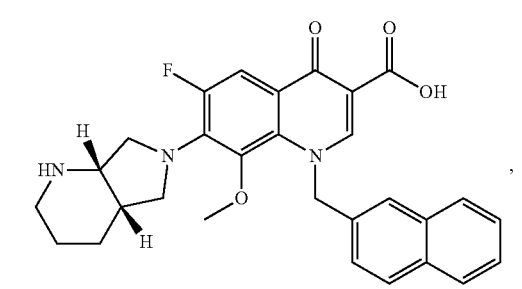
-continued
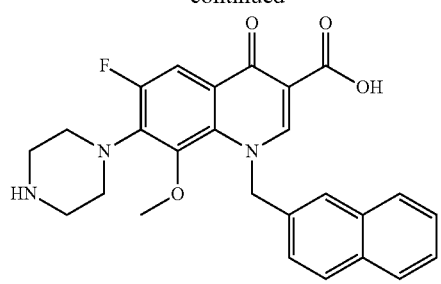
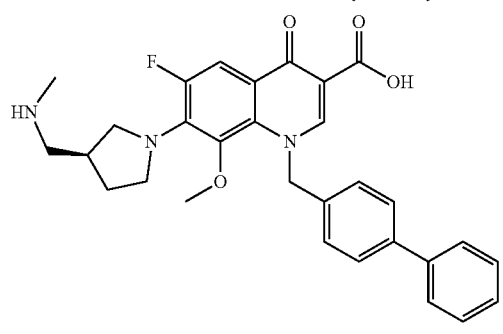
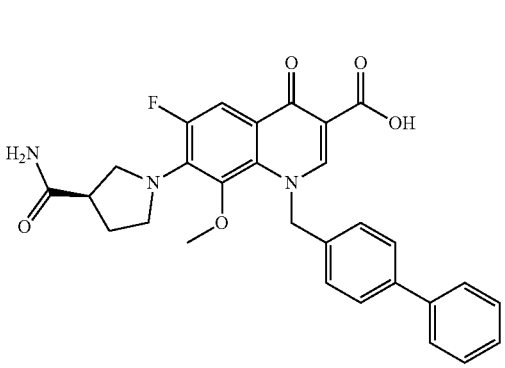
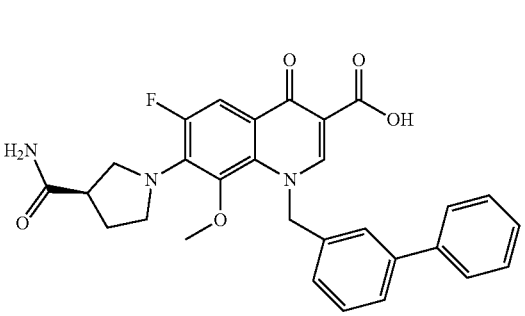
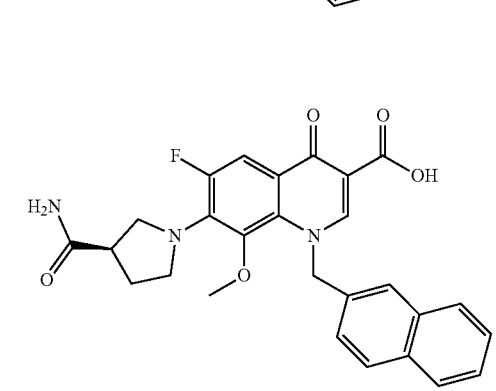

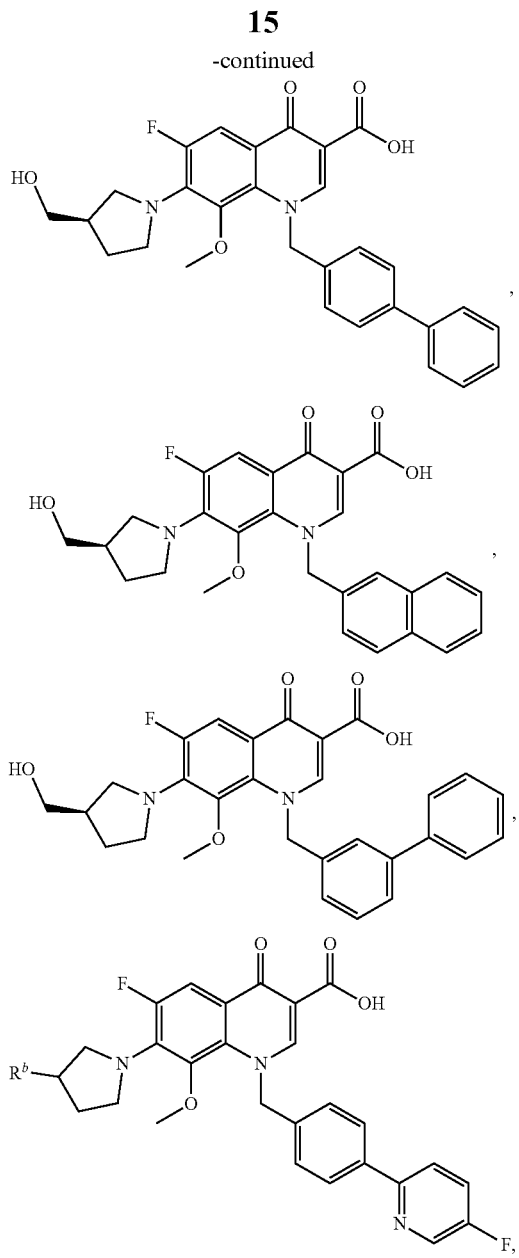
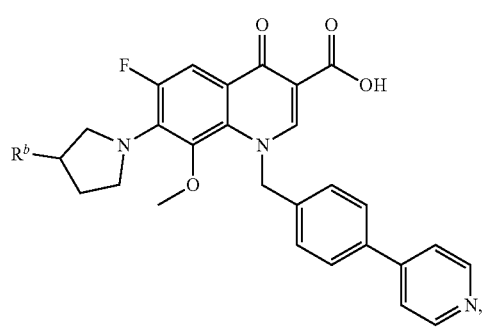
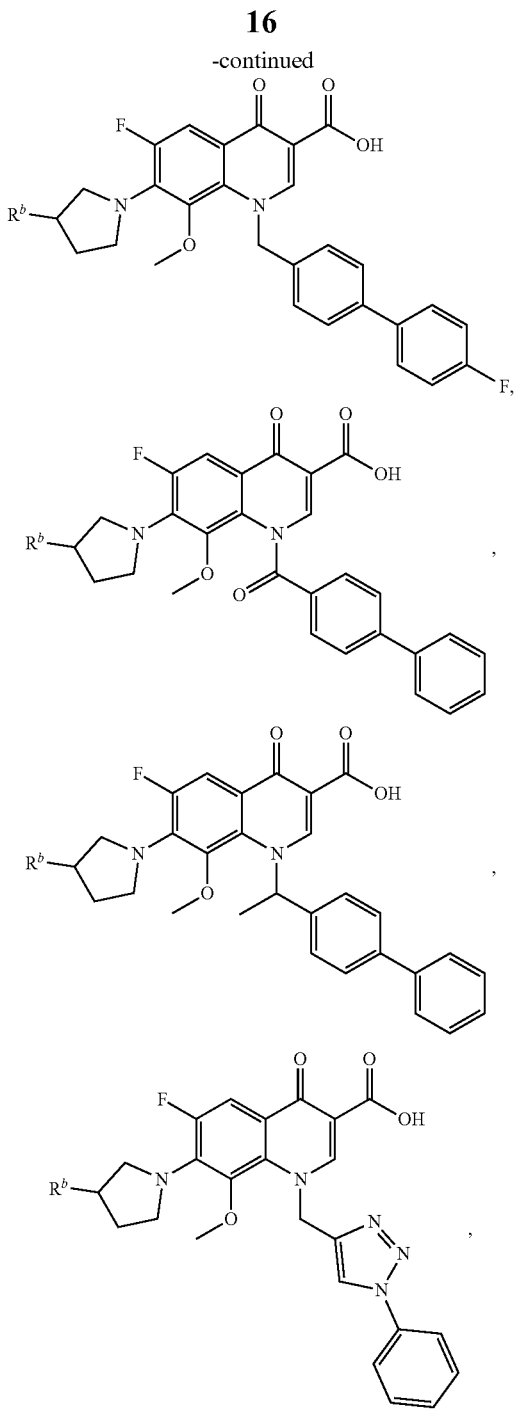

-continued
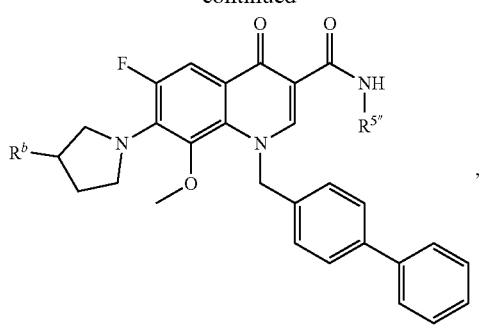
(wherein R[5″] is defined herein);
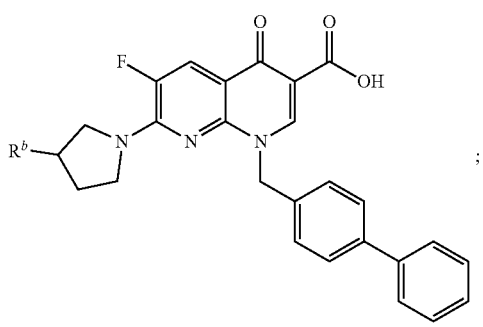
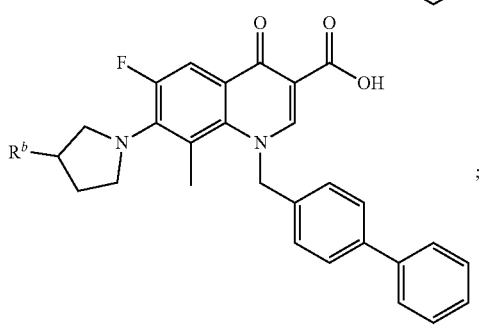
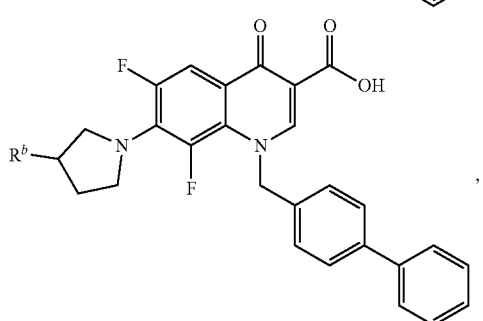
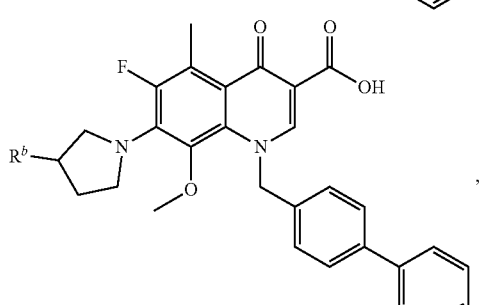
-continued
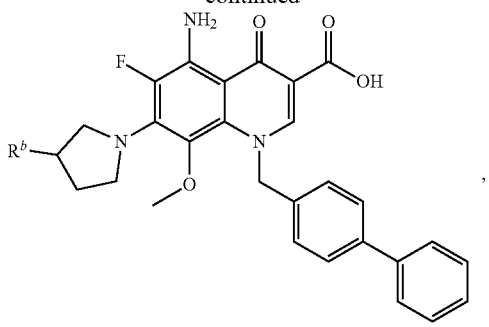
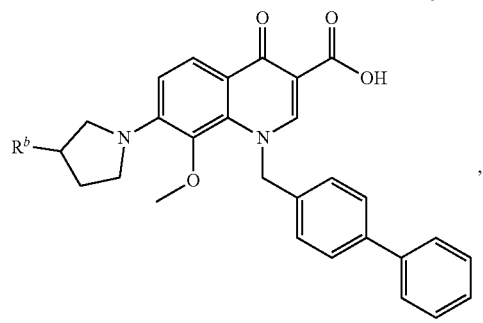
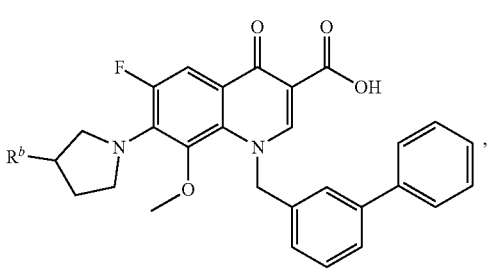
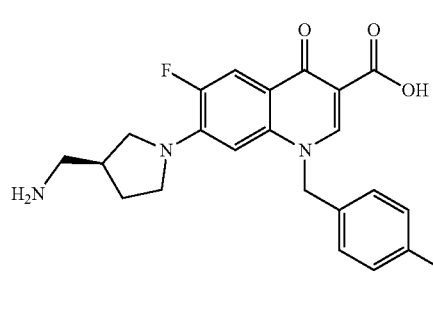
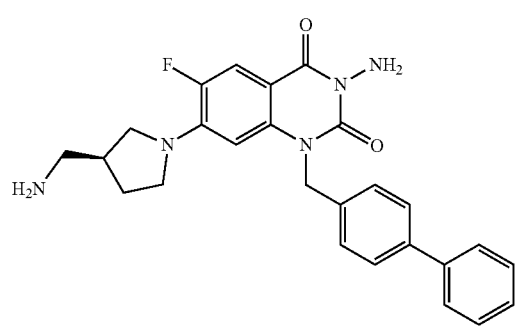

-continued
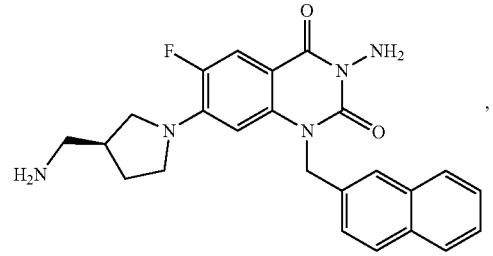
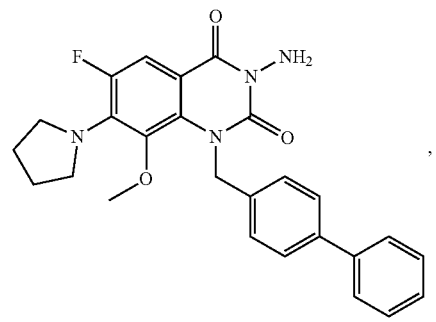
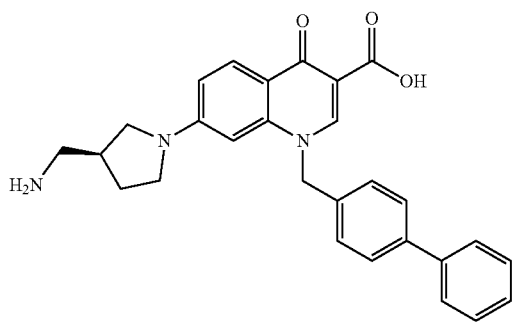
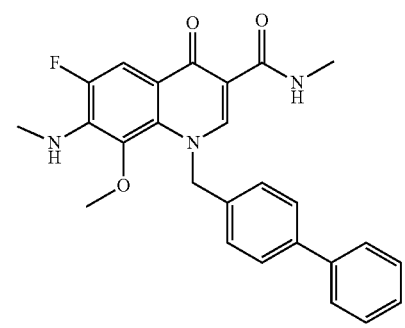
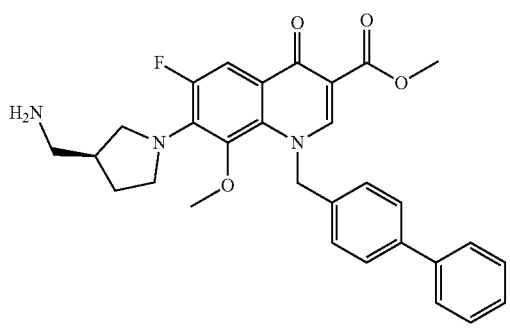
-continued
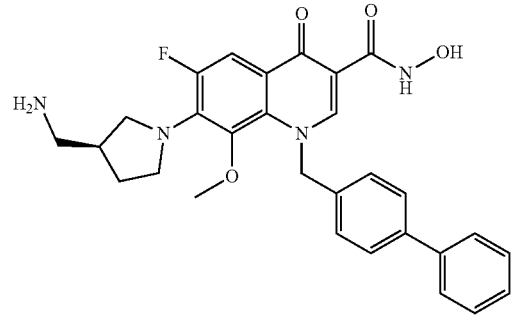
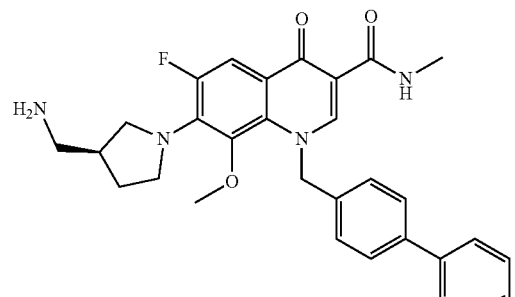
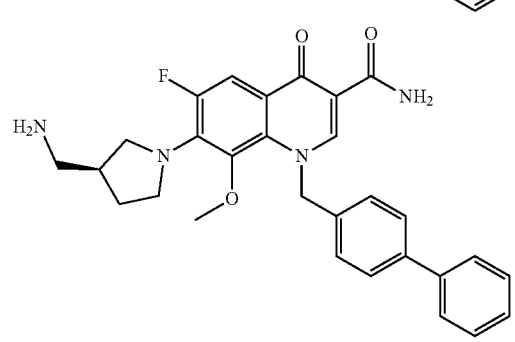
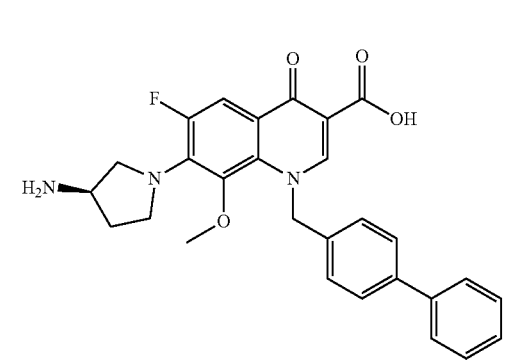
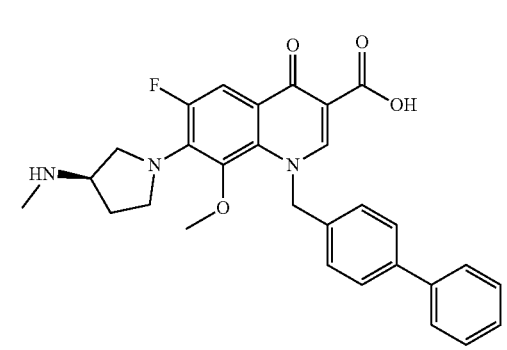

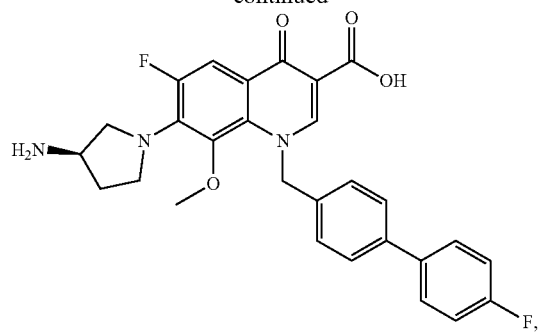
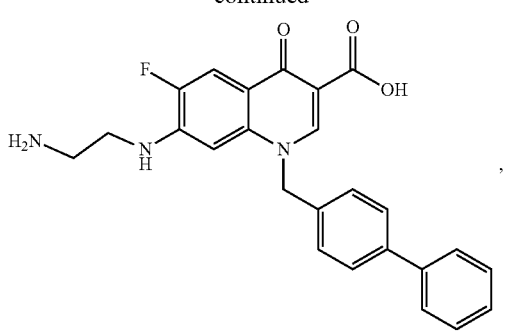
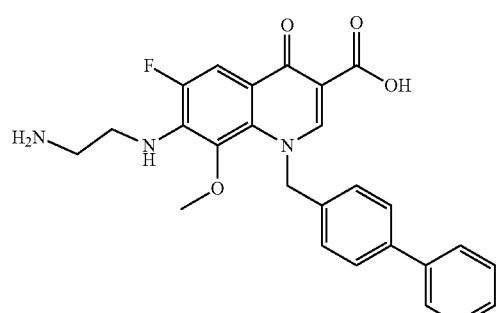
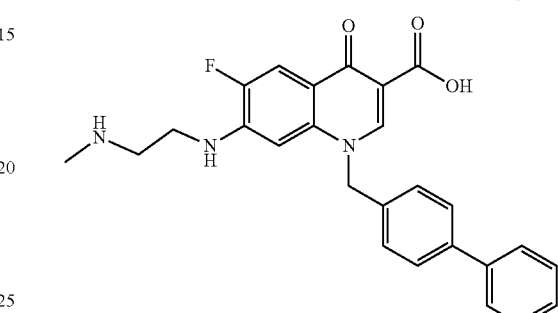
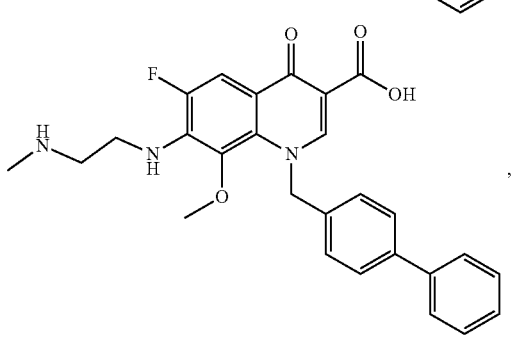
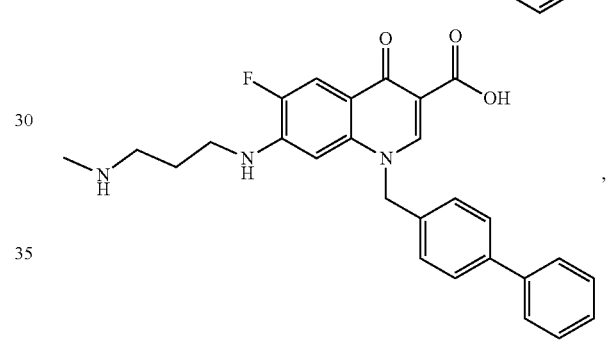
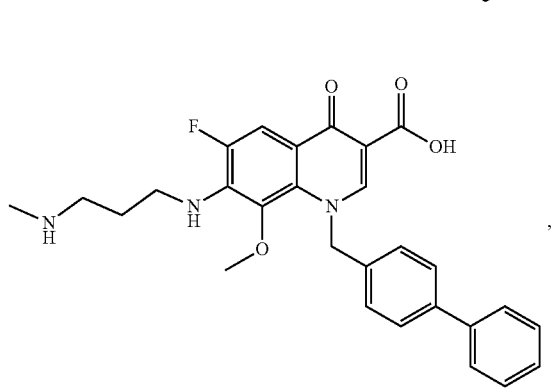
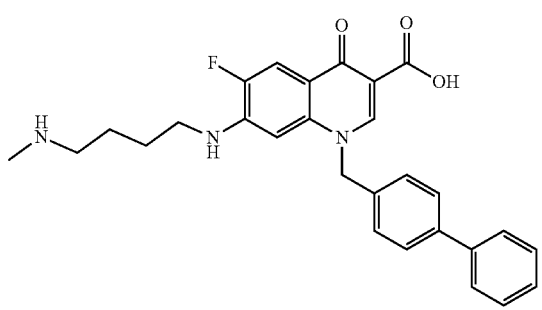
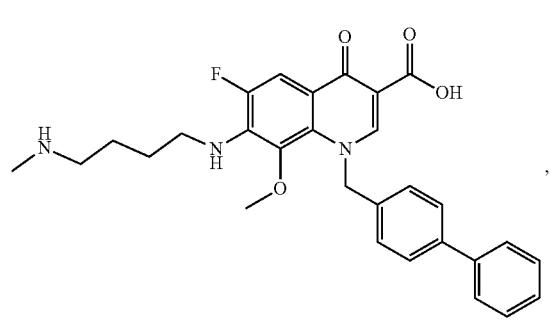
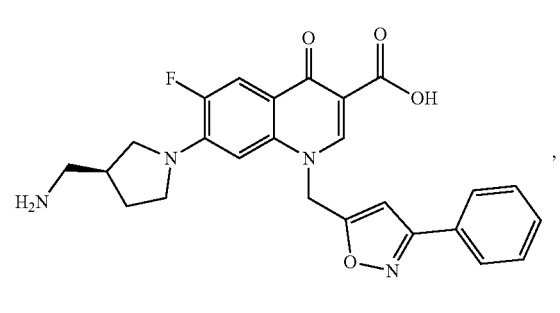

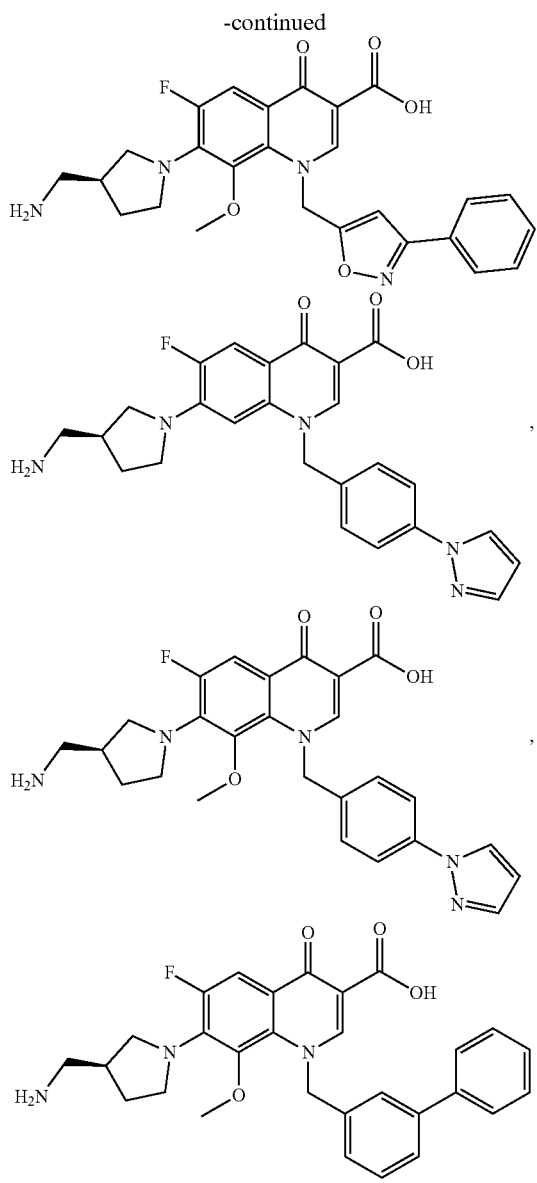

or
pharmaceutically acceptable salts (e.g., the hydrochloride salts, where a primary or secondary amine group is protonated), polymorphs, prodrugs, solvates or clathrates thereof.

Those of ordinary skill in the art will recognize that compounds described herein can contain chiral centers. All diastereomers of the compounds described herein are contemplated herein, as well as racemates.

Various embodiments also contemplate pharmaceutical compositions comprising one or more compounds described herein and one or more pharmaceutically acceptable carriers, diluents, excipients or combinations thereof. A "pharmaceutical composition" refers to a chemical or biological composition suitable for administration to a subject (e.g., mammal). Such compositions may be specifically formulated for administration via one or more of a number of routes, including but not limited to buccal, cutaneous, epicutaneous, epidural, infusion, inhalation, intraarterial, intracardial, intracerebroventricular, intradermal, intramuscular, intranasal, intraocular, intraperitoneal, intraspinal, intrathe- cal, intravenous, oral, parenteral, pulmonary, rectally via an enema or suppository, subcutaneous, subdermal, sublingual, transdermal, and transmucosal. In addition, administration can by means of capsule, drops, foams, gel, gum, injection, liquid, patch, pill, porous pouch, powder, tablet, or other suitable means of administration.

A "pharmaceutical excipient" or a "pharmaceutically acceptable excipient" comprises a carrier, sometimes a liquid, in which an active therapeutic agent is formulated. The excipient generally does not provide any pharmacological activity to the formulation, though it may provide chemical and/or biological stability, and release characteristics. Examples of suitable formulations can be found, for example, in Remington, The Science And Practice of Pharmacy, 20th Edition, (Gennaro, A. R., Chief Editor), Philadelphia College of Pharmacy and Science, 2000, which is incorporated by reference in its entirety.

As used herein "pharmaceutically acceptable carrier" or "excipient" includes any and all solvents, dispersion media, coatings, antibacterial and antifungal agents, isotonic and absorption delaying agents that are physiologically compatible. In one embodiment, the carrier is suitable for parenteral administration. Alternatively, the carrier can be suitable for intravenous, intraperitoneal, intramuscular, sublingual, or oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

Pharmaceutical compositions may be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (e.g., glycerol, propylene glycol, and liquid polyethylene glycol), and suitable mixtures thereof. The proper fluidity can be maintained, for example, by the use of a coating such as lecithin, by the maintenance of the required particle size in the case of dispersion and by the use of surfactants.

In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin. Moreover, the compounds described herein can be formulated in a time release formulation, for example in a composition that includes a slow release polymer. The active compounds can be prepared with carriers that will protect the compound against rapid release, such as a controlled release formulation, including implants and microencapsulated delivery systems. Biodegradable, biocompatible polymers may be used, such as ethylene vinyl acetate, polyanhydrides, polyglycolic acid, collagen, polyorthoesters, polylactic acid and polylactic, polyglycolic copolymers (PLG). Many methods for the preparation of such formulations are known to those skilled in the art.

Oral forms of administration are also contemplated herein. The pharmaceutical compositions may be orally administered as a capsule (hard or soft), tablet (film coated, enteric coated or uncoated), powder or granules (coated or uncoated) or liquid (solution or suspension). The formulations may be conveniently prepared by any of the methods well-known in the art. The pharmaceutical compositions may include one or more suitable production aids or excipients including fillers, binders, disintegrants, lubricants, diluents, flow agents, buffering agents, moistening agents, preservatives, colorants, sweeteners, flavors, and pharmaceutically compatible carriers.

For each of the recited embodiments, the compounds can be administered by a variety of dosage forms as known in the art. Any biologically-acceptable dosage form known to persons of ordinary skill in the art, and combinations thereof, are contemplated. Examples of such dosage forms include, without limitation, chewable tablets, quick dissolve tablets, effervescent tablets, reconstitutable powders, elixirs, liquids, solutions, suspensions, emulsions, tablets, multilayer tablets, bi-layer tablets, capsules, soft gelatin capsules, hard gelatin capsules, caplets, lozenges, chewable lozenges, beads, powders, gum, granules, particles, microparticles, dispersible granules, cachets, douches, suppositories, creams, topicals, inhalants, aerosol inhalants, patches, particle inhalants, implants, depot implants, ingestibles, injectables (including subcutaneous, intramuscular, intravenous, and intradermal), infusions, and combinations thereof.

Other compounds which can be included by admixture are, for example, medically inert ingredients (e.g., solid and liquid diluent), such as lactose, dextrosesaccharose, cellulose, starch or calcium phosphate for tablets or capsules, olive oil or ethyl oleate for soft capsules and water or vegetable oil for suspensions or emulsions; lubricating agents such as silica, talc, stearic acid, magnesium or calcium stearate and/or polyethylene glycols; gelling agents such as colloidal clays; thickening agents such as gum tragacanth or sodium alginate, binding agents such as starches, arabic gums, gelatin, methylcellulose, carboxymethylcellulose or polyvinylpyrrolidone; disintegrating agents such as starch, alginic acid, alginates or sodium starch glycolate; effervescing mixtures; dyestuff; sweeteners; wetting agents such as lecithin, polysorbates or laurylsulphates; and other therapeutically acceptable accessory ingredients, such as humectants, preservatives, buffers and antioxidants, which are known additives for such formulations.

Liquid dispersions for oral administration can be syrups, emulsions, solutions, or suspensions. The syrups can contain as a carrier, for example, saccharose or saccharose with glycerol and/or mannitol and/or sorbitol. The suspensions and the emulsions can contain a carrier, for example a natural gum, agar, sodium alginate, pectin, methylcellulose, carboxymethylcellulose, or polyvinyl alcohol.

The amount of active compound in a therapeutic composition according to various embodiments described herein may vary according to factors such as the disease state, age, gender, weight, patient history, risk factors, predisposition to disease, administration route, pre-existing treatment regime (e.g., possible interactions with other medications), and weight of the individual. Dosage regimens may be adjusted to provide the optimum therapeutic response. For example, a single bolus may be administered, several divided doses may be administered over time, or the dose may be proportionally reduced or increased as indicated by the exigencies of therapeutic situation.

"Dosage unit form," as used herein, refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of sensitivity in individuals. In therapeutic use for treatment of conditions in mammals (e.g., humans) for which the compounds described herein or an appropriate pharmaceutical composition thereof are effective, the compounds may be administered in an effective amount. The suitable dosages may be a composition, a pharmaceutical composition or any other compositions described herein.

For each of the recited embodiments, the dosage is typically administered once, twice, or thrice a day, although more frequent dosing intervals are possible. The dosage may be administered every day, every 2 days, every 3 days, every 4 days, every 5 days, every 6 days, and/or every 7 days (once a week). In one embodiment, the dosage may be administered daily for up to and including 30 days, preferably between 7-10 days. In another embodiment, the dosage may be administered twice a day for 10 days. If the patient requires treatment for a chronic disease or condition, the dosage may be administered for as long as signs and/or symptoms persist. The patient may require "maintenance treatment" where the patient is receiving dosages every day for months, years, or the remainder of their lives. In addition, the composition of this invention may be to effect prophylaxis of recurring symptoms. For example, the dosage may be administered once or twice a day to prevent the onset of symptoms in patients at risk, especially for asymptomatic patients.

The compositions described herein may be administered in any of the following routes: buccal, epicutaneous, epidural, infusion, inhalation, intraarterial, intracardial, intracerebroventricular, intradermal, intramuscular, intranasal, intraocular, intraperitoneal, intraspinal, intrathecal, intravenous, oral, parenteral, pulmonary, rectally via an enema or suppository, subcutaneous, subdermal, sublingual, transdermal, and transmucosal. The preferred routes of administration are buccal and oral. The administration can be local, where the composition is administered directly, close to, in the locality, near, at, about, or in the vicinity of, the site(s) of disease, e.g., inflammation, or systemic, wherein the composition is given to the patient and passes through the body widely, thereby reaching the site(s) of disease. Local administration can be administration to the cell, tissue, organ, and/or organ system, which encompasses and/or is affected by the disease, and/or where the disease signs and/or symptoms are active or are likely to occur. Administration can be topical with a local effect, composition is applied directly where its action is desired. Administration can be enteral wherein the desired effect is systemic (non-local), composition is given via the digestive tract. Administration can be parenteral, where the desired effect is systemic, composition is given by other routes than the digestive tract.

Various embodiments contemplate compositions comprising a therapeutically effective amount of one or more compounds of the various embodiments described herein. In some embodiments, the compositions are useful in a method for treating cancer, the method comprising administering a therapeutically effective amount of one or more compounds to a patient in need thereof. Various embodiments are directed to compounds of the various embodiments described herein for use as a medicament for treating a patient in need of relief from cancer.

The term "therapeutically effective amount" as used herein, refers to that amount of one or more compounds of the various embodiments described herein that elicits a biological or medicinal response in a tissue system, animal or human, that is being sought by a researcher, veterinarian, medical doctor or other clinician, which includes alleviation of the symptoms of the disease or disorder being treated. In some embodiments, the therapeutically effective amount is that which may treat or alleviate the disease or symptoms of the disease at a reasonable benefit/risk ratio applicable to any medical treatment. However, it is to be understood that the total daily usage of the compounds and compositions described herein may be decided by the attending physician within the scope of sound medical judgment. The specific therapeutically-effective dose level for any particular patient will depend upon a variety of factors, including the condition being treated and the severity of the condition; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors well known to the researcher, veterinarian, medical doctor or other clinician. It is also appreciated that the therapeutically effective amount can be selected with reference to any toxicity, or other undesirable side effect, that might occur during administration of one or more of the compounds described herein.

In some embodiments, the compounds of the various embodiments described herein have a half maximal inhibitory concentration ($IC_{50}$ for human topoisomerase I, using relaxation assays, of from about 100 nM to about 200 μM (e.g., about 900 nM to about 50 μM, about 1 μM to about 100 μM, about 10 μM to about 100 μM, about 20 μM to about 100 μM, about 20 μM to about 50 μM, about 20 μM to about 30 μM or about 10 μM to about 90 μM).

In some embodiments, the compounds of the various embodiments described herein have an $IC_{50}$ for human topoisomerase II, using decatenation assays, of from about 200 nM to about 400 μM (e.g., about 50 μM to about 250 μM, about 50 μM to about 180 μM, about 100 μM to about 300 μM, about 100 μM to about 200 μM, about 100 μM to about 150 μM, about 110 μM to about 180 μM or about 120 μM to about 180 μM).

In some embodiments, the $IC_{50}$ for human topoisomerase I is about four times lower than the $IC_{50}$ for human topoisomerase II. In other embodiments, the $IC_{50}$ for human topoisomerase I is at least about two (e.g., about two to about 10,000) times lower than the $IC_{50}$ for human topoisomerase II (e.g., the $IC_{50}$ for human topoisomerase II is about two to about 10,000 times greater than the $IC_{50}$ for human topoisomerase I).

Values expressed in a range format should be interpreted in a flexible manner to include not only the numerical values explicitly recited as the limits of the range, but also to include all the individual numerical values or sub-ranges encompassed within that range as if each numerical value and sub-range were explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. In addition, it is to be understood that the phraseology or terminology employed herein, and not otherwise defined, is for the purpose of description only and not of limitation. Any use of section headings is intended to aid reading of the document and is not to be interpreted as limiting. Further, information that is relevant to a section heading may occur within or outside of that particular section. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

In the methods described herein, the steps can be carried out in any order without departing from the principles of the invention, except when a temporal or operational sequence is explicitly recited. Furthermore, specified steps can be carried out concurrently unless explicit claim language recites that they be carried out separately. For example, a claimed step of doing X and a claimed step of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more.

The term "substituted" or "substituent" as used herein refers to a group that can be or is substituted onto a molecule or onto another group. Examples of substituents include, but are not limited to, a halogen (e.g., F, Cl, Br, and I), OR, $OC(O)N(R)_2$, CN, NO, $NO_2$, $ONO_2$, azido, $CF_3$, $OCF_3$, R, O (oxo), S (thiono), C(O), S(O), methylenedioxy, ethylenedioxy, $N(R)_2$, SR, SOR, $SO_2R$, $SO_2N(R)_2$, $SO_3R$, $-(CH_2)_{0-2}P(O)(OR)_2$, C(O)R, C(O)C(O)R, $C(O)CH_2C(O)$ R, C(S)R, C(O)OR, OC(O)R, $C(O)N(R)_2$, $OC(O)N(R)_2$, $C(S)N(R)_2$, $(CH_2)_{0-2}N(R)C(O)R$, $(CH_2)_{0-2}N(R)C(O)OR$, $(CH_2)_{0-2}N(R)N(R)_2$, $N(R)N(R)C(O)R$, $N(R)N(R)C(O)OR$, $N(R)N(R)CON(R)_2$, $N(R)SO_2R$, $N(R)SO_2N(R)_2$, $N(R)C(O)$ OR, N(R)C(O)R, N(R)C(S)R, $N(R)C(O)N(R)_2$, N(R)C(S)N $(R)_2$, N(COR)COR, N(OR)R, $C(=NH)N(R)_2$, C(O)N(OR) R, or C(=NOR)R wherein each R can be, independently, hydrogen, alkyl, acyl, cycloalkyl, aryl, aralkyl, heterocyclyl, heteroaryl, or heteroarylalkyl, wherein any alkyl, acyl, cycloalkyl, aryl, aralkyl, heterocyclyl, heteroaryl, or heteroarylalkyl or two R groups bonded to a nitrogen atom or to adjacent nitrogen atoms can together with the nitrogen atom or atoms form a heterocyclyl, which can be mono- or independently multi-substituted.

The term "alkyl" as used herein refers to substituted or unsubstituted straight chain and branched alkyl groups and cycloalkyl groups having from 1 to 40 carbon atoms ($C_1$-$C_{40}$), 1 to about 20 carbon atoms ($C_1$-$C_{20}$), 1 to 12 carbons ($C_1$-$C_{12}$), 1 to 8 carbon atoms ($C_1$-$C_8$), or, in some embodiments, from 1 to 6 carbon atoms ($C_1$-$C_6$). Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed herein, for example, amino, hydroxy, cyano, carboxy, nitro, thio, alkoxy, and halogen groups.

The term "cycloalkyl" as used herein refers to substituted or unsubstituted cyclic alkyl groups such as, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 4, 5, 6, or 7. In some embodiments, cycloalkyl groups can have 3 to 6 carbon atoms ($C_3$-$C_6$). Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like.

The term "cycloalkylalkyl" as used herein refers to substituted or unsubstituted alkyl groups as defined herein in which a hydrogen or carbon bond of an alkyl group as defined herein is replaced with a bond to a cycloalkyl group as defined herein. Representative cycloalkylalkyl groups include, but are not limited to, cyclopentylalkyl.

The term "alkylcycloalkyl" as used herein refers to substituted or unsubstituted cycloalkyl groups as defined herein in which a hydrogen of a cycloalkyl group as defined herein is replaced with a bond to an alkyl group as defined herein. Representative alkylcycloalkyl groups include, but are not limited to, alkylcyclopropyl.

The term "acyl" as used herein refers to a group containing a carbonyl moiety wherein the group is bonded via the carbonyl carbon atom. The carbonyl carbon atom is also bonded to another carbon atom, which can be part of a substituted or unsubstituted alkyl, aryl, aralkyl cycloalkyl, cycloalkylalkyl, heterocyclyl, heterocyclylalkyl, heteroaryl, heteroarylalkyl group or the like. In the special case wherein the carbonyl carbon atom is bonded to a hydrogen, the group is a "formyl" group, an acyl group as the term is defined herein. An acyl group can include 0 to about 12-40, 6-10, 1-5 or 2-5 additional carbon atoms bonded to the carbonyl group. An acryloyl group is an example of an acyl group. An acyl group can also include heteroatoms within the meaning here. A nicotinoyl group (pyridyl-3-carbonyl) is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "heterocyclylcarbonyl" is an example of an acyl group that is bonded to a substituted or unsubstituted heterocyclyl group, as the term "heterocyclyl" is defined herein. An example of a heterocyclylcarbonyl group is a prolyl group, wherein the prolyl group can be a D- or an L-prolyl group.

The term "aryl" as used herein refers to substituted or unsubstituted cyclic aromatic hydrocarbons that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons ($C_6$-$C_{14}$) or from 6 to 10 carbon atoms ($C_6$-$C_{10}$) in the ring portions of the groups. Aryl groups can be unsubstituted or substituted, as defined herein. Representative substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those listed herein.

The term "aralkyl" and "arylalkyl" as used herein refers to alkyl groups as defined herein in which a hydrogen or carbon bond of an alkyl group is replaced with a bond to an aryl group as defined herein. Representative aralkyl groups include benzyl and phenylethyl groups and fused (cycloalkylaryl)alkyl groups such as 4-ethyl-indanyl. Aralkenyl groups are alkenyl groups as defined herein in which a hydrogen or carbon bond of an alkyl group is replaced with a bond to an aryl group as defined herein.

The term "heterocyclyl" as used herein refers to substituted or unsubstituted aromatic and non-aromatic ring compounds containing 3 or more ring members, of which, one or more (e.g., 1, 2 or 3) is a heteroatom such as, but not limited to, N, O, and S. Thus, a heterocyclyl can be a cycloheteroalkyl, or a heteroaryl, or if polycyclic, any combination thereof. In some embodiments, heterocyclyl groups include 3 to about 20 ring members, whereas other such groups have 3 to about 15 ring members. In some embodiments, heterocyclyl groups include heterocyclyl groups that include 3 to 8 carbon atoms ($C_3$-$C_8$), 3 to 6 carbon atoms ($C_3$-$C_6$), 3 to 5 carbon atoms ($C_3$-$C_5$) or 6 to 8 carbon atoms ($C_6$-$C_8$). A heterocyclyl group designated as a $C_2$-heterocyclyl can be a 5-ring with two carbon atoms and three heteroatoms, a 6-ring with two carbon atoms and four heteroatoms and so forth. Likewise a $C_4$-heterocyclyl can be a 5-ring with one heteroatom, a 6-ring with two heteroatoms, and so forth. The number of carbon atoms plus the number of heteroatoms equals the total number of ring atoms. A heterocyclyl ring can also include one or more double bonds. A heteroaryl ring is an embodiment of a heterocyclyl group. The phrase "heterocyclyl group" includes fused ring species including those that include fused aromatic and non-aromatic groups. Representative heterocyclyl groups include, but are not limited to pyrrolidinyl, azetidinyl, piperidynyl, piperazinyl, morpholinyl, chromanyl, indolinonyl, isoindolinonyl, furanyl, pyrrolidinyl, pyridinyl, pyrazinyl, pyrimidinyl, triazinyl, thiophenyl, tetrahydrofuranyl, pyrrolyl, oxazolyl, oxadiazolyl, imidazolyl, triazyolyl, tetrazolyl, benzoxazolinyl, benzthiazolinyl, and benzimidazolinyl groups.

The term "heterocyclylalkyl" as used herein refers to alkyl groups as defined herein in which a hydrogen or carbon bond of an alkyl group as defined herein is replaced with a bond to a heterocyclyl group as defined herein. Representative heterocyclylalkyl groups include, but are not limited to, furan-2-yl methyl, furan-3-yl methyl, pyridine-3-yl methyl, tetrahydrofuran-2-yl methyl, and indol-2-yl propyl.

The term "heterocyclylalkoxy" as used herein refers to alkyl groups as defined herein in which a hydrogen or carbon bond of an alkyl group as defined herein is replaced with a bond to a heterocyclyl group as defined herein and the alkyl group is attached to an oxygen. Representative heterocyclylalkoxy groups include, but are not limited to, —O—$(CH_2)_q$heterocyclyl, wherein q is an integer from 1 to 5. In some embodiments, heterocyclylalkoxy groups include —O—$(CH_2)_q$morpholinyl such as —O—$CH_2CH_2$-morpholine.

The term "heteroarylalkyl" as used herein refers to alkyl groups as defined herein in which a hydrogen or carbon bond of an alkyl group is replaced with a bond to a heteroaryl group as defined herein.

The term "alkoxy" as used herein refers to an oxygen atom connected to an alkyl group, including a cycloalkyl group, as are defined herein. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can include one to about 12-20 or about 12-40 carbon atoms bonded to the oxygen atom, and can further include double or triple bonds, and can also include heteroatoms. For example, an allyloxy group is an alkoxy group within the meaning herein. A methoxyethoxy group is also an alkoxy group within the meaning herein, as is a methylenedioxy group in a context where two adjacent atoms of a structure are substituted therewith.

The term "amine" as used herein refers to primary, secondary, and tertiary amines having, e.g., the formula N(group)$_3$ wherein each group can independently be H or non-H, such as alkyl, aryl, and the like. Amines include but are not limited to R—NH$_2$, for example, alkylamines, arylamines, alkylarylamines; R$_2$NH wherein each R is independently selected, such as dialkylamines, diarylamines, aralkylamines, heterocyclylamines and the like; and R$_3$N wherein each R is independently selected, such as trialkylamines, dialkylarylamines, alkyldiarylamines, triarylamines, and the like. The term "amine" also includes ammonium ions as used herein.

The term "amino group" as used herein refers to a substituent of the form —NH$_2$, —NHR, —NR$_2$, —NR$_3^+$, wherein each R is independently selected, and protonated forms of each, except for —NR$_3^+$, which cannot be protonated. Accordingly, any compound substituted with an amino group can be viewed as an amine. An "amino group" within the meaning herein can be a primary, secondary, tertiary, or quaternary amino group. An "alkylamino" group includes a monoalkylamino, dialkylamino, and trialkylamino group.

The terms "halo," "halogen," or "halide" group, as used herein, by themselves or as part of another substituent, mean, unless otherwise stated, a fluorine, chlorine, bromine, or iodine atom.

The term "haloalkyl" group, as used herein, includes mono-halo alkyl groups, poly-halo alkyl groups wherein all halo atoms can be the same or different, and per-halo alkyl groups, wherein all hydrogen atoms are replaced by halogen atoms, such as fluoro.

Examples of haloalkyl include trifluoromethyl, 1,1-dichloroethyl, 1,2-dichloroethyl, 1,3-dibromo-3,3-difluoropropyl, perfluorobutyl, —CF(CH$_3$)$_2$ and the like.

As used herein, the term "salts" and "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. Pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, trifluoroacetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic acids, and the like.

Pharmaceutically acceptable salts can be synthesized from the parent compound which contains a basic or acidic moiety by conventional chemical methods. In some instances, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, the disclosure of which is hereby incorporated by reference.

The term "solvate" means a compound, or a salt thereof, that further includes a stoichiometric or non-stoichiometric amount of solvent bound by non-covalent intermolecular forces. Where the solvent is water, the solvate is a hydrate.

The term "prodrug" means a derivative of a compound that can hydrolyze, oxidize, or otherwise react under biological conditions (in vitro or in vivo) to provide an active compound, particularly a compound of the invention. Examples of prodrugs include, but are not limited to, derivatives and metabolites of a compound of the invention that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Specific prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by Burger's Medicinal Chemistry and Drug Discovery 6th ed. (Donald J. Abraham ed., 2001, Wiley) and Design and Application of Prodrugs (H. Bundgaard ed., 1985, Harwood Academic Publishers GmbH).

EXAMPLES

The following examples which are offered by way of illustration and do not limit the scope of the claims presented herein.

Example 1

Preparation of (S)-7-(3-(aminomethyl)pyrrolidin-1-yl)-6-fluoro-8-methoxy-1-(naphthalen-2-ylmethyl)-4-oxo-1,4-dihydroquinoline-3-carboxylic acid (UITT-III-227)

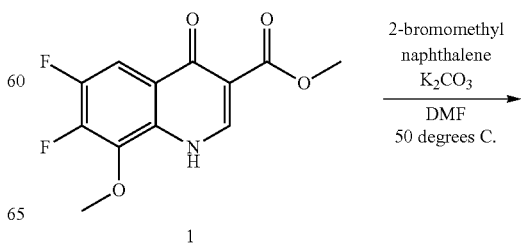

-continued

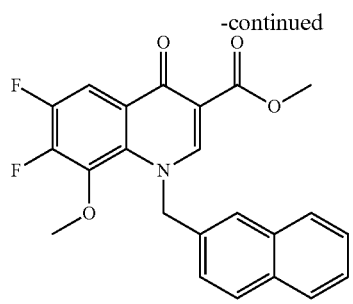

2

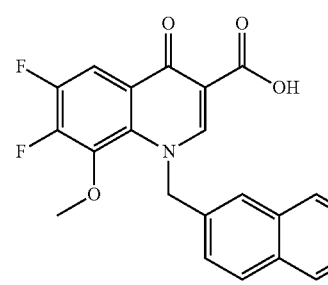

3

1. Boc—R aminomethyl pyrrolidine
TEA
DMSO
2. TFA

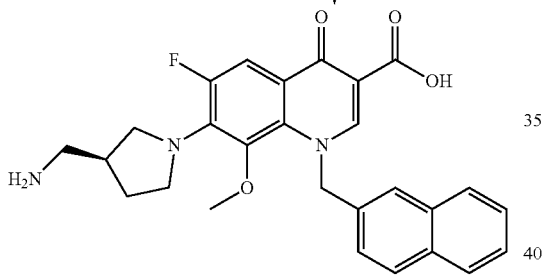

(UITT-III-227)

Compound 2 (56.6 mg, 0.138 mmol) was dissolved in 2:1 THF:1% LiOH in H$_2$O and stirred at room temperature for 1 hour. The THF was removed by rotary evaporation and the aqueous layer was acidified to pH 1 with 4.0 N HCl. The aqueous layer was then extracted four times with 10 mL dichloromethane (DCM) and the combined organic layers were washed with brine, dried over Na$_2$SO$_4$, filtered, and concentrated by rotary evaporation. The residue was then dissolved in 1.5 mL anhydrous dimethylsulfoxide (DMSO) and heated to 50° C. with stirring. Boc-(R)-aminomethylpyrrolidine (61.6 mg, 0.308 mmol) and TEA (100 μL, 0.717 mmol) were added and the reaction stirred for 24 hours. Trifluoroacetic acid (TFA; 3 mL) was added and the reaction was allowed to cool to room temperature and stir overnight. The solution was then diluted with water and the product 4 was purified by preparatory HPLC. 89% yield over 3 steps. $^1$H NMR (300 MHz, dDMSO) δ=15.24 (bs, 1H), 9.13 (s, 1H), 7.96 (bs, 3H), 7.86 (m, 3H), 7.69 (m, 2H), 7.47 (m, 2H), 7.31 (d, J=9.0 Hz, 1H), 6.04 (m, 2H), 3.48 (m, 3H), 3.39 (s, 3H), 3.35 (m, 1H), 2.91 (m, 2H), 2.43 (m, 1H), 2.04 (m, 1H), 1.65 (m, 1H). 19F NMR (282 MHz, dDMSO) δ=−120.60 (d, J=14.4 Hz, 1F). LRMS (ESI) calculated for (M+H+) 476.20, found 476.33. Retention time (analytical HPLC)=17.85 min.

Example 2

Preparation of (S)-1-([1,1'-biphenyl]-4-ylmethyl)-7-(3-(aminomethyl)pyrrolidin-1-yl)-6-fluoro-8-methoxy-4-oxo-1,4-dihydroquinoline-3-carboxylic acid (UITT-III-217)

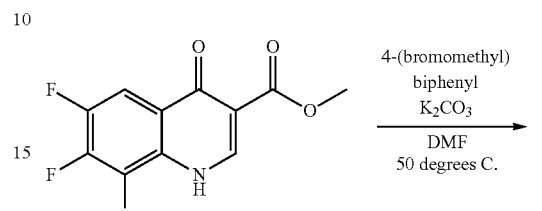

4

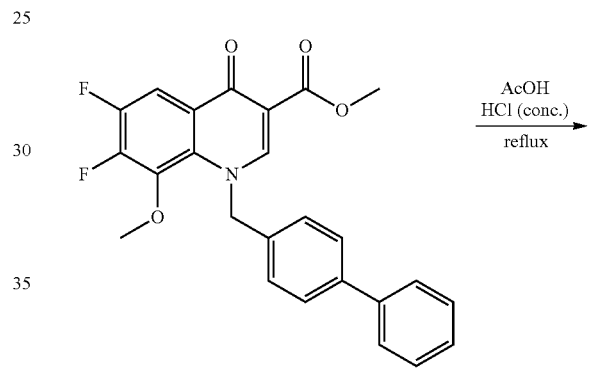

5

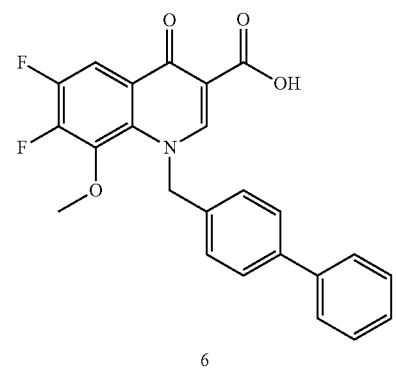

6

1. Boc—R aminomethyl pyrrolidine
TEA
DMSO
2. TFA

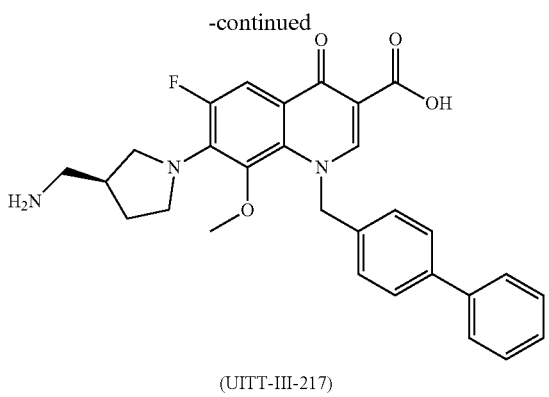

(UITT-III-217)

UITT-III-219 (19f) (56.6 mg, 0.138 mmol) was dissolved in 2:1 THF:1% LiOH in H₂O and stirred at room temperature for 1 h. The THF was removed by rotary evaporation and the aqueous layer was acidified to pH 1 with 4.0 N HCl. The aqueous layer was then extracted four times with 10 mL DCM and the combined organic layers were washed with brine, dried over Na₂SO₄, filtered, and concentrated by rotary evaporation. The residue was then dissolved in 1.5 mL anhydrous DMSO and heated to 50° C. with stirring. Boc-(R)-aminomethylpyrrolidine (61.6 mg, 0.308 mmol) and TEA (100 μL, 0.717 mmol) were added and the reaction stirred for 24 h. TFA (3 mL) was added and the reaction was allowed to cool to room temperature and stir overnight. The solution was then diluted with water and the product purified by preparatory HPLC. 89% yield over 3 steps. 1H NMR (300 MHz, dDMSO) δ=15.24 (bs, 1H), 9.13 (s, 1H), 7.96 (bs, 3H), 7.86 (m, 3H), 7.69 (m, 2H), 7.47 (m, 2H), 7.31 (d, J=9.0 Hz, 1H), 6.04 (m, 2H), 3.48 (m, 3H), 3.39 (s, 3H), 3.35 (m, 1H), 2.91 (m, 2H), 2.43 (m, 1H), 2.04 (m, 1H), 1.65 (m, 1H). 19F NMR (282 MHz, dDMSO) δ=−120.60 (d, J=14.4 Hz, 1F). LRMS (ESI) calculated for (M+H+) 476.20, found 476.33. Retention time (analytical HPLC)=17.85 min.

Compounds that can be synthesized by the methods described in Examples 1 and 2 include:

| Compound ID | Structure | Characterization |
|---|---|---|
| UIJD-II-175 | 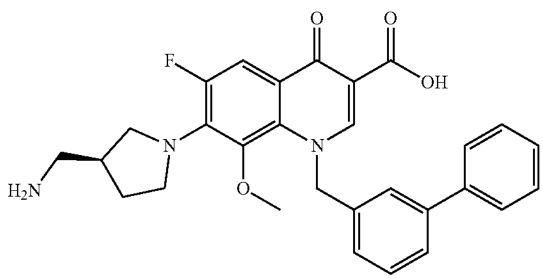 [SMILES: COc1c(N2CC[C@@H](CN)C2)c(F)cc2c(=O)c(C(=O)O)cn(Cc3cccc(-c4ccccc4)c3)c12] | ¹H NMR (400 MHz, DMSO) δ 9.10 (s, 1H), 7.69 (d, J = 13.9 Hz, 1H), 7.56 (dd, J = 11.5, 4.3 Hz, 4H), 7.45 (t, J = 7.6 Hz, 2H), 7.36 (t, J = 7.5 Hz, 2H), 7.04 (d, J = 7.7 Hz, 1H), 5.94 (dd, J = 29.7, 15.2 Hz, 2H), 5.21-5.06 (m, 3H), 4.73 (dd, J = 12.4, 5.7 Hz, 2H), 3.54-3.46 (m, 1H), 3.44 (s, 3H), 2.80-2.69 (m, 2H), 1.60 (dd, J = 12.1, 8.0 Hz, 1H). ¹⁹F NMR (300 MHz, CDCl₃) δ −121.36 (d, J = 13.9 Hz). ESI calculated (M + H)⁺ 502.21, found M + H = 502.21. Retention time (analytical HPLC) 25.5 min. |
| UIJD-II-115 | 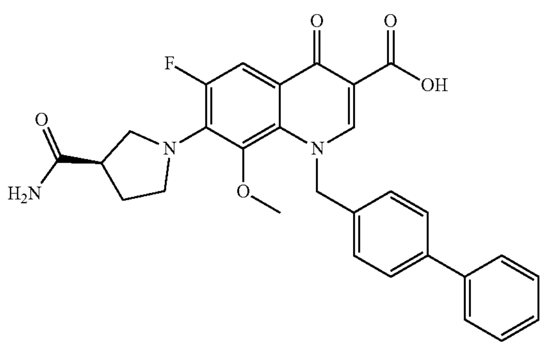 [SMILES: COc1c(N2CC[C@@H](C(N)=O)C2)c(F)cc2c(=O)c(C(=O)O)cn(Cc3ccc(-c4ccccc4)cc3)c12] | ¹H NMR (400 MHz, DMSO) δ 9.16-8.98 (m, 1H), 7.69 (d, J = 13.9 Hz, 1H), 7.61-7.57 (m, 3H), 7.47 (s, 1H), 7.42 (t, J = 7.5 Hz, 2H), 7.33 (t, J = 7.2 Hz, 1H), 7.23 (d, J = 8.2 Hz, 2H), 5.92 (dd, J = 30.0, 15.4 Hz, 2H), 3.69-3.61 (m, 1H), 3.51 (d, J = 8.2 Hz, 1H), 3.43 (d, J = 12.1 Hz, 3H), 3.11-3.02 (m, 1H), 2.98-2.89 (m, 1H), 2.10-1.95 (m, 1H), 1.17 (t, J = 7.1 Hz, 2H). ¹⁹F NMR (300 MHz, DMSO) δ −73.49 (d, J = 19.6 Hz), −120.57 (s). ESI calculated M + H⁺ = 516.19, found 516.2. RT = 19.7 min |
| UIJD-II-086 | 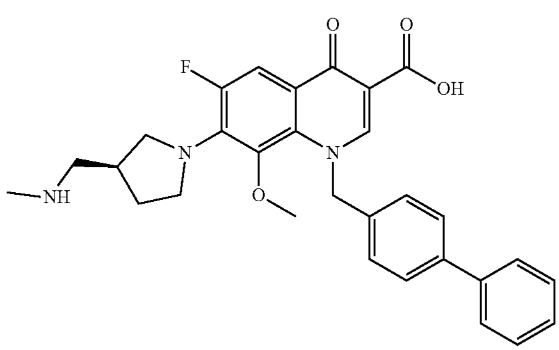 [SMILES: CNC[C@@H]1CCN(c2c(F)cc3c(=O)c(C(=O)O)cn(Cc4ccc(-c5ccccc5)cc4)c3c2OC)C1] | ¹H NMR (400 MHz, DMSO) δ 15.17 (s, 1H), 9.10 (s, 1H), 8.79 (s, 2H), 7.71 (d, J = 13.9 Hz, 1H), 7.60 (d, J = 8.2 Hz, 4H), 7.42 (t, J = 7.7 Hz, 2H), 7.33 (t, J = 7.3 Hz, 1H), 7.24 (d, J = 8.2 Hz, 2H), 5.93 (dd, J = 31.4, 15.3 Hz, 2H), 3.60 (t, J = 7.6 Hz, 1H), 3.52 (d, J = 8.0 Hz, 1H), 3.47 (s, 3H), 3.39 (d, J = 7.2 Hz, 3H), 2.99 (d, J = 6.4 Hz, 2H), 2.54 (t, J = 4.8 Hz, 3H), 2.14-2.02 (m, 1H), 1.71 (dd, J = 12.1, 8.0 Hz, 1H). ¹⁹F NMR (282 MHz, DMSO) δ −120.45 (d, J = 13.3 Hz). ESI calculated (M + H)⁺ 516.22, found 515.2298. Retention time (analytical HPLC) = 23.9 min |

| Compound ID | Structure | Characterization |
|---|---|---|
| UIJD-II-116 | 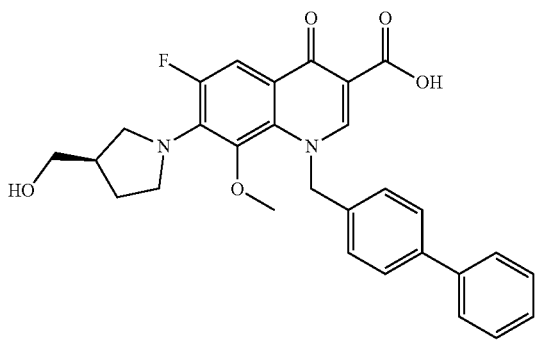 [SMILES: COc1c(N2CC[C@@H](CO)C2)c(F)cc2c(=O)c(C(=O)O)cn(Cc3ccc(-c4ccccc4)cc3)c12] | $^1$H NMR (400 MHz, DMSO) δ 9.10 (s, 1H), 7.70 (d, J = 14.0 Hz, 1H), 7.63-7.57 (m, 4H), 7.44 (dd, J = 10.3, 4.8 Hz, 2H), 7.38-7.32 (m, 1H), 7.25 (d, J = 8.3 Hz, 2H), 5.94 (dd, J = 30.9, 15.2 Hz, 2H), 3.52 (ddd, J = 11.6, 9.5, 4.2 Hz, 3H), 3.46 (s, 3H), 3.45-3.32 (m, 3H), 2.33 (dt, J = 14.5, 7.2 Hz, 1H), 1.96 (dt, J = 11.3, 5.8 Hz, 1H), 1.64 (dq, J = 12.2, 7.8 Hz, 1H). $^{19}$F NMR (400 MHz, DMSO) δ −120.50 (s). ESI calculated (M + H$^+$) 503.19, found 503.2. Retention time (analytical HPLC) = 21.7 min |
| UIJD-II-226 | 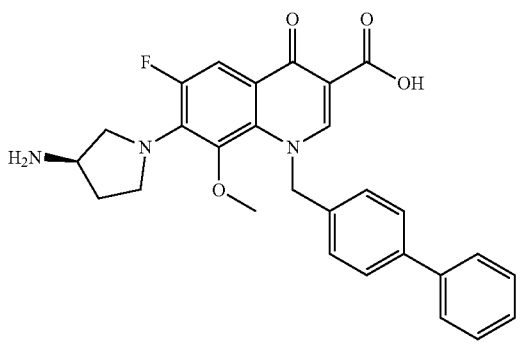 | 1H NMR (400 MHz, MeOD) d 8.97 (s, 1H), 7.77 (d, J = 13.6 Hz, 1H), 7.54 (d, J = 7.2 Hz, 4H), 7.38 (t, J = 7.3 Hz, 2H), 7.31 (dd, J = 13.6, 6.6 Hz, 1H), 7.24 (s, 2H), 5.89 (s, 2H), 4.09-3.81 (m, 2H), 3.74 (s, 2H), 3.56 (d, J = 9.3 Hz, 3H), 3.51 (dd, J = 12.6, 6.0 Hz, 1H), 2.41 (s, 1H), 2.10 (s, 1H). $^{19}$F NMR (300 MHz, DMSO) δ −120.22 (d, J = 12.7 Hz). Retention time (analytical HPLC): 19.82 min. ESI calculated (M + H)$^+$ 488.19, found M + H = 488.2. |
| UIJD-II-228 | 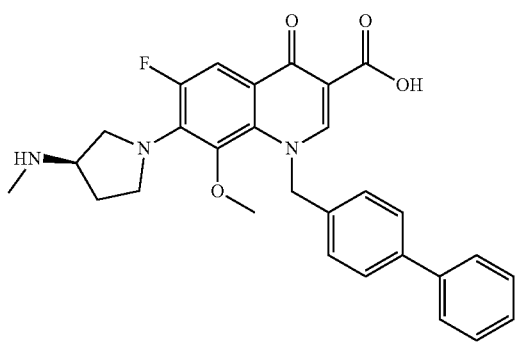 | $^1$H NMR (400 MHz, MeOD) δ 8.93 (s, 1H), 7.69 (d, J = 13.5 Hz, 1H), 7.53 (d, J = 7.9 Hz, 4H), 7.38 (t, J = 7.3 Hz, 2H), 7.28 (dd, J = 19.6, 12.4 Hz, 3H), 5.88 (s, 2H), 3.86 (d, J = 26.0 Hz, 2H), 3.73 (s, 3H), 3.55 (s, 3H), 2.75 (s, 3H), 2.44 (s, 1H), 2.16 (s, 1H). $^{19}$F NMR (300 MHz, DMSO) δ −121.37 (d, J = 13.4 Hz). Retention time (analytical HPLC): 20.668. ESI calculated (M + H)$^+$ 502.21, found 502.2. |
| UIJD-II-244 | 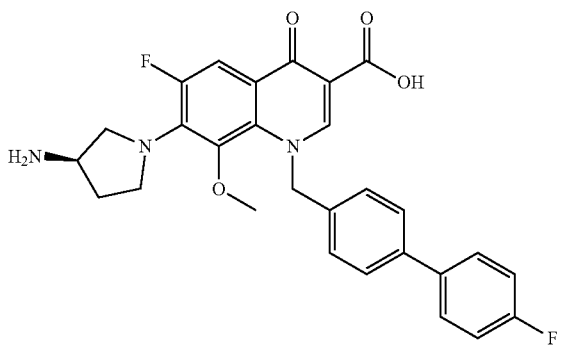 [SMILES: COc1c(N2CC[C@@H](N)C2)c(F)cc2c(=O)c(C(=O)O)cn(Cc3ccc(-c4ccc(F)cc4)cc3)c12] | $^1$H NMR (400 MHz, MeOD) δ 8.99 (s, 1H), 7.82 (d, J = 13.7 Hz, 1H), 7.56 (dd, J = 14.5, 8.8 Hz, 4H), 7.23 (d, J = 7.8 Hz, 2H), 7.13 (t, J = 8.7 Hz, 2H), 5.90 (s, 2H), 3.96 (d, J = 0.4 Hz, 1H), 3.86 (dd, J = 10.7, 5.6 Hz, 1H), 3.77-3.70 (m, 2H), 3.58 (s, 3H), 3.56-3.46 (m, 1H), 2.41 (dd, J = 13.1, 6.4 Hz, 1H), 2.07 (dd, J = 12.6, 5.9 Hz, 1H). $^{19}$F NMR (300 MHz, MeOD) δ −117.37--117.58 (m), −121.26 (d, J = 14.3 Hz).). Retention time (analytical HPLC): 20.678. ESI calculated (M + H)$^+$ 506.18, found 506.2. |

| Compound ID | Structure | Characterization |
|---|---|---|
| UIJD-II-264 | 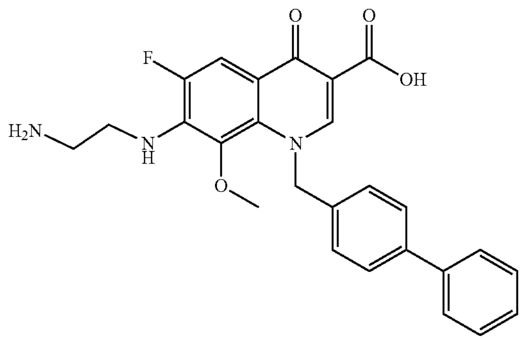 [SMILES: COc1c(NCCN)c(F)cc2c(=O)c(C(=O)O)cn(Cc3ccc(-c4ccccc4)cc3)c12] | $^1$H NMR (400 MHz, DMSO) δ 15.23 (s, 1H), 9.06 (s, 1H), 8.24 (s, 3H), 7.77 (d, J = 12.9 Hz, 1H), 7.59 (d, J = 8.2 Hz, 4H), 7.37 (dt, J = 35.8, 7.3 Hz, 3H), 7.18 (d, J = 8.2 Hz, 2H), 6.41 (t, J = 5.3 Hz, 1H), 5.93 (s, 2H), 3.71 (s, 3H), 3.65 (d, J = 5.9 Hz, 2H), 2.95 (d, J = 5.8 Hz, 2H). $^{19}$F NMR (300 MHz, DMSO) δ −126.65 (d, J = 12.9 Hz). Retention time (analytical HPLC) 18.77 min. ESI calculated (M + H)$^+$: 462.18, found 462.18. |
| UIJD-II-276B | 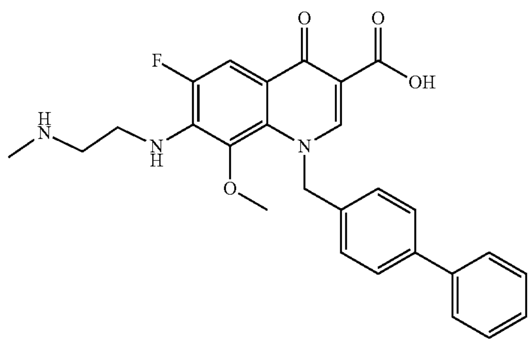 [SMILES: CNCCNc1c(F)cc2c(=O)c(C(=O)O)cn(Cc3ccc(-c4ccccc4)cc3)c2c1OC] | $^1$H NMR (400 MHz, DMSO) d 9.08 (s, 1H), 8.85 (s, 2H), 7.79 (d, J = 12.9 Hz, 1H), 7.59 (d, J = 8.1 Hz, 4H), 7.42 (t, J = 7.6 Hz, 2H), 7.34 (d, J = 7.4 Hz, 1H), 7.16 (d, J = 8.3 Hz, 2H), 6.40 (d, J = 5.4 Hz, 1H), 5.93 (s, 2H), 3.71 (s, 3H), 3.65 (d, J = 5.4 Hz, 2H), 3.05-2.97 (m, 2H), 2.47 (d, J = 5.4 Hz, 3H). $^{19}$F NMR (300 MHz, DMSO) δ −126.55 (d, J = 19.6 Hz). Retention time (analytical HPLC) 19.739 min. ESI calculated (M + H)$^+$: 476.19, found 476.19. |
| UIJD-II-275B | 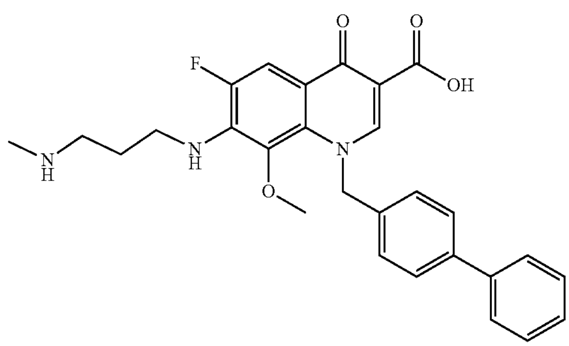 [SMILES: CNCCCNc1c(F)cc2c(=O)c(C(=O)O)cn(Cc3ccc(-c4ccccc4)cc3)c2c1OC] | $^1$H NMR (400 MHz, DMSO) δ 9.04 (s, 1H), 8.72 (s, 2H), 7.77 (d, J = 13.1 Hz, 1H), 7.59 (d, J = 8.2 Hz, 4H), 7.42 (t, J = 7.6 Hz, 2H), 7.33 (t, J = 7.3 Hz, 1H), 7.16 (d, J = 8.2 Hz, 2H), 6.46 (s, 1H), 5.93 (s, 2H), 3.68 (s, 3H), 3.42 (d, J = 2.1 Hz, 2H), 2.86-2.76 (m, 2H), 2.45 (t, J = 5.4 Hz, 3H), 1.83-1.75 (m, 2H). $^{19}$F NMR (282 MHz, CDCl$_3$) δ −127.30- −127.74 (m). Retention time (analytical HPLC) 20.23 min. ESI calculated (M + H)$^+$: 490.21, found 490.21. |
| UIJD-II-285B | 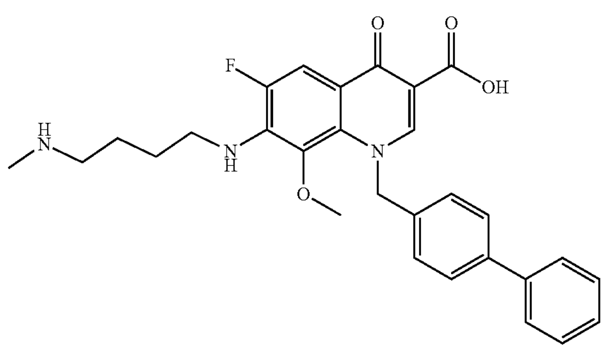 [SMILES: CNCCCCNc1c(F)cc2c(=O)c(C(=O)O)cn(Cc3ccc(-c4ccccc4)cc3)c2c1OC] | $^1$H NMR (400 MHz, DMSO) δ 9.05 (s, 1H), 8.82 (s, 2H), 7.75 (d, J = 13.0 Hz, 1H), 7.63-7.55 (m, 4H), 7.42 (dd, J = 10.4, 4.8 Hz, 2H), 7.33 (ddd, J = 7.3, 6.0, 1.0 Hz, 1H), 7.14 (d, J = 8.3 Hz, 2H), 6.40 (s, 1H), 5.92 (s, 2H), 3.66 (s, 3H), 3.33 (t, J = 5.5 Hz, 2H), 2.76-2.64 (m, 2H), 2.36 (t, J = 5.4 Hz, 3H), 1.53 (dt, J = 15.2, 7.6 Hz, 2H), 1.45-1.33 (m, 2H). $^{19}$F NMR (282 MHz, CDCl$_3$) δ −127.58-−127.83 (m). Retention time (analytical HPLC) 20.819. ESI calculated (M + H)$^+$: 504.22, found 504.22. |

Example 3

Fluoroquinolones are selective inhibitors of bacterial type II topoisomerases (DNA gyrase and topoisomerase IV) although a few of them have shown to inhibit human and other eukaryotic type II topoisomerases (topoisomerase II). Fluoroquinolones poisons type II topoisomerases and generate double strand breaks. No activity of fluoroquinolones against either type IA (topoisomerase III and bacterial topoisomerase I) or type IB (eukaryotic topoisomerase I) has been reported. As shown in Table 1, UITT-III-217 (217) and UITT-III-227 (227), exhibit higher activities against human topoisomerase II than bacterial type II topoisomerases.

TABLE 1

217 and 227 are effective against human topoisomerases

| Compound | DNA gyrase | Topo I (h/c) | Topo II |
|---|---|---|---|
| 217 | 1370 ± 10.1 | 26.0 ± 0.5/32.2 ± 0.01 | 127.6 ± 4.7 |
| 227 | >200 | 43.7 ± 0.6/66.6 ± 0.4 | 164.6 ± 20.2 |

The $IC_{50}$ values (the 50% inhibitory concentration, μM) of 217 and 227 against *E. coli* DNA gyrase, human/calf topoisomerase I, and human topoisomerase II were determined in the supercoiling, relaxation, and decatenation assays, respectively.

Further studies revealed that these fluoroquinolones are more active against human topoisomerase I, a type IB topoisomerase ($IC_{50}$ values of 217 and 227 in the relaxation assay are 26.5 μM and 43.1 μM, respectively), than human topoisomerase II ($IC_{50}$ values for 217 and 227 in the decatenation assay are 127.6 μM and 164.6 μM, respectively). Note that topoisomerase-targeting anticancer drugs achieve potent cell-based killing with modest (low to mid micromolar) inhibitory effects on the catalytic activity of topoisomerases in biochemical assays. For instance, the $IC_{50}$ value for the clinically-used etoposide is approximately 160 μM in the decatenation assay. These fluoroquinolones also inhibited bacterial topoisomerase I, a type IA topoisomerase, better than type II topoisomerases.

Several fluoroquinolone analogs of 217 and 227 described herein were synthesized by introducing a series of changes at the C-7 and C-8 positions, and determined that among these initial analogs, 217 and 227 exhibit the strongest inhibitory effects on both topoisomerases—even though the other compounds described herein show inhibitory effects on both topoisomerases. See Table 2.

TABLE 2

Activities of initial analogs of 217 and 227

| Compound | Topo I | Topo II |
|---|---|---|
| 217 | 26.0 ± 0.5 | 127.6 ± 4.7 |
| 205 | 44.4 ± 0.8 | 196.1 ± 22.4 |
| 207 | 54.2 ± 3.2 | 237.6 ± 15.2 |
| 215a | 25.9 ± 5.4 | 87.7 ± 7.0 |
| 227 | 43.7 ± 0.6 | 164.6 ± 20.2 |
| 213 | 127.9 ± 0.8 | 345.8 ± 34.9 |
| 215 | 132.2 ± 3.5 | 318.4 ± 21.1 |
| 213a | 59.0 ± 2.9 | 67.9 ± 3.3 |

*The $IC_{50}$ values (μM) against human topoisomerase I and human topoisomerase II were determined in the relaxation and decatenation assays, respectively.

wherein compounds 205, 207, 213, 213a, 215, and 215a have the following structures:

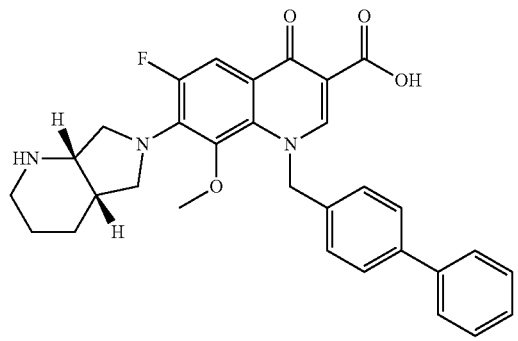

UITT-III-205 (205)

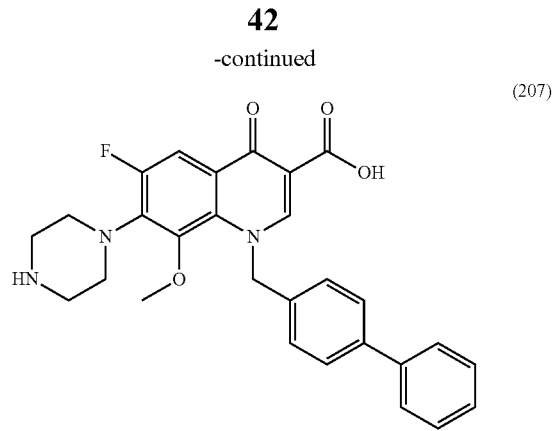

UITT-III-207 (207)

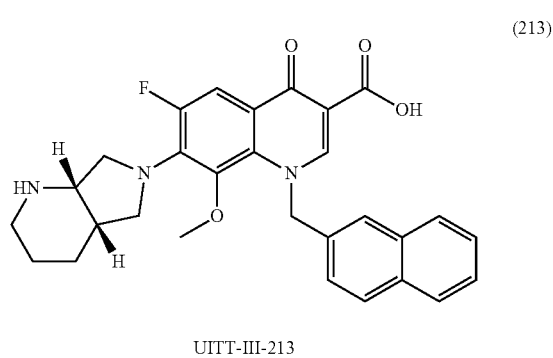

UITT-III-213 (213)

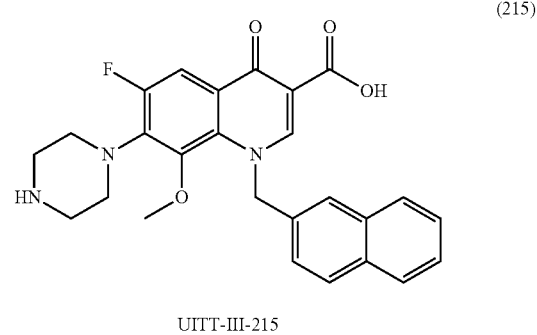

UITT-III-215 (215)

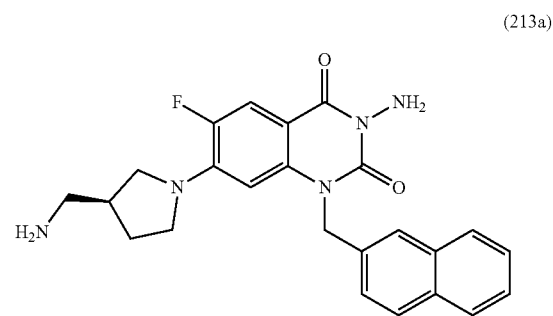

UITT-III-213a (213a)

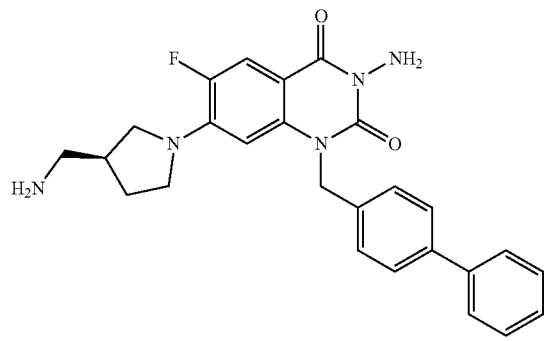

UITT-III-215a

Topoisomerase poisoning results in the accumulation of covalent topoisomerase-DNA complexes, which can be detected as the generation of nicked and/or linear DNA in DNA cleavage assays. Poisoning of human topoisomerase II generate double-strand breaks that lead to the development of therapy-related acute myeloid leukemia. DNA cleavage assays for human topoisomerase II with 217 and 227 did not detect any significant increase (two-fold or less) in the amounts of linear DNA (FIG. 1). Similarly, 217 and 227 did not poison mammalian topoisomerase I. Thus, 217 and 227 inhibit activity of, but do not poison either topoisomerase I or topoisomerase II.

In FIG. 1, the amounts of the full-length linear DNA were determined in the absence (100% cleavage) and the presence of various concentrations of either 217 (○) or 227 (●) in the DNA cleavage assay using two preparations of human topoisomerase II. A control topoisomerase II poison (5 or 10 μM etoposide) produced 400%-800% of linear DNA under the same condition.

Example 4

Alternative Synthetic Route to 217 and Analogs

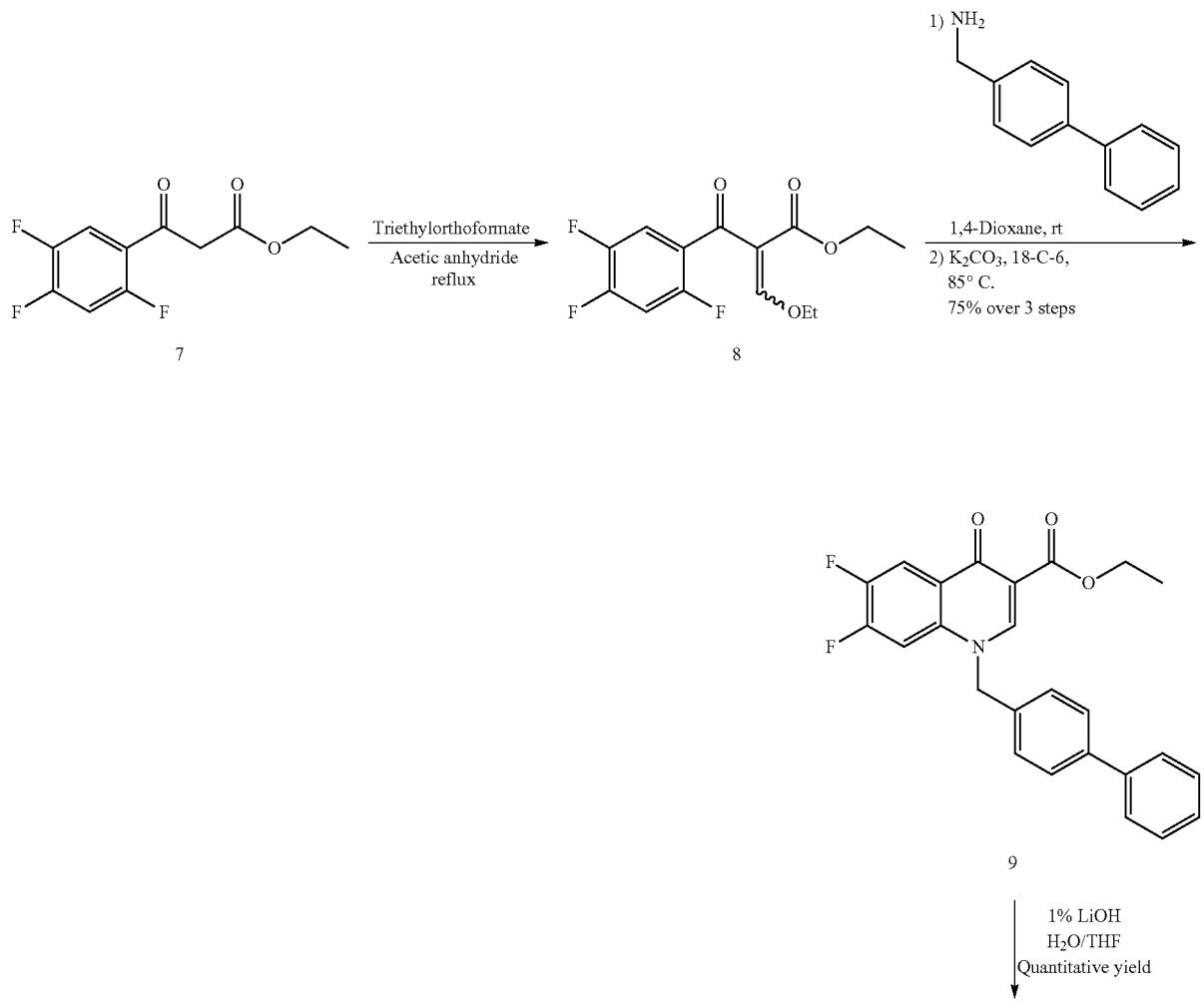

-continued

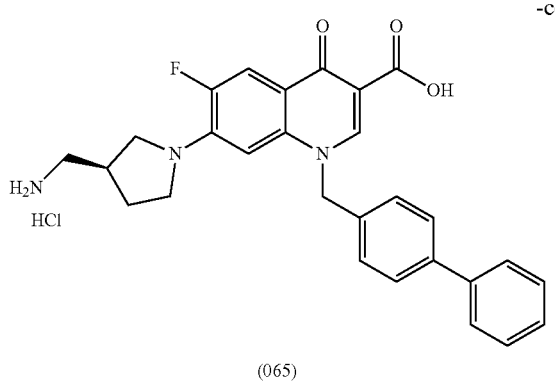

(065)

1) 3-N-Boc-aminomethyl pyrrolidine, DIPEA ACN, 50° C.
2) 4N HCl
77%

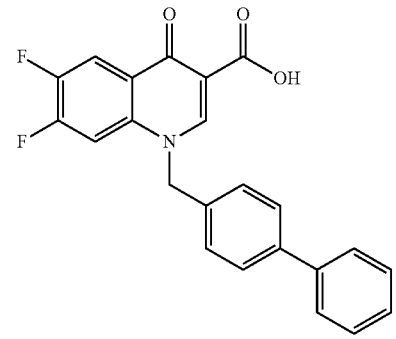

10

Commercially available ethyl 3-oxo-3-(2,4,5-trifluorophenyl)propanoate (7) (5.0 g, 20.31 mmol) was refluxed in triethylorthoformate (5.0 mL, 30.465 mmol) and acetic anhydride (5.8 mL, 60.93 mmol) for 4 h to yield enol ether 8. After the reaction was complete, the mixture was concentrated in vacuo and then dissolved in 1,4-dioxane (170 mL). 4-Phenylbenzylamine (3.5 g, 19.285 mmol) was added and the reaction stirred at room temperature for 6 h. $K_2CO_3$ (4.2 g, 30.465 mmol) and 18-crown-6 (1.0 g, 4.062 mmol) was added and the reaction was heated to 85° C. and stirred for an additional 2 h. The reaction mixture was then concentrated in vacuo and the resultant precipitate was washed with water and then purified by flash chromatography using a gradient starting with 1% MeOH in DCM and ending with 7% MeOH in DCM to give pure compound CK-III-195 (9). Yield=6.4 g, 75% over 3 steps.

CK-III-195 (9) (6.4 g, 15.259 mmol) was dissolved in 250 mL of 1:1 THF: 1% aqueous LiOH and stirred at room temperature for 24 h. The reaction was diluted with water and acidified to pH 1 with HCl. The aqueous layer was extracted three times with 300 mL DCM. The combined organic layers were washed with brine, dried over $Na_2SO_4$, filtered and concentrated in vacuo to give pure CK-III-197 (10) in quantitative yield.

CK-III-197 (10) (1.5 g, 3.833 mmol) was dissolved in 40 mL ACN to which was added Boc-(R)-aminomethylpyrrolidine (921.1 mg, 4.600 mmol) and DIPEA (1 mL, 5.750 mmol). The reaction was set to stir at 70° C. for 4 h. 25 mL 4N HCl was then added and the reaction was stirred for additional 12 h. The resultant precipitate was filtered and washed with ACN to give pure CK-II-065 (065). Yield 1.5 g, 77%. $^1$H NMR (300 MHz, DMSO) δ 15.61 (s, 1H, exchangeable), 9.19 (s, 1H), 8.16 (bs, 2H), 7.80 (d, J=14.3 Hz, 1H), 7.66 (dd, J=12.5, 7.9 Hz, 4H), 7.42 (m, 5H), 6.67 (d, J=7.5 Hz, 1H), 5.83 (s, 2H), 3.68 (m, 1H), 3.48 (m, 3H), 2.90 (m, 2H), 2.55 (m, 1H), 2.11 (m, 1H), 1.79 (m, 1H). $^{19}$F NMR (282 MHz, DMSO) δ -126.75 (s, 1F). HRMS (ESI) calculated for (M+H$^+$) 472.2031, found 472.2026. Retention time (analytical HPLC)=19.01 min.

Many other compounds can be accessed with this method, including the following compounds:

JD-II-292B

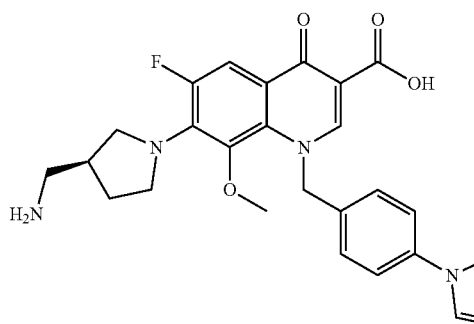

JD-II-294B

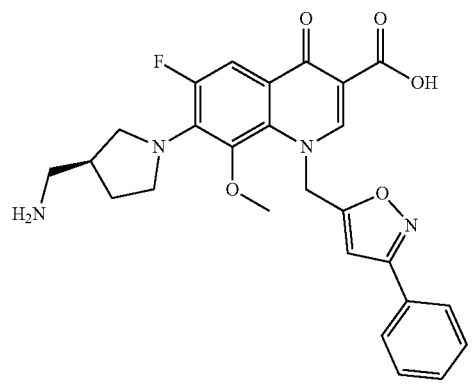

JD-II-290B

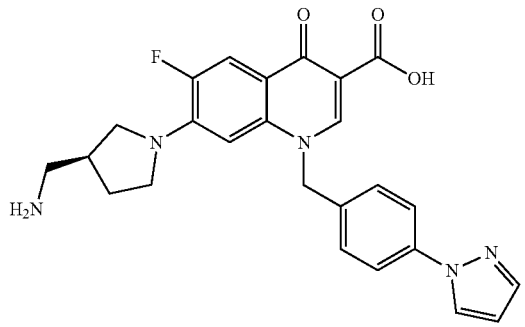

JD-II-286B
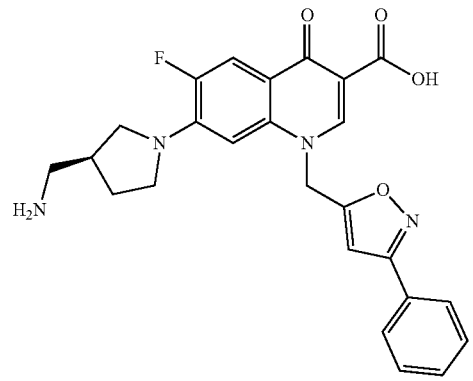
JD-III-067
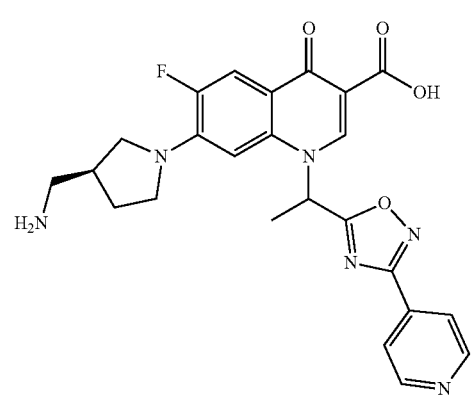
JD-02-299
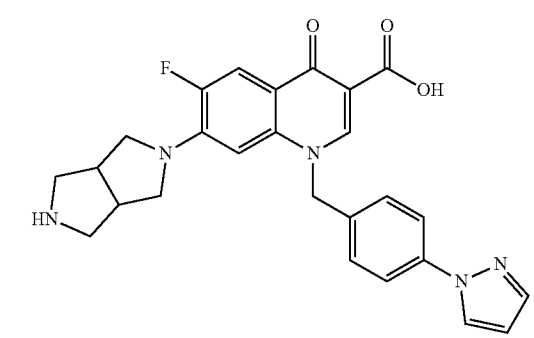
JD-II-302
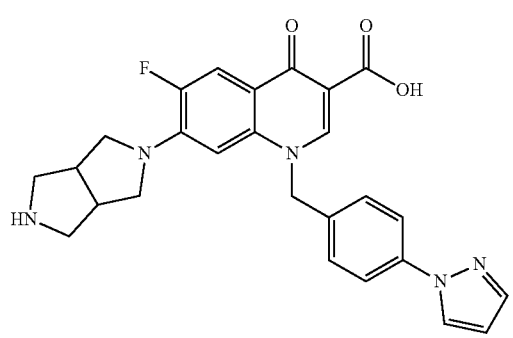
JD-II-298
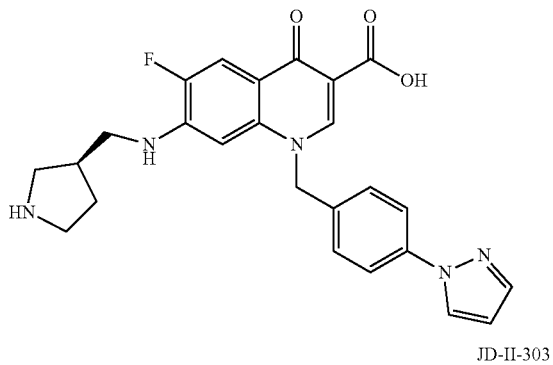
JD-II-303
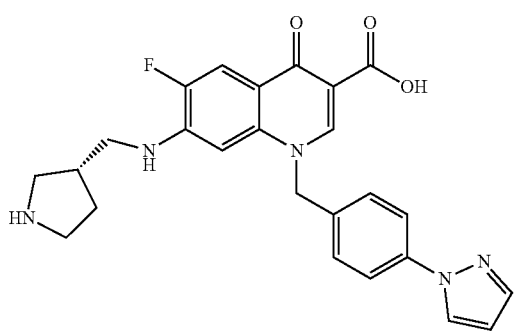
JD-II-304
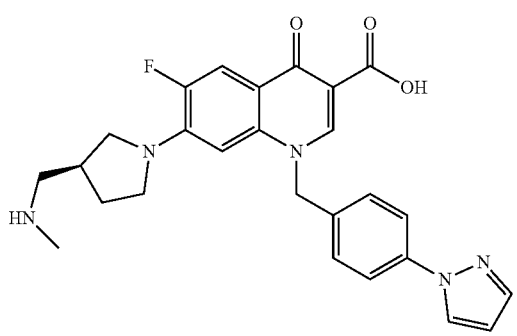
JD-II-300
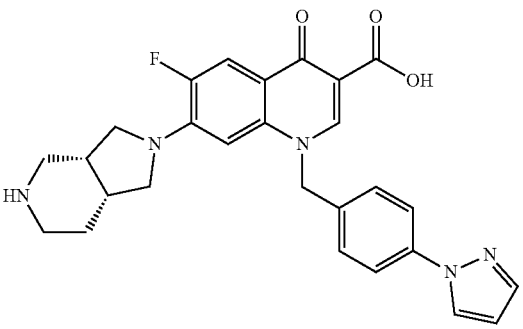

UICK-IV-089
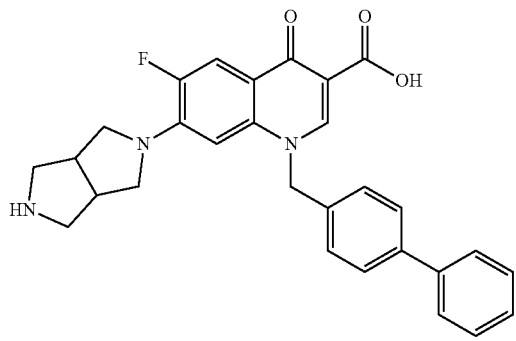
UICK-IV-095
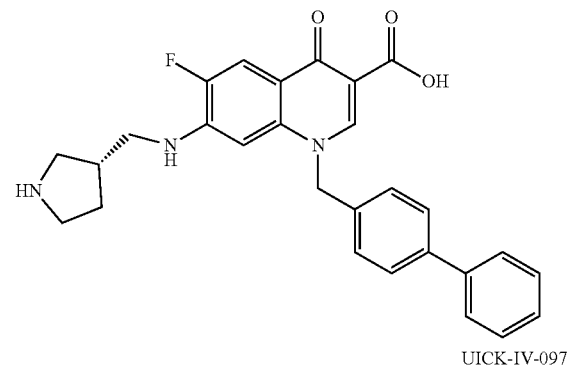
UICK-IV-091
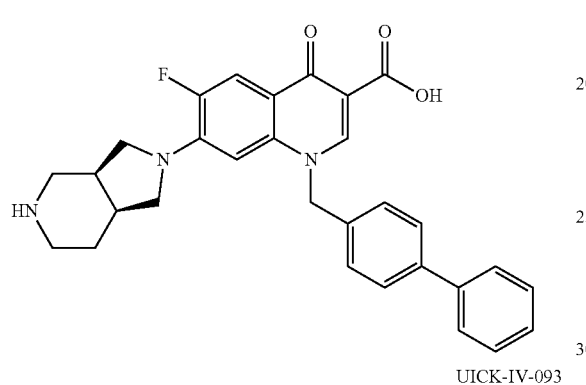
UICK-IV-097
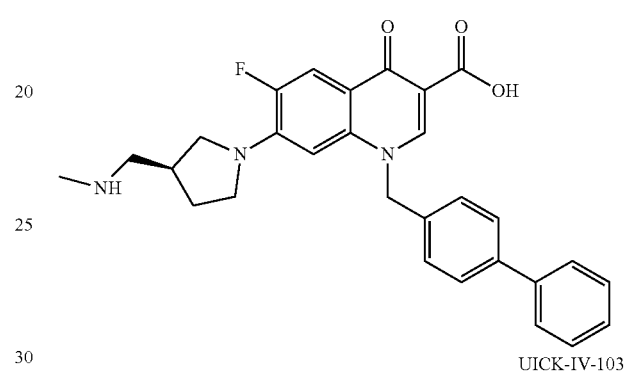
UICK-IV-093
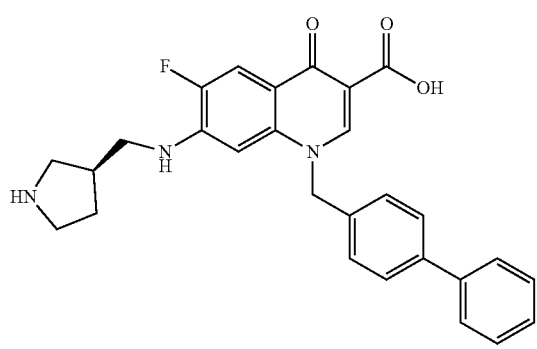
UICK-IV-103
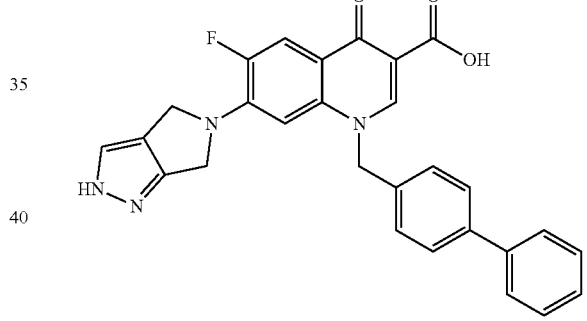
| Compound ID | Structure | Characterization |
|---|---|---|
| UIJD-II-281B | 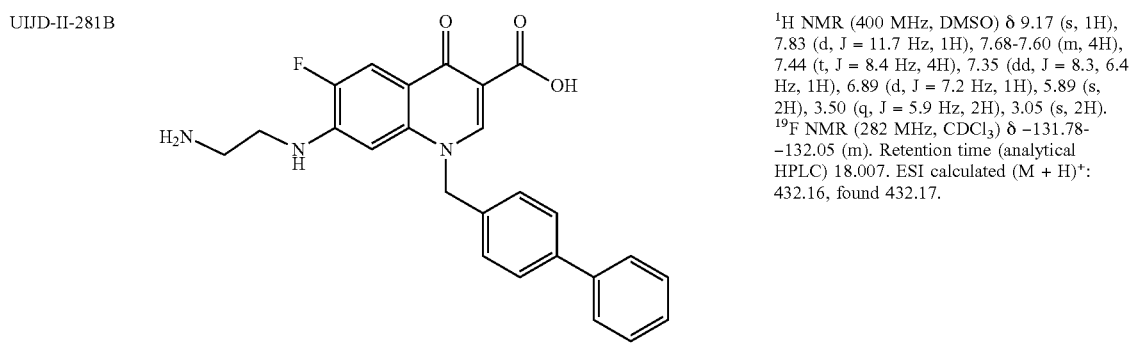 | $^1$H NMR (400 MHz, DMSO) δ 9.17 (s, 1H), 7.83 (d, J = 11.7 Hz, 1H), 7.68-7.60 (m, 4H), 7.44 (t, J = 8.4 Hz, 4H), 7.35 (dd, J = 8.3, 6.4 Hz, 1H), 6.89 (d, J = 7.2 Hz, 1H), 5.89 (s, 2H), 3.50 (q, J = 5.9 Hz, 2H), 3.05 (s, 2H). $^{19}$F NMR (282 MHz, CDCl$_3$) δ −131.78- −132.05 (m). Retention time (analytical HPLC) 18.007. ESI calculated (M + H)$^+$: 432.16, found 432.17. |

| Compound ID | Structure | Characterization |
|---|---|---|
| UIJD-II-282B | 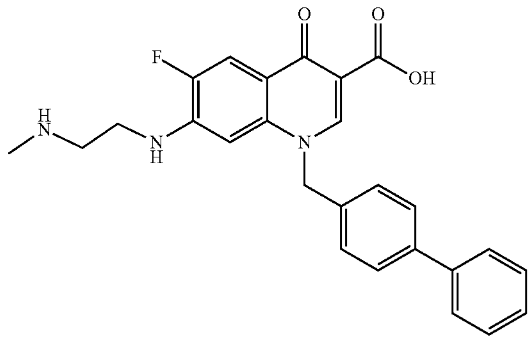 [SMILES: CNCCNc1cc2c(cc1F)c(=O)c(C(=O)O)cn2Cc1ccc(-c2ccccc2)cc1] | $^1$H NMR (400 MHz, DMSO) δ 15.61 (s, 1H), 9.16 (s, 1H), 8.87 (s, 2H), 7.83 (d, J = 11.7 Hz, 1H), 7.69-7.60 (m, 4H), 7.43 (dd, J = 8.0, 6.9 Hz, 4H), 7.34 (t, J = 7.3 Hz, 1H), 7.09 (d, J = 2.1 Hz, 1H), 6.91 (d, J = 7.2 Hz, 1H), 5.93 (s, 2H), 3.56 (dd, J = 11.6, 5.8 Hz, 2H), 2.96 (s, 2H), 2.47 (s, 3H). $^{19}$F NMR (282 MHz, CDCl$_3$) δ −131.68−−131.96 (m). Retention time (analytical HPLC) 18.748 min. ESI calculated (M + H)$^+$ 446.18, found 446.19. |
| UIJD-II-269B | 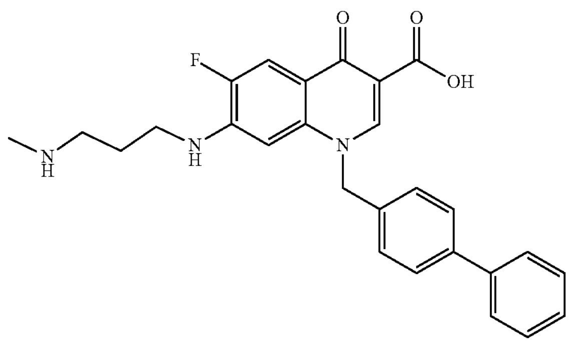 [SMILES: CNCCCNc1cc2c(cc1F)c(=O)c(C(=O)O)cn2Cc1ccc(-c2ccccc2)cc1] | $^1$H NMR (400 MHz, DMSO) δ 9.13 (s, 1H), 7.80 (d, J = 11.8 Hz, 1H), 7.69-7.61 (m, 4H), 7.47-7.40 (m, 4H), 7.34 (t, J = 7.3 Hz, 1H), 6.80 (d, J = 7.2 Hz, 1H), 5.87 (s, 2H), 3.30 (dd, J = 12.3, 6.2 Hz, 2H), 2.90-2.81 (m, 2H), 2.43 (t, J = 5.2 Hz, 3H), 1.80 (dd, J = 13.6, 7.0 Hz, 2H). $^{19}$F NMR (282 MHz, CDCl$_3$) δ −132.24−−132.45 (m). Retention time (analytical HPLC) 19.16 min. ESI calculated (M + H)$^+$ 460.20, found 460.20. |
| lp;2.4p UIJD-II-271B | | $^1$H NMR (400 MHz, DMSO) δ 9.15 (s, 1H), 7.79 (d, J = 11.9 Hz, 1H), 7.70 (d, J = 8.3 Hz, 2H), 7.67-7.62 (m, 2H), 7.45 (t, J = 7.6 Hz, 2H), 7.36 (dd, J = 9.6, 5.1 Hz, 3H), 6.65 (d, J = 7.2 Hz, 1H), 5.85 (s, 2H), 3.16 (dd, J = 12.6, 6.5 Hz, 2H), 2.61 (q, J = 12.7 Hz, 2H), 2.32 (t, J = 5.3 Hz, 3H), 1.55-1.46 (m, 2H), 1.34-1.25 (m, 2H). $^{19}$F NMR (282 MHz, CDCl$_3$) δ −132.46−−132.79 (m). Retention time (analytical HPLC) 19.5 min. ESI calculated (M + H)$^+$ 474.21, found 474.21. |
| UIJD-II-292B | 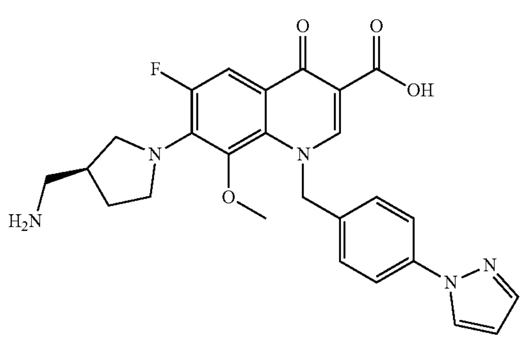 [SMILES: COc1c(N2CC[C@@H](CN)C2)c(F)cc2c(=O)c(C(=O)O)cn(Cc3ccc(-n4cccn4)cc3)c12] | $^1$H NMR (400 MHz, DMSO) δ 9.10 (s, 1H), 8.42 (d, J = 2.5 Hz, 1H), 7.75 (d, J = 8.6 Hz, 2H), 7.28 (d, J = 8.4 Hz, 3H), 6.50 (s, 2H), 5.93-5.84 (m, 2H), 3.62-3.54 (m, 3H), 3.46 (s, 3H), 3.36 m, 2H), 2.94-2.86 (m, 1H), 2.07 (m, 1H), 1.74-1.63 (m, 1H). $^{19}$F NMR (282 MHz, CDCl$_3$) δ −120.41−−120.57 (m). ESI calculated (M + H)$^+$ 492.2, found 492.2. Retention time (analytical HPLC) 16.9 min. |

| Compound ID | Structure | Characterization |
|---|---|---|
| UIJD-II-294B | 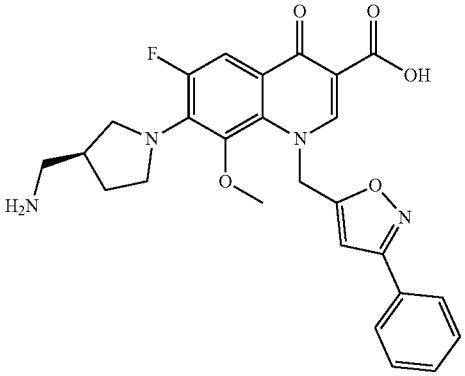 [SMILES: COc1c(N2CC[C@@H](CN)C2)c(F)cc2c(=O)c(C(=O)O)cn(Cc3cc(-c4ccccc4)no3)c12] | $^1$H NMR (400 MHz, DMSO) δ 9.07 (s, 1H), 7.81 (dd, J = 6.6, 2.9 Hz, 2H), 7.74 (d, J = 13.8 Hz, 1H), 7.49-7.42 (m, 3H), 7.01 (s, 1H), 6.13-6.00 (m, 2H), 3.63-3.44 (m, 5H), 3.41 (s, 3H), 2.96-2.83 (m, 2H), 2.07 (dd, J = 11.6, 5.3 Hz, 1H), 1.75-1.62 (m, 1H). $^{19}$F NMR (282 MHz, DMSO) δ −120.43−−120.63 (m). ESI calculated (M + H)$^+$ 493.18, found 493.19. Retention time (analytical HPLC) 18.2 min. |
| UIJD-II-290B | 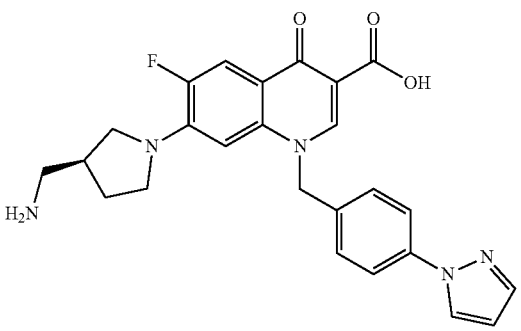 [SMILES: NC[C@@H]1CCN(c2cc3c(cc2F)c(=O)c(C(=O)O)cn3Cc2ccc(-n3cccn3)cc2)C1] | $^1$H NMR (400 MHz, DMSO) δ 9.16 (s, 1H), 8.47 (d, J = 2.5 Hz, 1H), 7.81 (m, 3H), 7.72 (d, J = 1.6 Hz, 1H), 7.48 (d, J = 8.6 Hz, 2H), 6.63 (d, J = 7.5 Hz, 1H), 6.54-6.49 (m, 1H), 5.80 (s, 2H), 3.70-3.63 (m, 2H), 3.46-3.36 (m, 3H), 2.92-2.85 (m, 2H), 2.11 (dd, J = 11.6, 5.3 Hz, 1H), 1.80-1.72 (m, 1H). $^{19}$F NMR (282 MHz, DMSO) δ −126.68−−127.19 (m). ESI calculated (M + H)$^+$ 462.19, found 462.19. Retention time (analytical HPLC) 15.7 min. |
| UIJD-II-286B | 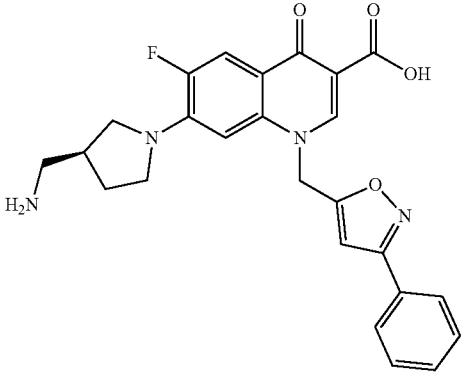 [SMILES: NC[C@@H]1CCN(c2cc3c(cc2F)c(=O)c(C(=O)O)cn3Cc2cc(-c3ccccc3)no2)C1] | $^1$H NMR (400 MHz, DMSO) δ 9.12 (s, 1H), 7.88-7.79 (m, 3H), 7.52-7.43 (m, 3H), 7.21 (s, 1H), 6.71 (d, J = 7.3 Hz, 1H), 6.07 (s, 2H), 3.75 (t, J = 7.2 Hz, 1H), 3.60 (s, 1H), 3.52 (dd, J = 16.8, 8.1 Hz, 1H), 2.95-2.85 (m, 2H), 2.61-2.52 (m, 1H), 2.14 (dd, J = 11.5, 5.1 Hz, 1H), 1.78 (dd, J = 12.4, 8.1 Hz, 1H). $^{19}$F NMR (282 MHz, CDCl$_3$) δ −126.57−−126.85 (m). ESI calculated (M + H)$^+$ 463.17, found 463.17. Retention time (analytical HPLC) 17.36. |

UICK-IV-093. $^1$H NMR (300 MHz, DMSO) δ 9.15 (s, 1H), 9.03 (bs, 1H, exchangeable), 7.82 (d, J=11.9 Hz, 1H), 7.67 (m, 4H), 7.42 (m, 5H), 7.22 (bs, 1H, exchangeable), 6.81 (d, J=7.1 Hz, 1H), 5.88 (s, 2H), 3.29 (m, 2H), 3.16 (m, 2H), 2.92 (m, 2H), 2.36 (m, 1H), 1.87 (m, 1H), 1.57 (m, 1H). $^{19}$F NMR (282 MHz, DMSO) δ −132.24 (s, 1F). HRMS (ESI) calculated for (M+H$^+$) 472.2031, found 472.1980. Retention time (analytical HPLC)=19.08 min.

UICK-IV-095. $^1$H NMR (300 MHz, DMSO) δ 9.15 (s, 1H), 8.97 (bs, 1H, exchangeable), 7.82 (d, J=11.9 Hz, 1H), 7.67 (m, 4H), 7.39 (m, 5H), 7.21 (bs, 1H, exchangeable), 6.81 (d, J=7.2 Hz, 1H), 5.88 (s, 2H), 3.28 (m, 2H), 3.17 (m, 2H), 2.92 (m, 2H), 2.34 (m, 1H), 1.85 (m, 1H), 1.57 (m, 1H). $^{19}$F NMR (282 MHz, DMSO) −132.26 (s, 1F). HRMS (ESI) calculated for (M+H$^+$) 472.2031, found 472.2005. Retention time (analytical HPLC)=19.10 min Example 5

The compounds listed in the table below were synthesized using methods that are effectively modified versions of the methods described in Examples 1, 2, and 4.

| Compound ID | Structure | Characterization |
|---|---|---|
| UIJD-II-215B | 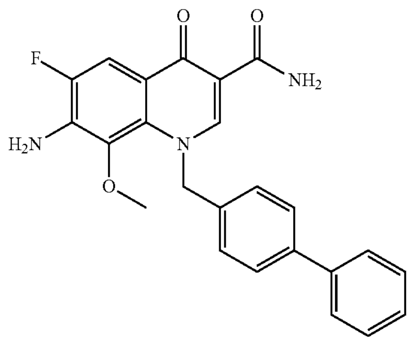 | ¹H NMR (300 MHz, Acetone) δ 9.78 (d, J = 4.9 Hz, 1H), 8.82 (s, 1H), 7.70 (d, J = 13.4 Hz, 1H), 7.62-7.57 (m, 4H), 7.43 (t, J = 7.4 Hz, 2H), 7.33 (t, J = 7.3 Hz, 1H), 7.14 (d, J = 8.2 Hz, 2H), 5.85 (s, 2H), 3.64 (s, 3H), 3.44 (s, 1H), 2.97 (t, J = 4.4 Hz, 3H), 2.85 (d, J = 4.8 Hz, 3H). ¹⁹F NMR (300 MHz, DMSO) δ −129.73−−130.14 (m). Retention time (analytic HPLC): 21.8 min. ESI calculated (M + Na)⁺ 468.18, found (M + Na)⁺ 468.16 |
| UIJD-II-237 UIJD-II-224 | | ¹H NMR (400 MHz, MeOD) δ 8.96 (s, 1H), 7.77 (d, J = 14.1 Hz, 1H), 7.60-7.52 (m, 4H), 7.44-7.36 (m, 2H), 7.34-7.27 (m, 1H), 7.23 (d, J = 8.3 Hz, 2H), 5.87 (dd, J = 63.8, 15.4 Hz, 2H), 3.92 (s, 3H), 3.71-3.63 (m, 2H), 3.53 (ddd, J = 7.3, 6.6, 3.6 Hz, 1H), 3.50 (s, 3H), 3.46 (ddd, J = 10.5, 5.9, 1.8 Hz, 1H), 3.07 (d, J = 7.2 Hz, 2H), 2.55 (dt, J = 11.0, 5.5 Hz, 1H), 2.25-2.16 (m, 1H), 1.74 (dq, J = 16.6, 8.2 Hz, 1H). ¹⁹F NMR (300 MHz, CDCl₃) δ −121.79−−122.05 (m). Retention time (analytical HPLC) 19.7. ESI calculated (M + H)⁺: 516.22, found 516.2. |
| UIJD-II-251 | 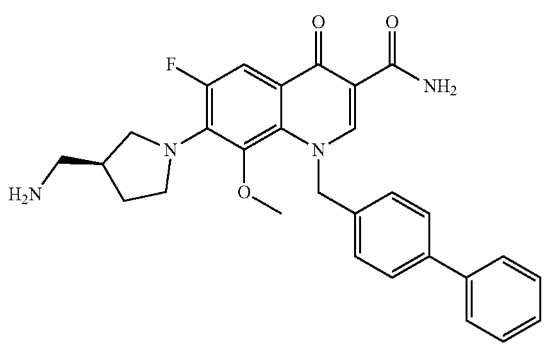 [SMILES: COc1c(N2CC[C@@H](CN)C2)c(F)cc2c(=O)c(C(N)=O)cn(Cc3ccc(-c4ccccc4)cc3)c12] | ¹H NMR (300 MHz, CDCl₃) δ 8.90 (s, 1H), 7.68 (d, J = 14.0 Hz, 1H), 7.59 (t, J = 10.0 Hz, 4H), 7.47-7.29 (m, 3H), 7.23 (d, J = 8.1 Hz, 2H), 5.86 (q, J = 15.3 Hz, 2H), 4.51 (s, 1H), 3.57 (dd, J = 13.4, 5.7 Hz, 2H), 3.47 (s, 3H), 3.37 (dd, J = 15.2, 9.0 Hz, 2H), 2.90 (s, 2H), 2.09 (dd, J = 10.6, 4.3 Hz, 1H), 1.75-1.66 (m, 1H). ¹⁹F NMR (300 MHz, DMSO) δ −122.44 (d, J = 13.6 Hz). Retention time (analytical HPLC) 17.438 min. ESI calculated (M + H)⁺: 501.22, found 501.23. |
| UIJD-II-242 | 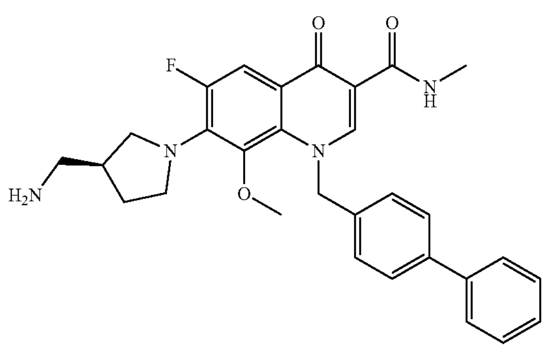 [SMILES: CNC(=O)c1cn(Cc2ccc(-c3ccccc3)cc2)c2c(OC)c(N3CC[C@@H](CN)C3)c(F)cc2c1=O] | ¹H NMR (400 MHz, MeOD) δ 8.94 (s, 1H), 7.76 (d, J = 14.1 Hz, 1H), 7.57-7.49 (m, 4H), 7.41-7.35 (m, 2H), 7.32-7.27 (m, 1H), 7.22 (d, J = 8.3 Hz, 2H), 5.87 (dd, J = 67.3, 15.5 Hz, 2H), 3.69 (ddd, J = 9.4, 8.0, 4.0 Hz, 2H), 3.55-3.50 (m, 1H), 3.48 (d, J = 8.0 Hz, 3H), 3.46-3.40 (m, 1H), 3.10-3.04 (m, 2H), 2.98 (s, 3H), 2.57 (dt, J = 14.5, 7.3 Hz, 1H), 2.21 (dt, J = 10.7, 6.7 Hz, 1H), 1.75 (dq, J = 12.2, 8.3 Hz, 1H). ¹⁹F NMR (282 MHz, MeOD) δ −122.16 (d, J = 14.7 Hz). Retention time (analytical HPLC): 18.45. ESI calculate (M + H)⁺ 515.24, found 515.2. |

| Compound ID | Structure | Characterization |
|---|---|---|
| UIJD-II-246 | 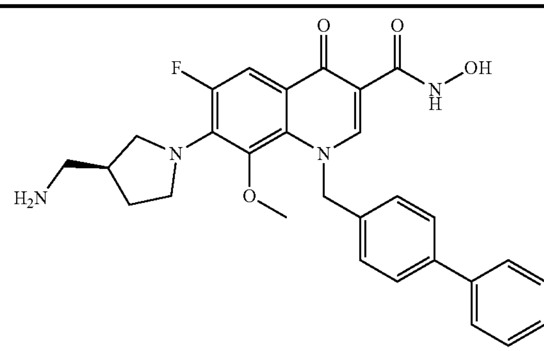 | $^1$H NMR (300 MHz, DMSO) δ 11.66 (s, 1H), 8.90 (s, 1H), 7.68 (d, J = 14.1 Hz, 1H), 7.61 (d, J = 8.3 Hz, 4H), 7.43 (t, J = 7.5 Hz, 2H), 7.35 (d, J = 7.3 Hz, 1H), 7.22 (d, J = 8.2 Hz, 2H), 5.89 (q, J = 15.6 Hz, 2H), 3.62-3.53 (m, 3H), 3.48 (s, 3H), 3.43-3.31 (m, 2H), 2.98-2.84 (m, 2H), 2.08 (dd, J = 7.8, 4.7 Hz, 1H), 1.76-1.67 (m, 1H). $^{19}$F NMR (300 MHz, DMSO) δ −121.96−−122.25 (m). Retention time (analytical HPLC): 21.8 min. ESI calculated (M + H)$^+$ 517.22, found 517.22. |

Example 6

Both 217 and 227 were submitted to the NCI for the 60 DTP Human Tumor Cell Line Screen. The single dose (10 µM) screening showed significant growth inhibition for 217 and 227 (mean growth of 40.3% and 44.1%, respectively), and the further evaluation of their activities has determined the mean GI$_{50}$ value of 217 and 227 to be 1.9 µM and 3.1 µM, respectively, against the 60 cancer cell lines used in the screen. Comparison (NCI's COMPARE program) of GI$_{50}$ and LD$_{50}$ values has demonstrated that both 217 and 227 are significantly more effective than etoposide against the majority of the 60 cancer cell lines tested. Although these compounds were active against all 60 cancer cell lines, the strongest growth inhibition was seen in leukemia and colon cancer panels.

Example 7

Figure 2:
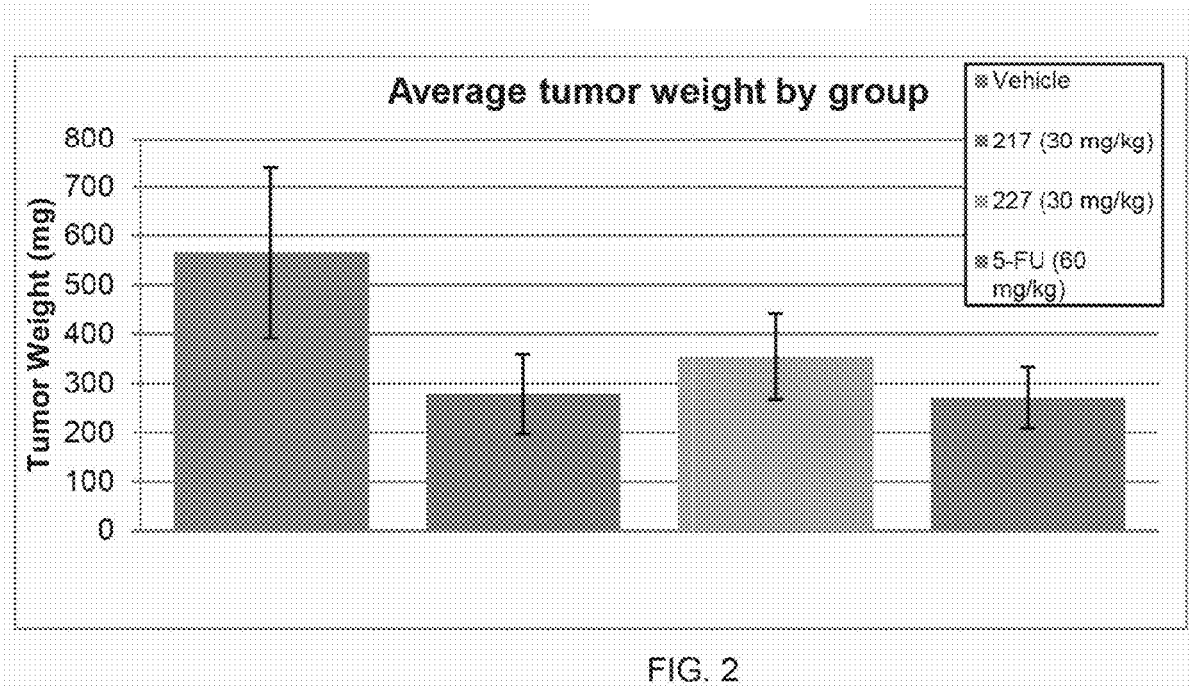
FIG. 2 is a plot of average tumor weight after a 3-week treatment with the compounds "217" and "227."

In vivo toxicity studies were performed to establish the maximum tolerated dose of 217 and 227 in mice. The daily intraperitoneal administration of 217 and 227 at up to 30 mg/kg for 3 weeks was well-tolerated and did not have any significant effect on animal weight gain. Higher doses could not be used due to the limited aqueous solubility of 217 and 227. A proof of concept efficacy study was also conducted in mice with 217 and 227. Based on the in vitro susceptibility to 217 and 227, and the availability of the established xenograft models, a colon cancer (HT-29) xenograft model was used. 217 inhibited the proliferation of colon cancer in vivo as well as 5-FU (FIG. 2). 227 exhibited activity but was not as effective as 217 in this xenograft model. These results suggested that at least 217 might serve as a lead compound for the successful development of novel anticancer agents against colon cancer. The maximum doses used in the efficacy studies were limited by the compounds' solubility, not their toxicity, suggesting that modifying the 217 or 227 formulations and/or developing analogs with improved aqueous solubility could lead to fluoroquinolones with even better anticancer activity while retaining an improved safety profile.

Example 8

An MTT assay was performed with 277 and with the following compounds:

(086)

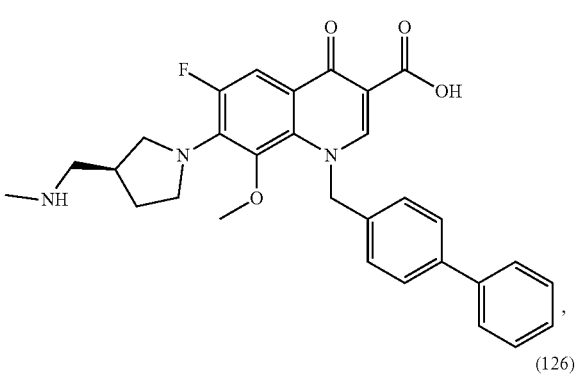

(126)

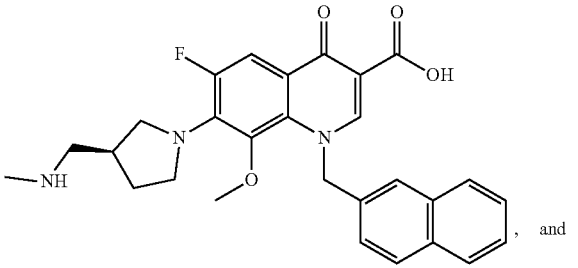

, and (065)

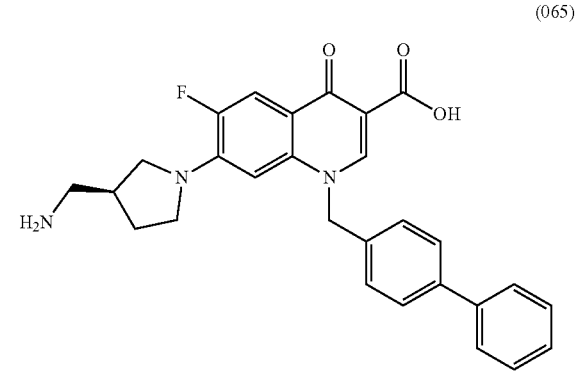

against colon (HT-29) and leukemia (K-562) cell lines to determine their in vitro anti-proliferative activities. The anti-proliferative activity of 086, 126, and 227 was similar to that of 217, whereas the anti-proliferative activity of 065 was higher, roughly 2-5 fold higher than that of 217.

The following Embodiments are encompassed by the instant disclosure:

Embodiment 1 relates to a compound of the formula (I):

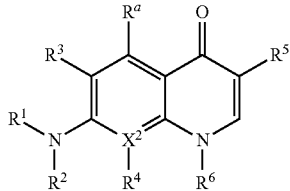

(I)

or a pharmaceutically acceptable salt, polymorph, prodrug, solvate or clathrate thereof, wherein:

$R^a$ is halo, nitro, cyano, optionally substituted alkyl, optionally substituted alkoxy, optionally substituted aryl, optionally substituted aryloxy, optionally substituted heteroaryl, or $NR^{a'}R^{a''}$ wherein $R^{a'}$ and $R^{a''}$ are each, independently, H or optionally substituted alkyl;

$R^1$ and $R^2$ are each independently H, optionally substituted alkyl, optionally substituted aryl, optionally substituted arylalkyl or $R^1$ and $R^2$, together with the nitrogen atom to which they are attached, form an optionally substituted heterocyclyl group;

$R^3$ is H or halo;

$R^4$ is H, halo, optionally substituted alkyl or optionally substituted alkoxy, but $R^4$ is absent if $X^2$ is N;

$X^2$ is N or C;

$R^5$ is H, OH, optionally substituted alkoxy, —C(O)R$^{5'}$ (wherein $R^{5'}$ is H, OH, optionally substituted alkyl, optionally substituted aryl, optionally substituted alkoxy or —N(R$^{5''}$)$_2$, wherein each $R^{5''}$ is, independently, H, OH, optionally substituted alkoxy, optionally substituted alkyl or optionally substituted arylalkyl) or —N(R$^{5''}$)$_2$; and $R^6$ is the group -L-R$^{6'}$, wherein L is a linker group and R$^{6'}$ is a group having sufficient "steric bulk" such that the compound of the formula (I) is (a) not a topoisomerase II poison, (b) inhibits topoisomerase I and topoisomerase II and/or (c) inhibits topoisomerase I to a greater extent than topoisomerase II.

Embodiment 2 relates to the compound of Embodiment 1, wherein the compound of the formula (I) is a compound of the formula (Ia):

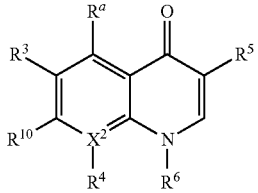

(Ia)

or a pharmaceutically acceptable salt, polymorph, prodrug, solvate or clathrate thereof, wherein:

$X^2$, $R^a$, $R^3$, $R^4$, $R^5$, and $R^6$ are as defined for compounds of the formula (I); and $R^{10}$ is aryl,

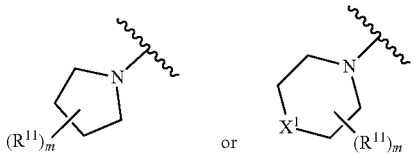

wherein each $R^{11}$ is H, —N(R$^{5''}$)$_2$, C(O)N(R)$_2$ (wherein each R group is, independently, hydrogen, alkyl, acyl, cycloalkyl, aryl, aralkyl, heterocyclyl, heteroaryl, or heteroarylalkyl), optionally substituted alkyl or two adjacent $R^{11}$ groups, together with the atoms to which they are attached form an optionally substituted cycloalkyl group or an optionally substituted heterocylcyl group; m is an integer from 1 to 3; and $X^1$ is O or NR$^{12}$, wherein $R^{12}$ is H or optionally substituted alkyl or $R^{12}$ and an adjacent $R^{11}$ group, together with the atoms to which they are attached, form an optionally substituted heterocyclyl group.

Embodiment 3 relates to the compound of Embodiment 1, wherein the compound of the formula (I) is a compound of the formula (Ib):

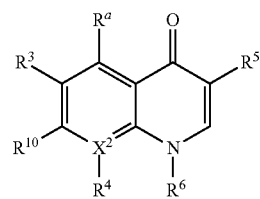

(Ib)

or a pharmaceutically acceptable salt, polymorph, prodrug, solvate or clathrate thereof, wherein:

$R^a$ is optionally substituted alkyl or NH$_2$;

$X^2$, $R^3$, $R^4$, and $R^5$ are as defined for compounds of the formula (I);

$R^6$ is —(CH$_2$)$_n$—R$^{6''}$ or —C(O)R$^{6''}$ wherein n is an integer from 1 to 3 (e.g., 1) and R$^{6''}$ is an aryl or heteroaryl group.

Embodiment 4 relates to the compound of Embodiment 3, wherein R$^{6''}$ is:

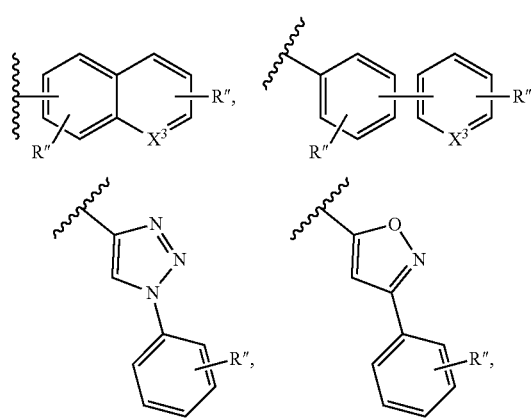

-continued

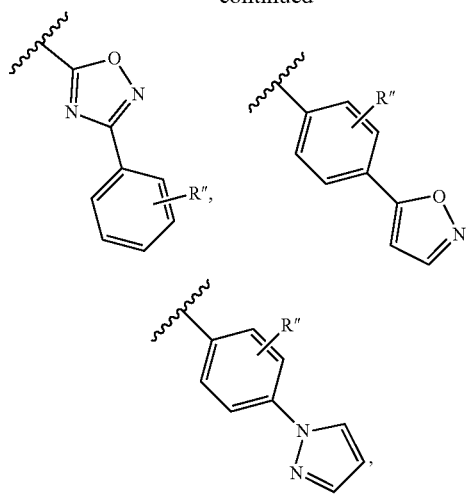

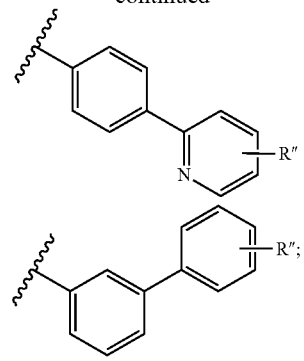

or wherein each R'' is, independently H or halo and $X^3$ is N or CH; and $R^{10}$ is aryl,

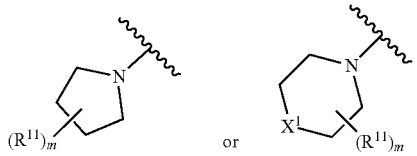

wherein each $R^{11}$ is H, C(O)N(R)$_2$ (wherein each R group is, independently, hydrogen, alkyl, acyl, cycloalkyl, aryl, aralkyl, heterocyclyl, heteroaryl, or heteroarylalkyl), optionally substituted alkyl or two adjacent $R^{11}$ groups, together with the atoms to which they are attached form an optionally substituted cycloalkyl group or an optionally substituted heterocylcyl group; m is an integer from 1 to 3; and $X^1$ is O or $NR^{12}$, wherein $R^{12}$ is H or optionally substituted alkyl or $R^{12}$ and an adjacent $R^{11}$ group, together with the atoms to which they are attached, form an optionally substituted heterocyclyl group.

Embodiment 5 relates to the compound of Embodiment 3, wherein $R^{6''}$ is:

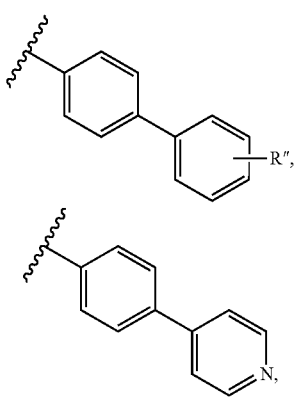

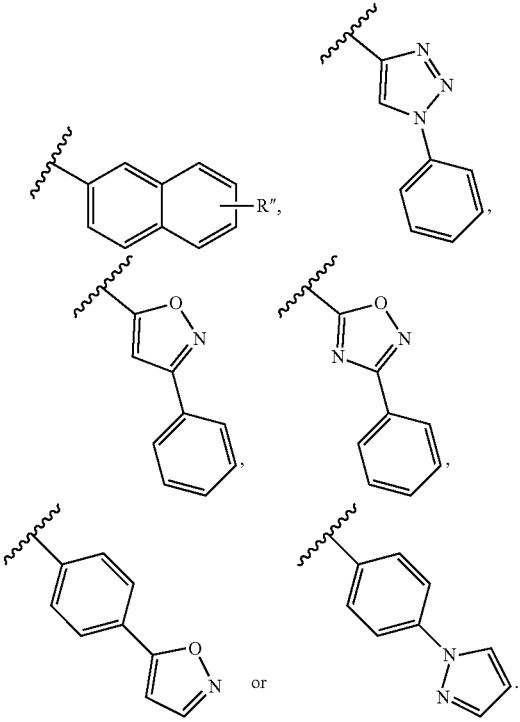

or

Embodiment 6 relates to a compound of the formula (II):

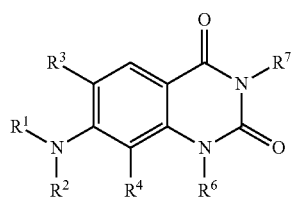

(II)

or a pharmaceutically acceptable salt, polymorph, prodrug, solvate or clathrate thereof, wherein:
$R^1$—$R^4$ and $R^6$ are as defined for compounds of the formula (I); and
$R^7$ is H, OH, optionally substituted alkoxy, optionally substituted alkyl or $NR^8R^9$, wherein $R^8$ and $R^9$ are each independently H, optionally substituted alkyl, optionally substituted aryl or optionally substituted arylalkyl.

Embodiment 7 relates to the compound of Embodiment 6, wherein the compound of the formula (II) is a compound of the formula (IIa):

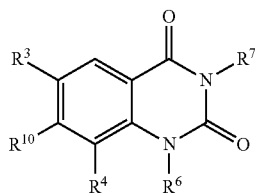

(IIa)

or a pharmaceutically acceptable salt, polymorph, prodrug, solvate or clathrate thereof, wherein:
$R^3$, $R^4$, and $R^6$ are as defined for compounds of the formula (I);
$R^7$ is H, optionally substituted alkyl or $NR^8R^9$, wherein $R^8$ and $R^9$ are each independently H, optionally substituted alkyl, optionally substituted aryl or optionally substituted arylalkyl; and
$R^{10}$ is aryl,

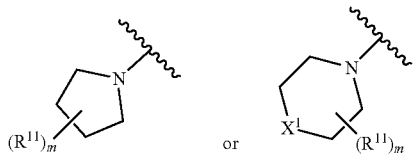

wherein each $R^{11}$ is H, $C(O)N(R)_2$ (wherein each R group is, independently, hydrogen, alkyl, acyl, cycloalkyl, aryl, aralkyl, heterocyclyl, heteroaryl, or heteroarylalkyl), optionally substituted alkyl or two adjacent $R^{11}$ groups, together with the atoms to which they are attached form an optionally substituted cycloalkyl group or an optionally substituted heterocylcyl group; m is an integer from 1 to 3; and $X^1$ is O or $NR^{12}$, wherein $R^{12}$ is H or optionally substituted alkyl or $R^{12}$ and an adjacent $R^{11}$ group, together with the atoms to which they are attached, form an optionally substituted heterocyclyl group.

Embodiment 8 relates to a compound of the formula (III) and (IV):

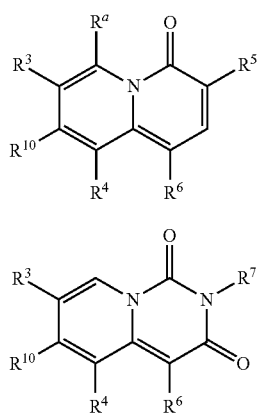

wherein the groups $R^a$, $R^3$—$R^7$, and $R^{10}$ are as defined in Embodiments 1-7.

Embodiment 9 relates to a compound of any one of Embodiments 1-8, wherein $R^3$ is halo.

Embodiment 10 relates to a compound of any one of Embodiments 1-8, wherein $R^3$ is H.

Embodiment 11 relates to a compound of any one of Embodiments 1-9, wherein $R^4$ is alkoxy.

Embodiment 12 relates to a compound of any one of Embodiments 1-9, wherein $R^4$ is H.

Embodiment 13 relates to a compound of any one of Embodiments 1-12, wherein $R^5$ is —$C(O)R^{5'}$.

Embodiment 14 relates to a compound of any one of Embodiments 1-12, wherein $R^6$ is optionally substituted arylalkyl.

Embodiment 15 relates to a compound of Embodiment 6 or 7, wherein $R^7$ is $NR^8R^9$.

Embodiment 16 relates to a compound as in any one of Embodiments 1-15, wherein when $R^6$ is:

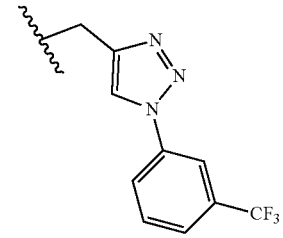 [SMILES: *Cc1cn(-c2cccc(C(F)(F)F)c2)nn1]

$R^1$ and $R^2$, together with the nitrogen atom to which they are attached, form an optionally substituted pyrrolidinyl group.

Embodiment 17 relates to a compound of any one of Embodiments 1-16, wherein $R^{11}$ is optionally substituted alkyl.

Embodiment 18 relates to a compound of any one of Embodiments 1-16, wherein $R^{11}$ is alkyl substituted with $NR^{13}R^{14}$, wherein $R^{13}$ and $R^{14}$ are each independently H, optionally substituted alkyl, optionally substituted aryl, optionally substituted arylalkyl or $R^{13}$ and $R^{14}$, together with the nitrogen atom to which they are attached, form an optionally substituted heterocyclyl group.

Embodiment 19 relates to a compound of any one of Embodiments 1-16, wherein $R^{11}$ is alkyl substituted with $OR^{13}$, wherein $R^{13}$ is H, optionally substituted alkyl, optionally substituted aryl or optionally substituted arylalkyl.

Embodiment 20 relates to a compound of any one of Embodiments 1-16, wherein $R^{11}$ is $C(O)N(R)_2$, wherein each R group is, independently, hydrogen, alkyl, acyl, cycloalkyl, aryl, aralkyl, heterocyclyl, heteroaryl, or heteroarylalkyl.

Embodiment 21 realtes to a compound of any one of Embodiments 1-20, wherein the compound is a compound of the formula (V) or (VI):

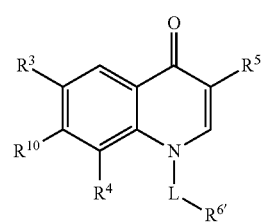

(V)

-continued

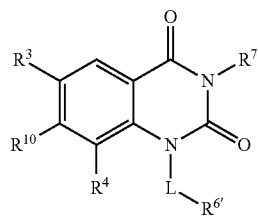
(VI)

wherein $R^3$, $R^4$, and $R^7$ are as defined for compounds of the formula (I); L is $-(CH_2)_n-$, wherein n is an integer from 1 to 3 (e.g., 1); $R^{6'}$ is:

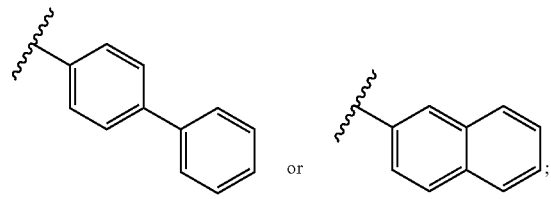 [SMILES: *c1ccc(-c2ccccc2)cc1 ; *c1ccc2ccccc2c1]

and
$R^{10}$ is:

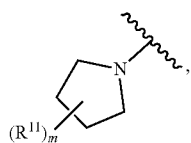

wherein $R^{11}$ is $C(O)N(R)_2$ (wherein each R group is, independently, hydrogen, alkyl, acyl, cycloalkyl, aryl, aralkyl, heterocyclyl, heteroaryl, or heteroarylalkyl), alkyl substituted with $-OR$ or alkyl substituted with $-N(R)_2$.

Embodiment 22 relates to a compound of any one of Embodiments 1-7, wherein the compound has the formula:

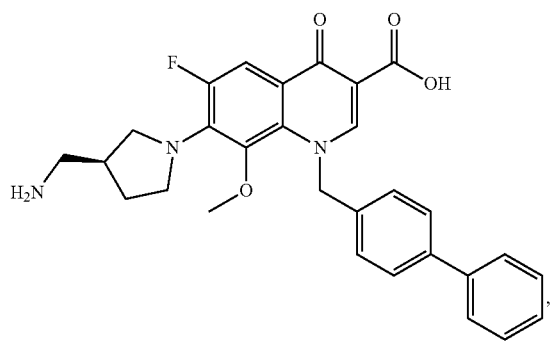

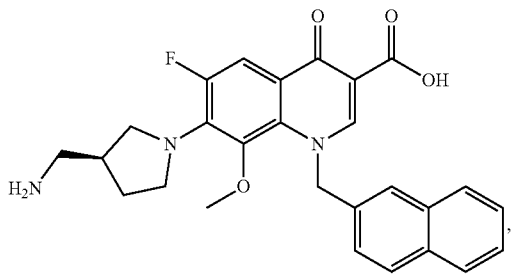

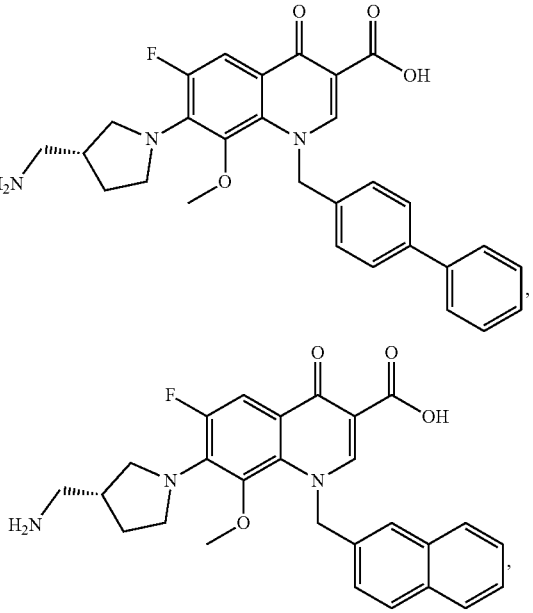

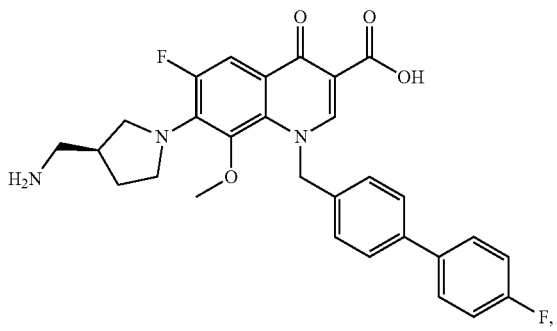

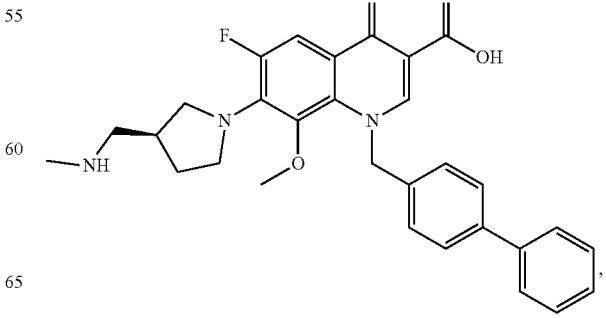

67
-continued
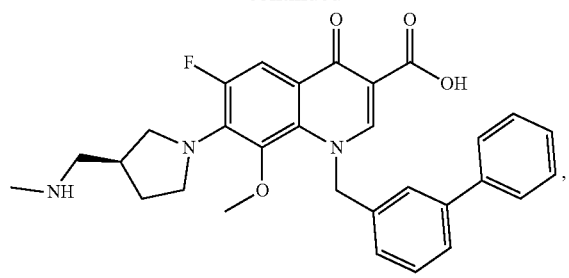
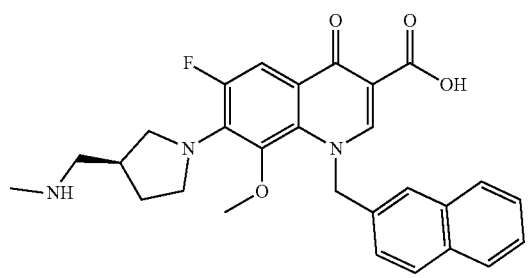
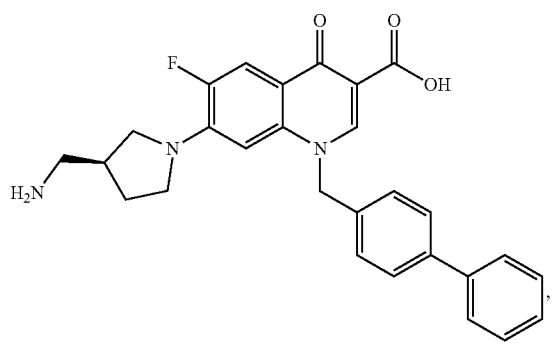
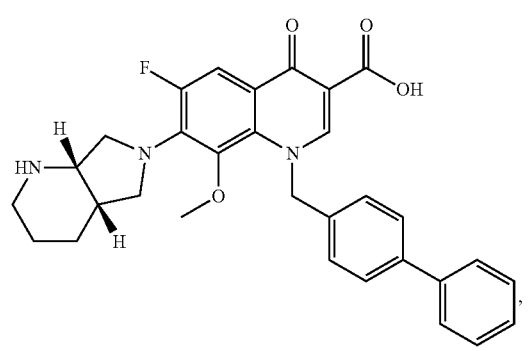
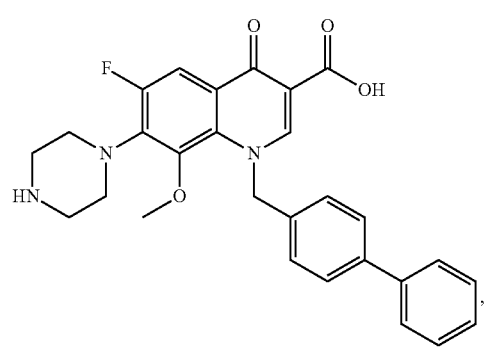
68
-continued
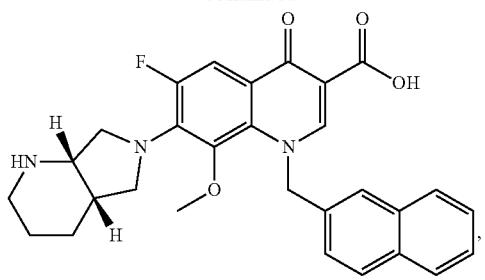
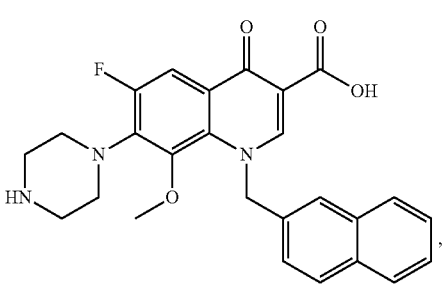
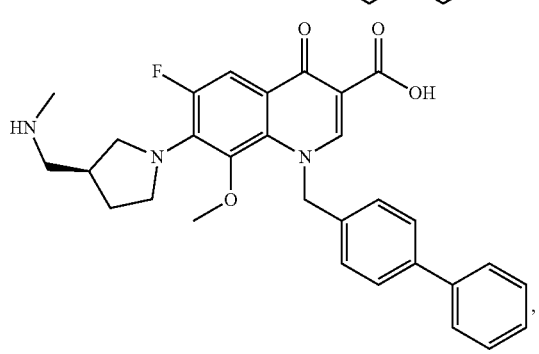
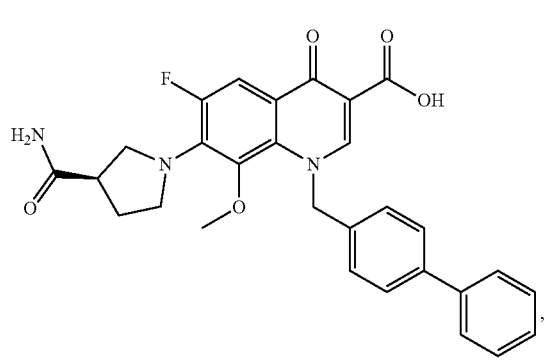
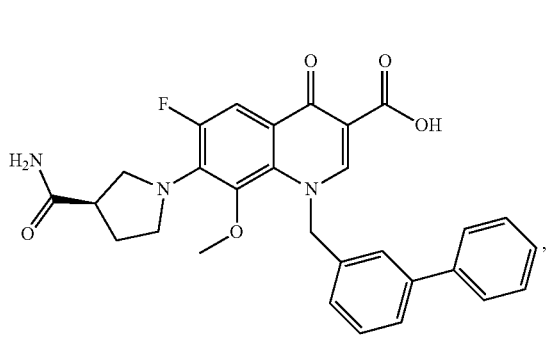

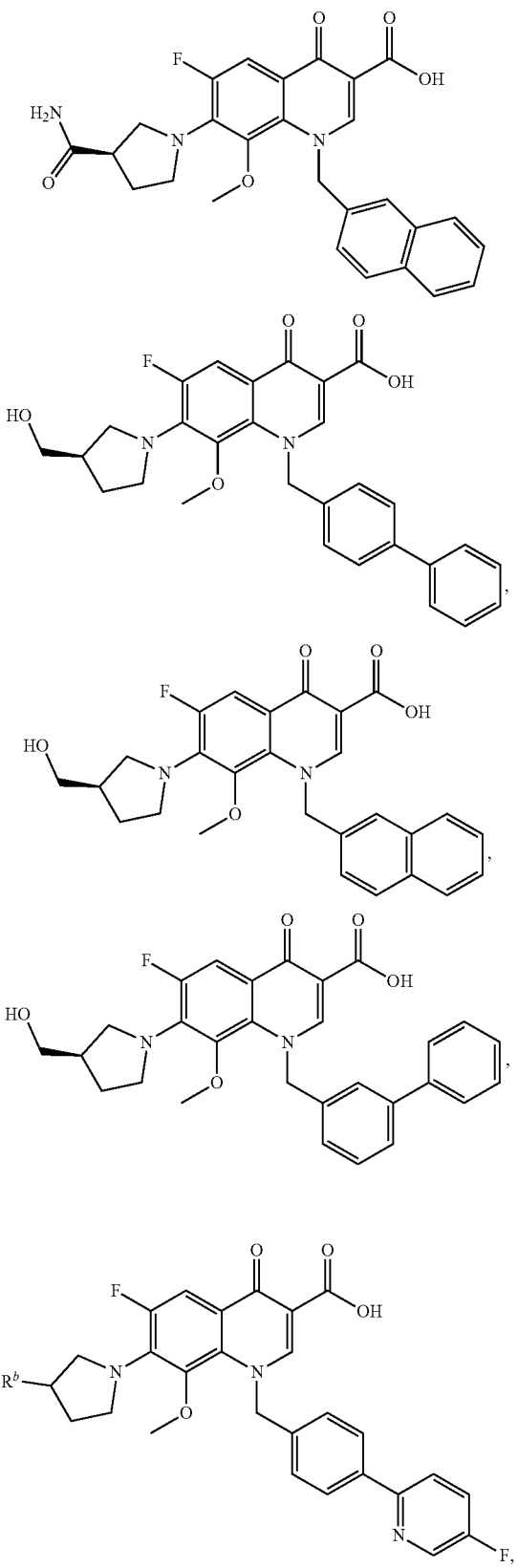
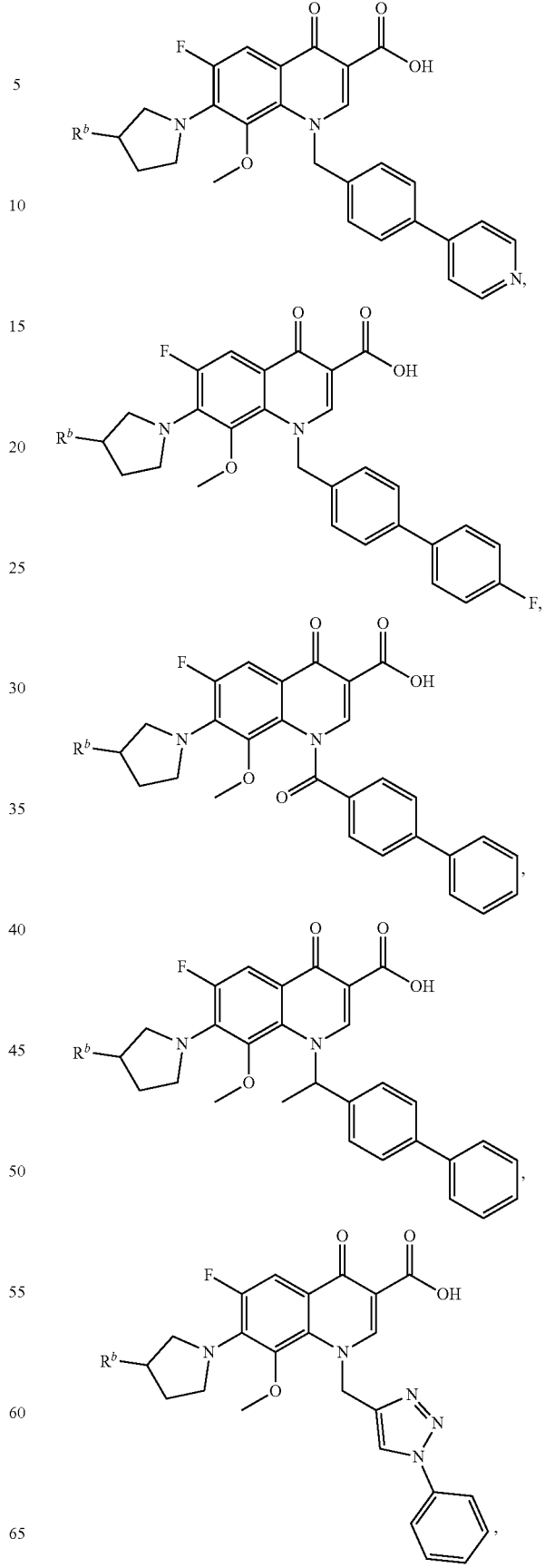
(wherein $R^b$ is —CH$_2$NHCH$_3$, —CH$_2$OH or C(O)NH$_2$), 71
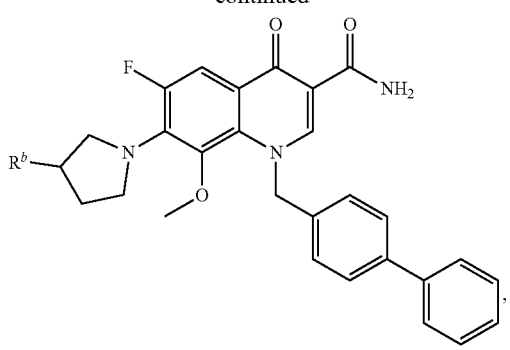
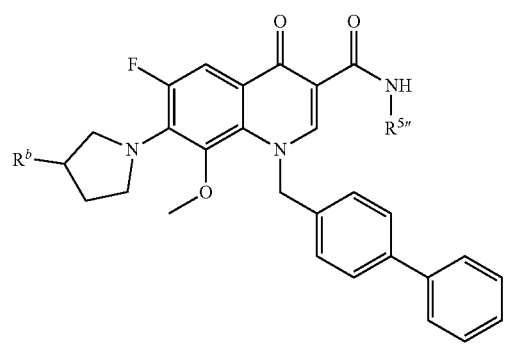
(wherein R[5″] is defined herein);
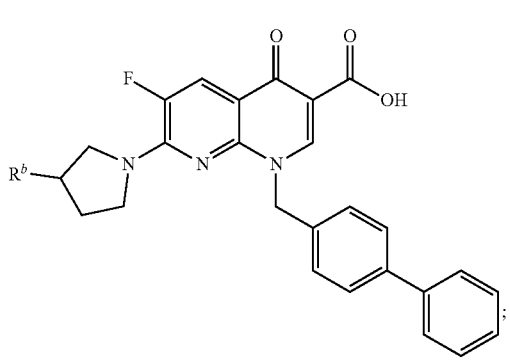
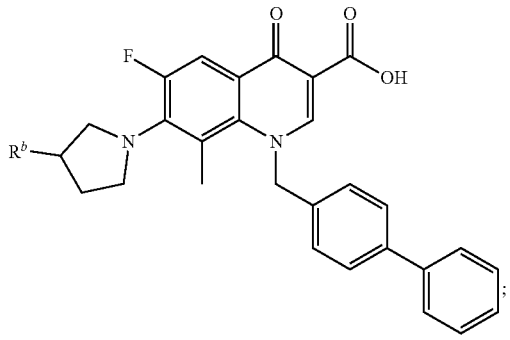
72
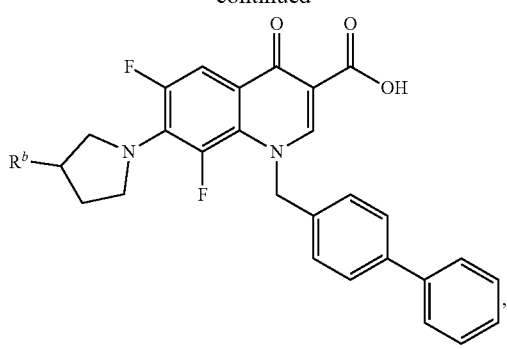
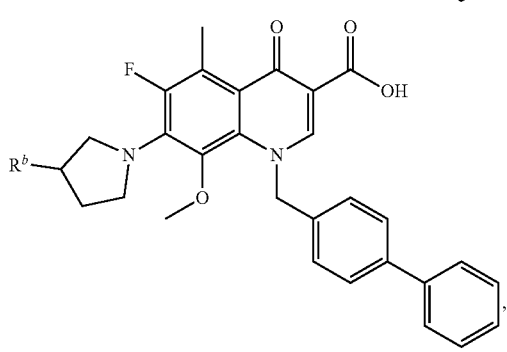
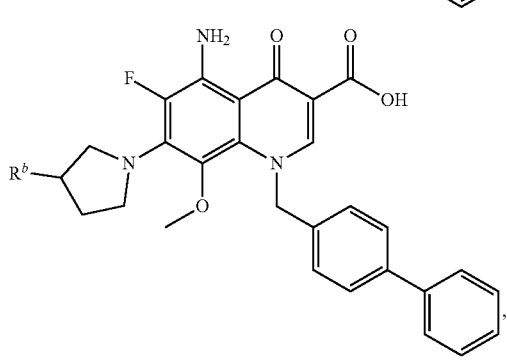
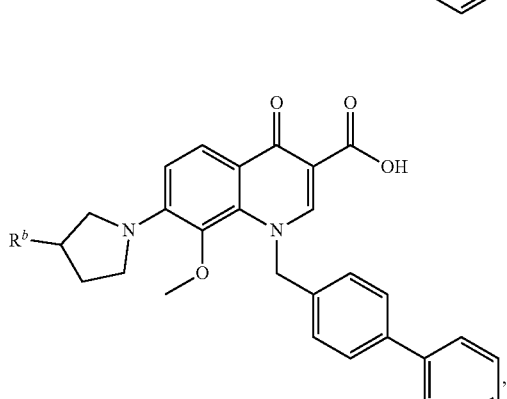
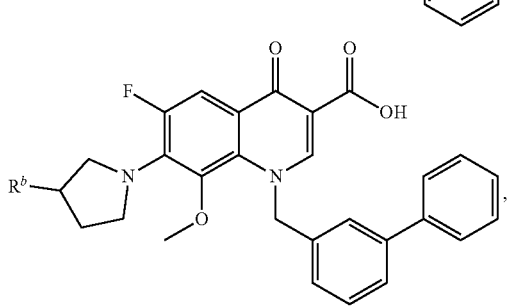

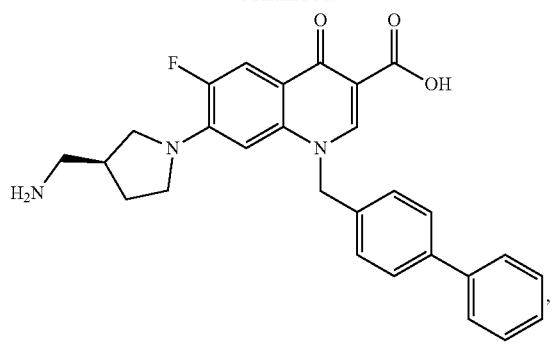
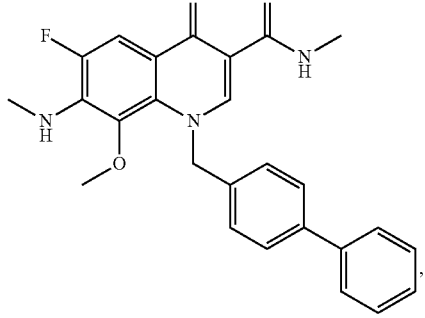
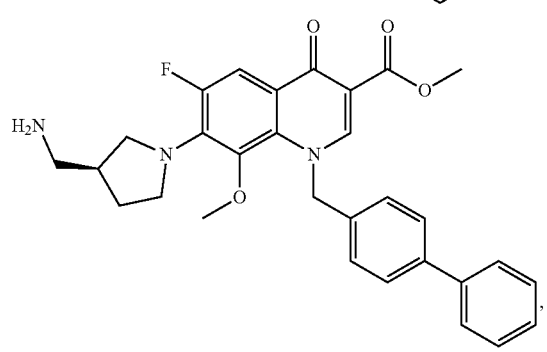
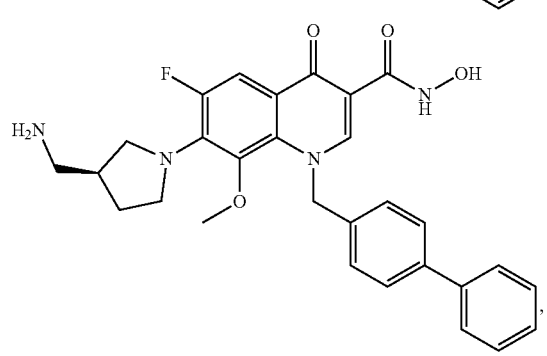
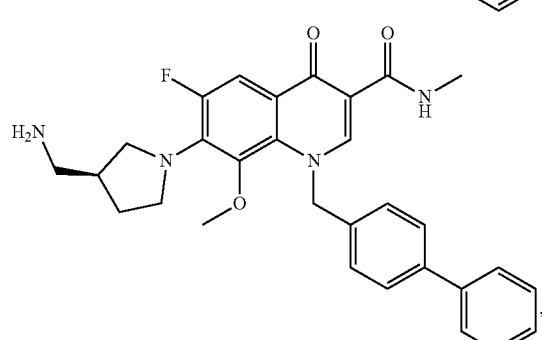
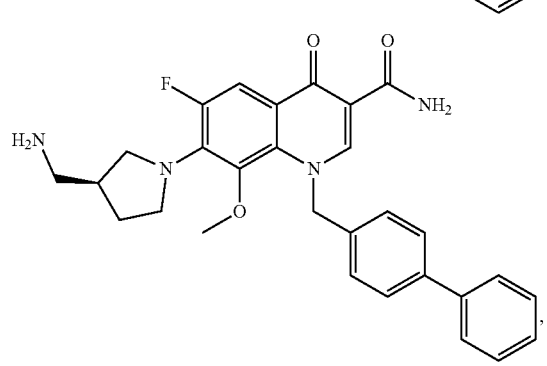

75
-continued
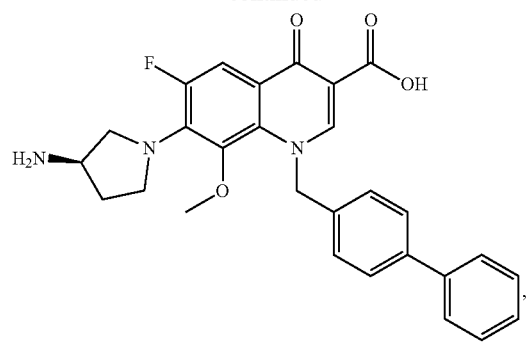
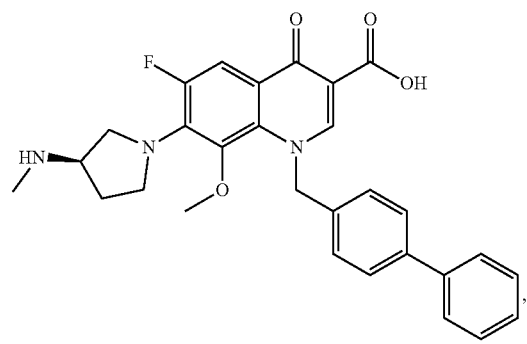
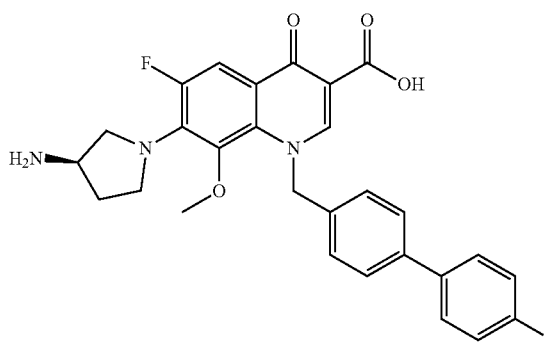
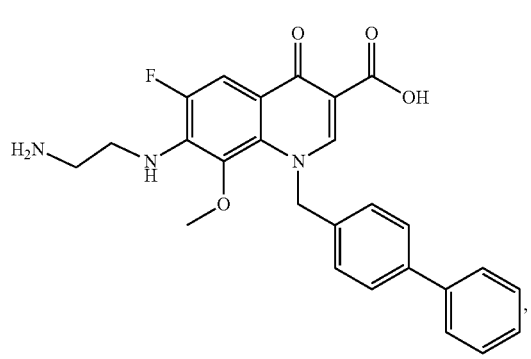
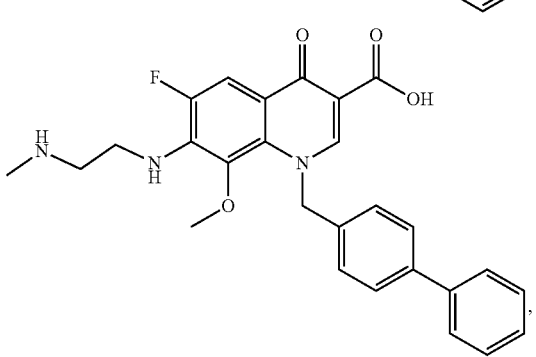
76
-continued
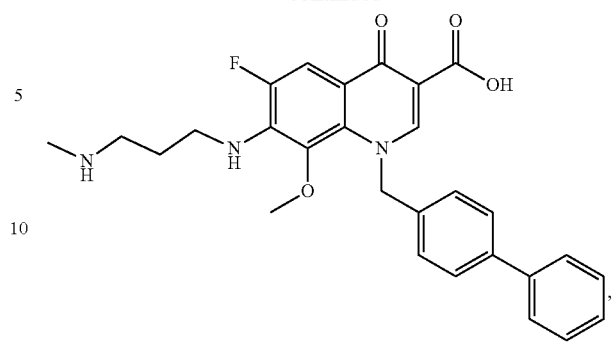
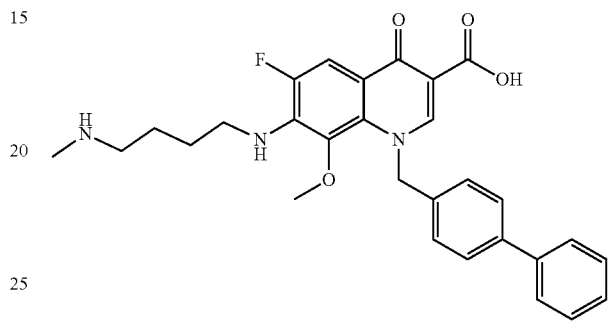
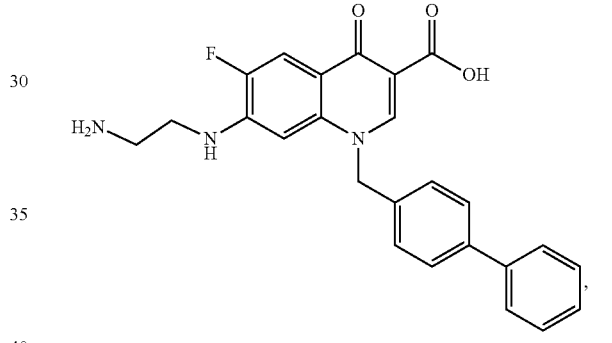
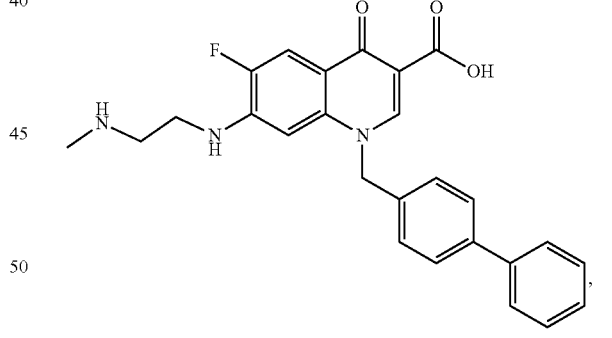
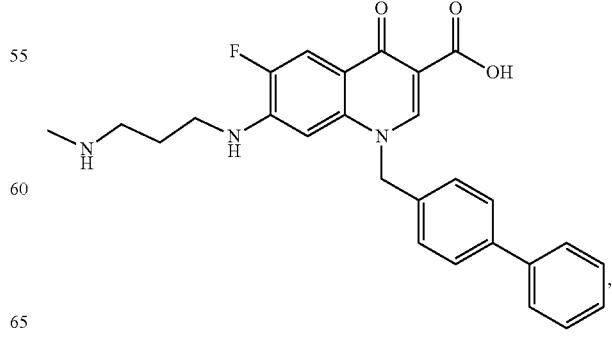

77

-continued

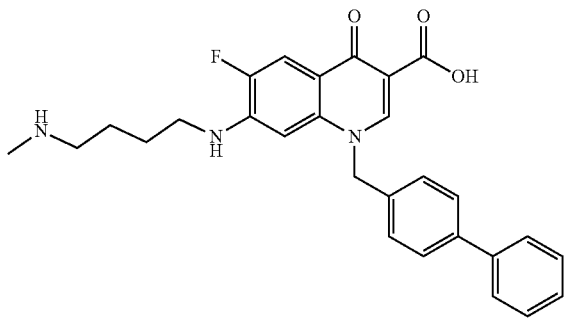

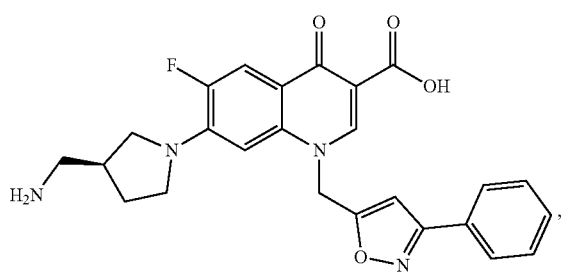

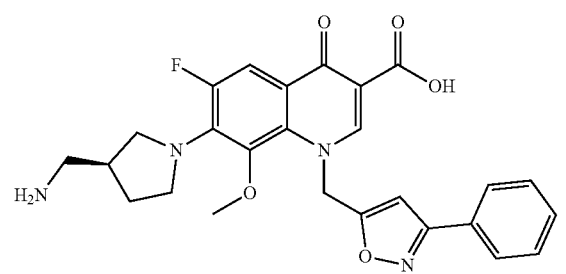

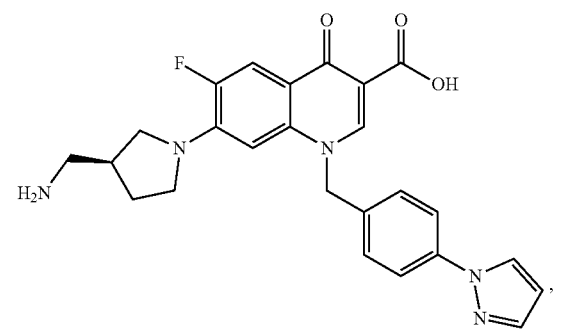

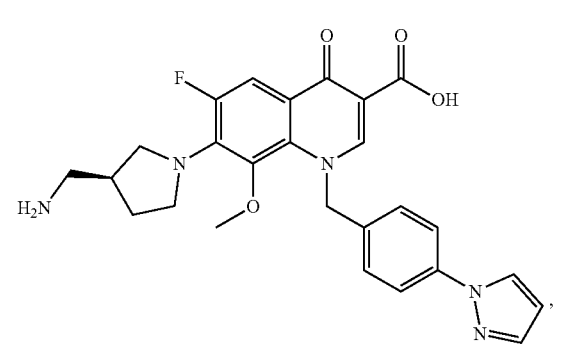

78

-continued

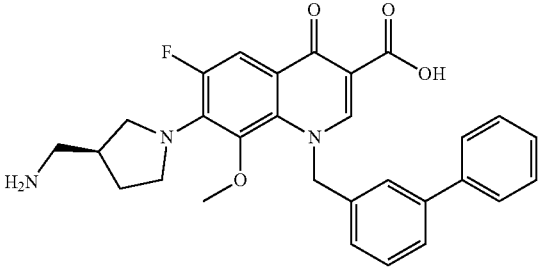 [SMILES: COc1c(N2CC[C@@H](CN)C2)c(F)cc2c(=O)c(C(=O)O)cn(Cc3cccc(-c4ccccc4)c3)c12]

or pharmaceutically acceptable salts, polymorphs, prodrugs, solvates or clathrates thereof.

Embodiment 23 relates to the compound as in any preceding Embodiment, wherein the IC50 for human topoisomerase II is about four to about 1000 times greater than the $IC_{50}$ for human topoisomerase I.

Embodiment 24 relates to the compound as in any preceding Embodiment, wherein the compound does not substantially increase an amount of nicked and linear DNAs in DNA cleavage assays.

Embodiment 25 relates to a pharmaceutical composition comprising one or more compounds as in any preceding Embodiment and one or more pharmaceutically acceptable carriers, diluents, excipients or combinations thereof.

Embodiment 26 relates to a method for treating cancer comprising administering a therapeutically effective amount of one, or more compounds as in any one of Embodiments 1-24 or a pharmaceutical composition of Embodiment 25, to a patient in need thereof.

Embodiment 27 relates to a method of modulating a human topoisomerase, comprising contacting the topoisomerase with an effective amount or concentration of a compound as in any one of Embodiments 1-24.

Embodiment 28 relates to the method of Embodiment 27, wherein the human topoisomerase is human topoisomerase I.

Embodiment 9 relates to the method of Embodiment 28, wherein the compound has an $IC_{50}$ for human topoisomerase II that is about four to about 1000 times greater than an $IC_{50}$ of the same compound for human topoisomerase I.

What is claimed is:
1. A compound of the formula (I):

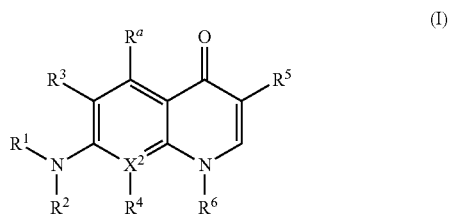

or a pharmaceutically acceptable salt, polymorph, prodrug, solvate or clathrate thereof, wherein:

$R^a$ is halo, nitre, cyano, optionally substituted alkyl, optionally substituted alkoxy, optionally substituted aryl, optionally substituted aryloxy, optionally substituted heteroaryl, or $NR^{a'}R^{a''}$, wherein $R^{a'}$ and $R^{a''}$ are each, independently, H or optionally substituted alkyl;

$R^1$ and $R^2$ are each independently H, optionally substituted alkyl, optionally substituted aryl, optionally substituted arylalkyl or R¹ and R², together with the nitrogen atom to which they are attached, form an optionally substituted heterocyclyl group;

R³ is H or halo;

R⁴ is H, halo, optionally substituted alkyl or optionally substituted alkoxy, but R⁴ is absent if X² is N;

X² is N or C;

R⁵ is H, OH, optionally substituted alkoxy, —C(O)R⁵' (wherein R⁵' is H, OH, optionally substituted alkyl, optionally substituted aryl, optionally substituted alkoxy or —N(R⁵")₂, wherein each R⁵" is, independently, H, OH, optionally substituted alkoxy, optionally substituted alkyl or optionally substituted arylalkyl) or —N(R⁵')²; and R⁶ is the group -L-R⁶', wherein L is a linker group and R⁶' is two aryl groups, an aryl group and a heterocyclyl group or two heterocycyl groups, each of which can be optionally substituted, such that the compound of the formula (I) is (a) not a topoisomerase II poison, (b) inhibits topoisomerase I and topoisomerase II and/or (c) inhibits topoisomerase I to a greater extent than topoisomerase II.

2. The compound of claim 1, wherein when R⁶ is:

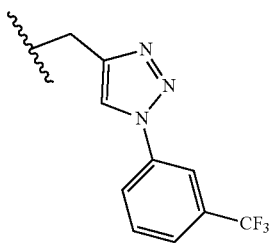 [SMILES: *Cc1cn(-c2cccc(C(F)(F)F)c2)nn1]

R¹ and R², together with the nitrogen atom to which they are attached, form an optionally substituted pyrrolidinyl group.

3. The compound of claim 1, wherein the IC₅₀ for human topoisomerase II is about four to about 1000 times greater than the IC₅₀ for human topoisomerase I.

4. The compound of claim 1, wherein the compound does not substantially increase an amount of nicked and linear DNAs in DNA cleavage assays.

5. A pharmaceutical composition comprising one or more compounds of claim 1 and one or more pharmaceutically acceptable carriers, diluents, excipients or combinations thereof.

6. A method for treating cancer comprising administering a therapeutically effective amount of one, or more compounds of claim 1 or a pharmaceutical composition of claim 5, to a patient in need thereof.

7. A method of modulating a human topoisomerase, comprising contacting the topoisomerase with an effective amount or concentration of a compound of claim 1.

8. The method of claim 7, wherein the human topoisomerase is human topoisomerase I.

9. A compound of the formula (Ia):

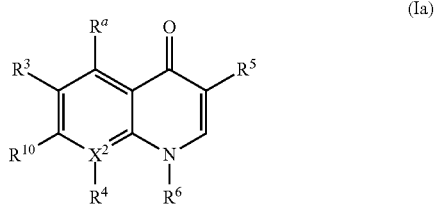

or a pharmaceutically acceptable salt, polymorph, prodrug, solvate or clathrate thereof, wherein:

Rᵃ is halo, nitro, cyano, optionally substituted alkyl, optionally substituted alkoxy, optionally substituted aryl, optionally substituted aryloxy, optionally substituted heteroaryl, or NRᵃ'Rᵃ", wherein Rᵃ' and Rᵃ" are each, independently, H or optionally substituted alkyl;

R³ is H or halo;

R⁴ is H, halo, optionally substituted alkyl or optionally substituted alkoxy, but R⁴ is absent if X² is N;

X² is N or C;

R⁵ is H, OH, optionally substituted alkoxy, —C(O)R⁵' (wherein R⁵' is H, OH, optionally substituted alkyl, optionally substituted aryl, optionally substituted alkoxy or —N(R⁵")₂, wherein each R⁵" is, independently, H, OH, optionally substituted alkoxy, optionally substituted alkyl or optionally substituted arylalkyl) or —N(R⁵")₂;

R⁶ is the group -L-R⁶', wherein L is a linker group and R⁶' is a group of the formula:

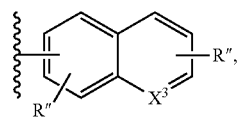

wherein each R" is, independently H or halo and X³ is N or CH, a group of the formula

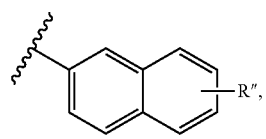

two aryl groups, an aryl group and a heterocyclyl group or two heterocycyl groups, each of which can be optionally substituted, such that the compound of the formula (Ia) is (a) not a topoisomerase II poison, (b) inhibits topoisomerase I and topoisomerase II and/or (c) inhibits topoisomerase I to a greater extent than topoisomerase II; and R¹⁰ is aryl,

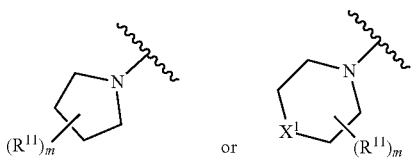

wherein each R¹¹ is H, —N(R⁵')₂, C(O)N(R)₂ (wherein each R group is, independently, hydrogen, alkyl, acyl, cycloalkyl, aryl, aralkyl, heterocyclyl, heteroaryl, or heteroarylalkyl), optionally substituted alkyl or two adjacent $R^{11}$ groups, together with the atoms to which they are attached form an optionally substituted cycloalkyl group or an optionally substituted heterocylcyl group; m is an integer from 1 to 3, and $X^1$ is O or $NR^{12}$, wherein $R^{12}$ is H or optionally substituted alkyl or $R^{12}$ and an adjacent $R^{11}$ group, together with the atoms to which they are attached, form an optionally substituted heterocyclyl group.

10. The compound of claim 9, wherein
$R^a$ is optionally substituted alkyl or $NH_2$; and
$R^6$ is $-(CH_2)_n-R^{6''}$ or $-C(O)R^{6''}$ wherein n is an integer from 1 to 3 and $R^{6''}$ is is two aryl groups, an aryl group and a heterocyclyl group or two heterocycyl groups, each of which can be optionally substituted, such that the compound of the formula (Ia) is (a) not a topoisomerase II poison, (b) inhibits topoisomerase I and topoisomerase II and/or (c) inhibits topoisomerase I to a greater extent than topoisomerase II.

11. The compound of claim 10, wherein $R^{6''}$ is:

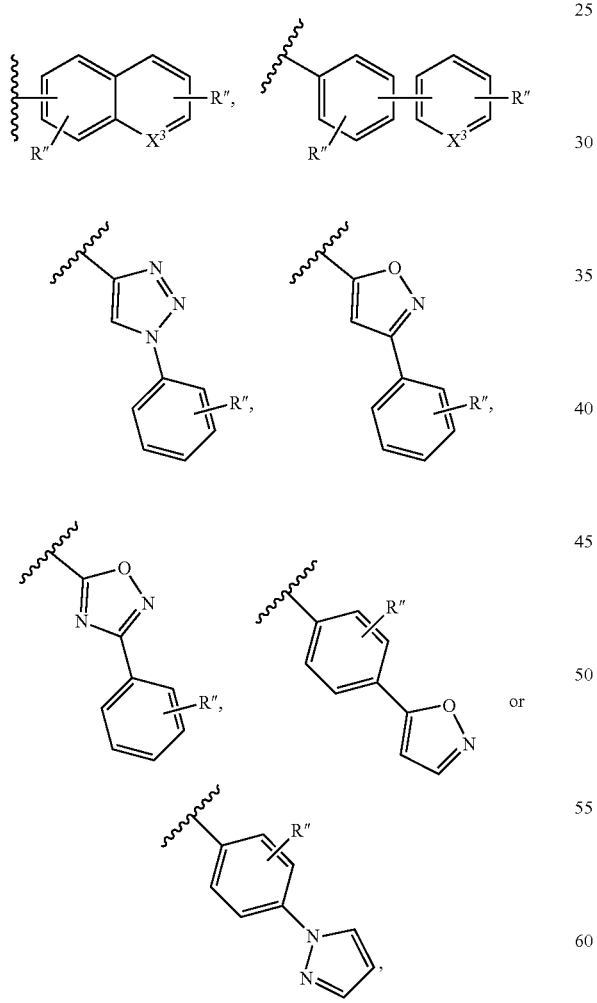

wherein each R" is, independently H or halo and $X^3$ is N or CH; and
$R^{10}$ is aryl,

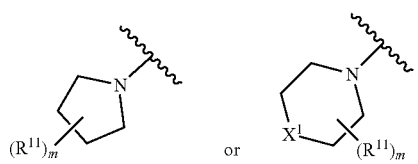

wherein each $R^{11}$ is H, $C(O)N(R)_2$ (wherein each R group is, independently, hydrogen, alkyl, acyl, cycloalkyl, aryl, aralkyl, heterocyclyl, heteroaryl, or heteroarylalkyl), optionally substituted alkyl or two adjacent $R^{11}$ groups, together with the atoms to which they are attached form an optionally substituted cycloalkyl group or an optionally substituted heterocylcyl group; m is an integer from 1 to 3; and $X^1$ is O or $NR^{12}$, wherein $R^{12}$ is H or optionally substituted alkyl or $R^{12}$ and an adjacent $R^{11}$ group, together with the atoms to which they are attached, form an optionally substituted heterocyclyl group.

12. The compound of claim 10, wherein $R^{6''}$ is:

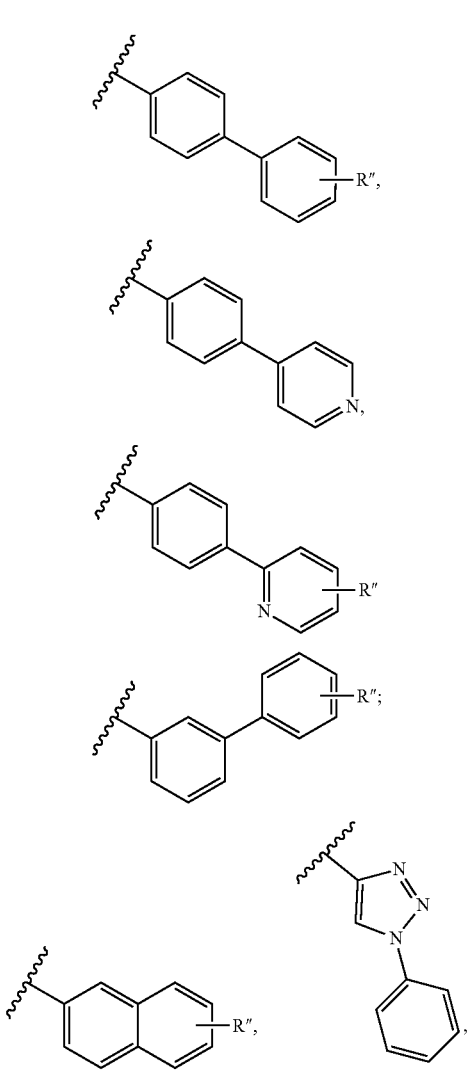

-continued

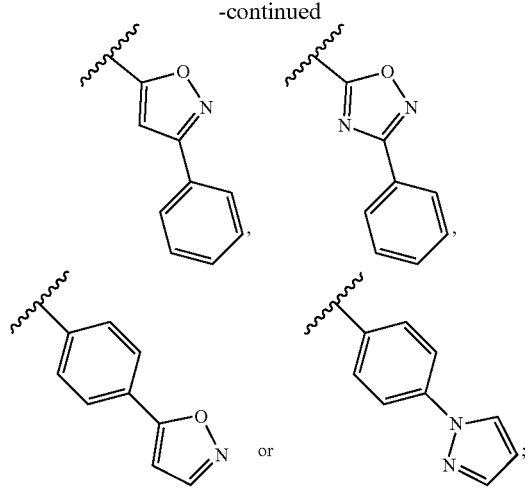

wherein each R" is, independently H or halo.

13. The compound of claim 9, wherein $R^{11}$ is alkyl substituted with $NR^{13}R^{14}$, wherein $R^{13}$ and $R^{14}$ are each independently H, optionally substituted alkyl, optionally substituted aryl, optionally substituted arylalkyl or $R^{13}$ and $R^{14}$, together with the nitrogen atom to which they are attached, form an optionally substituted heterocyclyl group.

14. The compound of claim 9, wherein $R^{11}$ is alkyl substituted with $OR^{13}$, wherein $R^{13}$ is H, optionally substituted alkyl, optionally substituted aryl or optionally substituted arylalkyl.

15. The compound of claim 9, wherein $R^{11}$ is $C(O)N(R)_2$, wherein each R group is, independently, hydrogen, alkyl, acyl, cycloalkyl, aryl, aralkyl, heterocyclyl, heteroaryl, or heteroarylalkyl.

16. A compound of the formula (II):

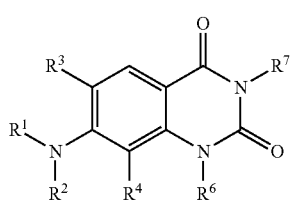

(II)

or a pharmaceutically acceptable salt, polymorph, prodrug, solvate or clathrate thereof, wherein:
$R^1$ and $R^2$ are each independently H, optionally substituted alkyl, optionally substituted aryl, optionally substituted arylalkyl or $R^1$ and $R^2$, together with the nitrogen atom to which they are attached, form an optionally substituted heterocyclyl group;
$R^3$ is H or halo:
$R^4$ is H, halo, optionally substituted alkyl or optionally substituted alkoxy;
$R^6$ is the group -L-$R^{6'}$, wherein L is a linker group and $R^{6'}$ is two aryl groups, an aryl group and a heterocyclyl group or two heterocycyl groups, each of which can be optionally substituted, such that the compound of the formula (II) is (a) not a topoisomerase II poison, (b) inhibits topoisomerase I and topoisomerase II and/or (c) inhibits topoisomerase I to a greater extent than topoisomerase II; and $R^7$ is H, OH, optionally substituted alkoxy, optionally substituted alkyl or $NR^8R^9$, wherein Re and $R^9$ are each independently H, optionally substituted alkyl, optionally substituted aryl or optionally substituted arylalkyl.

17. A compound of the formula (IIa):

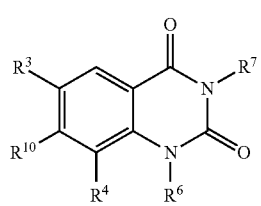

(IIa)

or a pharmaceutically acceptable salt, polymorph, prodrug, solvate or clathrate thereof, wherein:
$R^3$ is H or halo;
$R^4$ is H, halo, optionally substituted alkyl or optionally substituted alkoxy;
$R^6$ is the group -L-$R^{6'}$, wherein L is a linker group and $R^{6'}$ is two aryl groups, an aryl group and a heterocyclyl group or two heterocycyl groups, each of which can be optionally substituted, such that the compound of the formula (IIa) is (a) not a topoisomerase II poison, (b) inhibits topoisomerase I and topoisomerase H and/or (c) inhibits topoisomerase I to a greater extent than topoisomerase II;
$R^7$ is H, optionally substituted alkyl or $NR^8R^9$, wherein $R^8$ and $R^9$ are each independently H, optionally substituted alkyl, optionally substituted aryl or optionally substituted arylalkyl; and
$R^{10}$ is aryl,

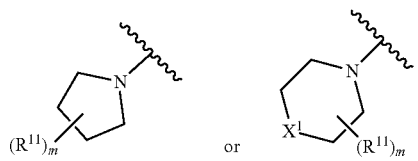

wherein each $R^{11}$ is H, $C(O)N(R)_2$ (wherein each R group is, independently, hydrogen, alkyl, acyl, cycloalkyl, aryl, aralkyl, heterocyclyl, heteroaryl, or heteroarylalkyl), optionally substituted alkyl or two adjacent $R^{11}$ groups, together with the atoms to which they are attached form an optionally substituted cycloalkyl group or an optionally substituted heterocylcyl group; m is an integer from 1 to 3; and $X^1$ is O or $NR^{12}$, wherein $R^{12}$ is H or optionally substituted alkyl or $R^{12}$ and an adjacent $R^{11}$ group, together with the atoms to which they are attached, form an optionally substituted heterocyclyl group.

18. A compound of the formula (III) or (IV):

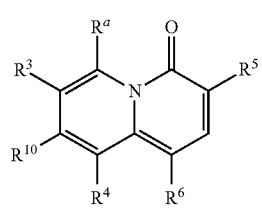

(III)

-continued

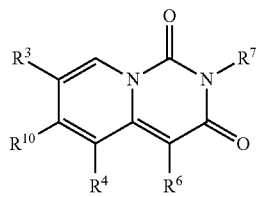
(IV)

or a pharmaceutically acceptable salt, polymorph, prodrug, solvate or clathrate thereof, wherein:

$R^a$ is halo, nitro, cyano, optionally substituted alkyl, optionally substituted alkoxy, optionally substituted aryl, optionally substituted aryloxy, optionally substituted heteroaryl, or $NR^{a'}R^{a''}$, wherein $R^{a'}$ and $R^{a''}$ are each, independently, H or optionally substituted alkyl;

$R^3$ is H or halo;

$R^4$ is H, halo, optionally substituted alkyl or optionally substituted alkoxy;

$R^5$ is H, OH, optionally substituted alkoxy, —C(O)R$^{5'}$ (wherein R$^{5'}$ is H, OH, optionally substituted alkyl, optionally substituted aryl, optionally substituted alkoxy or —N(R$^{5''}$)$_2$, wherein each R$^{5''}$ is, independently, H, OH, optionally substituted alkoxy, optionally substituted alkyl or optionally substituted arylalkyl) or —N(R$^{5''}$)$_2$;

$R^6$ is the group -L-R$^{6'}$, wherein L is a linker group and R$^{6'}$ is two aryl groups, an aryl group and a heterocyclyl group or two heterocycyl groups, each of which can be optionally substituted, such that the compound of the formula (III) or (IV) is (a) not a topoisomerase II poison, (b) inhibits topoisomerase I and topoisomerase II and/or (c) inhibits topoisomerase I to a greater extent than topoisomerase II;

$R^7$ is H, OH, optionally substituted alkoxy, optionally substituted alkyl or NR$^8$R$^9$, wherein R$^8$ and R$^9$ are each independently H, optionally substituted alkyl, optionally substituted aryl or optionally substituted arylalkyl; and $R^{10}$ is aryl,

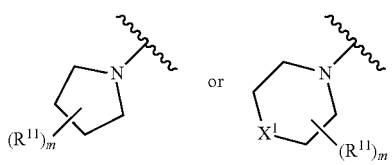

wherein each R$^{11}$ is H, —N(R$^{5''}$)$_2$, C(O)N(R)$_2$ (wherein each R group is, independently, hydrogen, alkyl, acyl, cycloalkyl, aryl, aralkyl, heterocyclyl, heteroaryl, or heteroarylalkyl), optionally substituted alkyl or two adjacent R$^{11}$ groups, together with the atoms to which they are attached form an optionally substituted cycloalkyl group or an optionally substituted heterocylcyl group; m is an integer from 1 to 3; and X$^1$ is O or NR$^{12}$, wherein R$^{12}$ is H or optionally substituted alkyl or R$^{12}$ and an adjacent R$^{11}$ group, together with the atoms to which they are attached, form an optionally substituted heterocyclyl group.

19. A compound of the formula (V) or (VI):

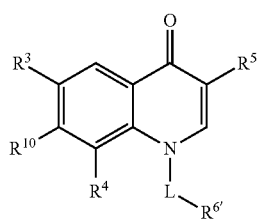
(V)

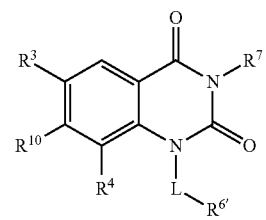
(VI)

or a pharmaceutically acceptable salt, polymorph, prodrug, solvate or clathrate thereof, wherein:

$R^3$ is H or halo;

$R^4$ is H, halo, optionally substituted alkyl or optionally substituted alkoxy;

$R^5$ is H, OH, optionally substituted alkoxy, —C(O)R$^{5'}$ (wherein R$^{5'}$ is H, OH, optionally substituted alkyl, optionally substituted aryl, optionally substituted alkoxy or —N(R$^{5''}$)$_2$, wherein each R$^{5''}$ is, independently, H, OH, optionally substituted alkoxy, optionally substituted alkyl or optionally substituted arylalkyl) or —N(R$^{5''}$)$_2$ $R^7$ is H, OH, optionally substituted alkoxy, optionally substituted alkyl or NR$^8$R$^9$, wherein R$^8$ and R$^9$ are each independently H, optionally substituted alkyl, optionally substituted aryl or optionally substituted arylalkyl;

L is —(CH$_2$)$_n$—, wherein n is an integer from 1 to 3; R$^{6'}$ is:

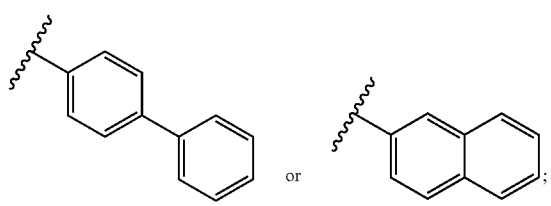 [SMILES: *c1ccc(-c2ccccc2)cc1 ; *c1ccc2ccccc2c1]

$R^{10}$ is:

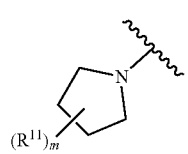

wherein m is an integer from 1 to 3; R$^{11}$ is C(O)N(R)$_2$ (wherein each R group is, independently, hydrogen, alkyl, acyl, cycloalkyl, aryl, aralkyl, heterocyclyl, heteroaryl, or heteroarylalkyl), alkyl substituted with —OR or alkyl substituted with —N(R)$_2$.

20. A compound of the formula:
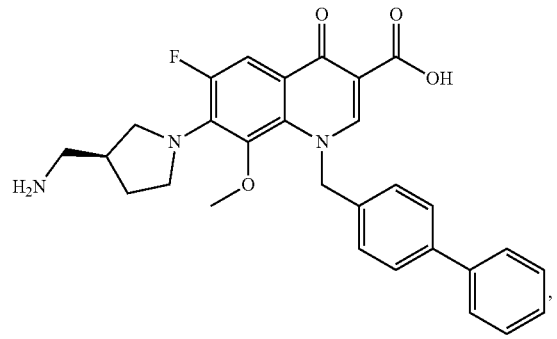
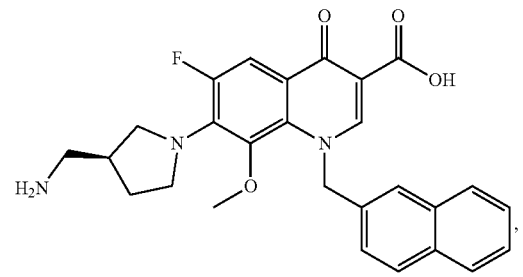
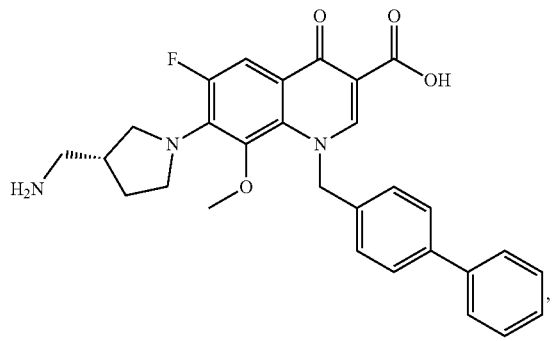
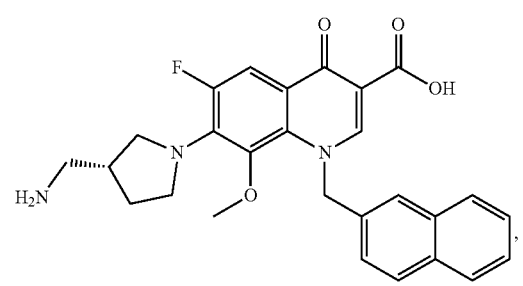
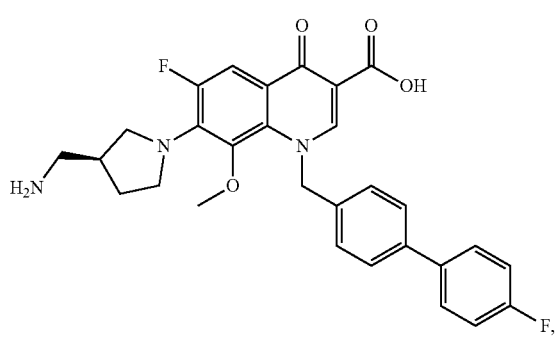
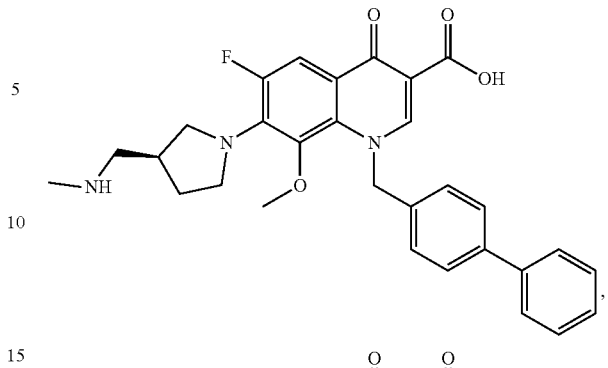
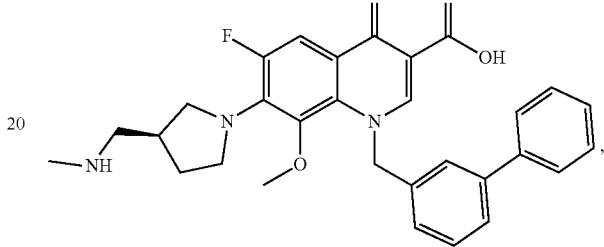
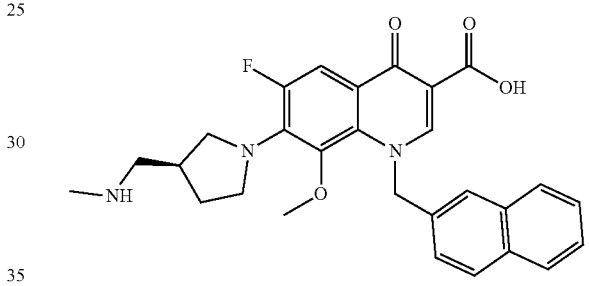
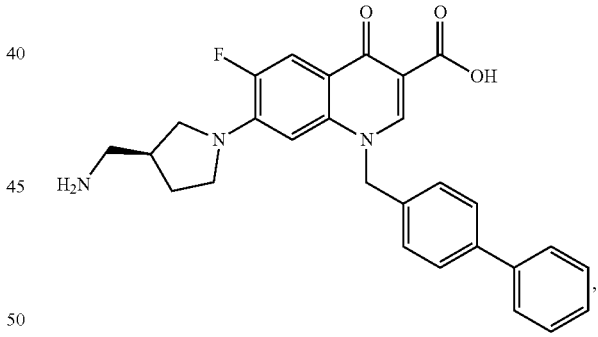
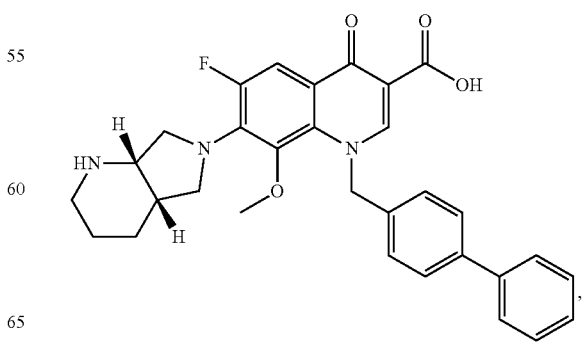

89
-continued
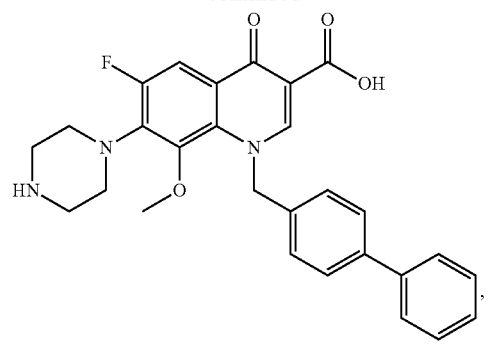
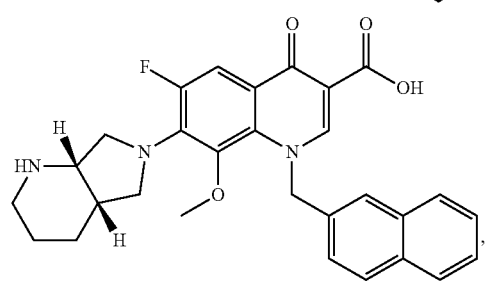
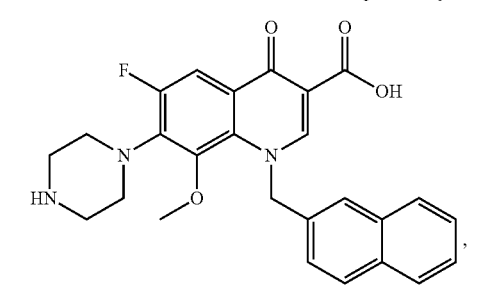
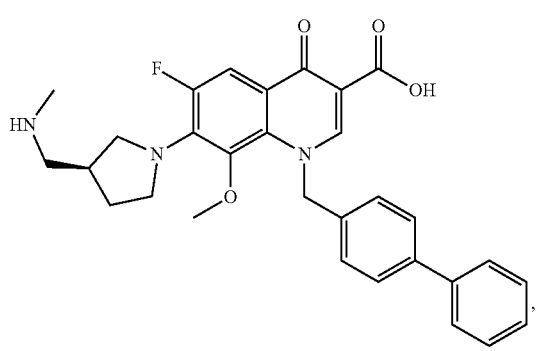
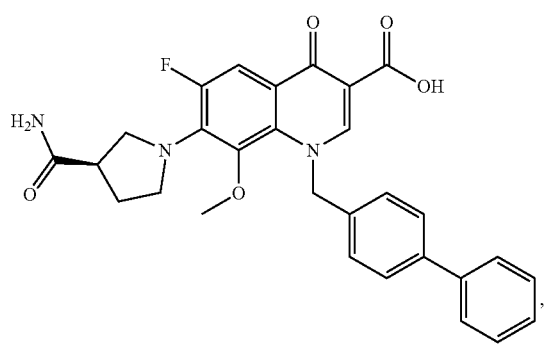
90
-continued
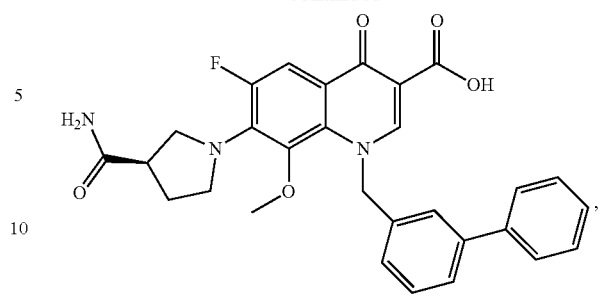
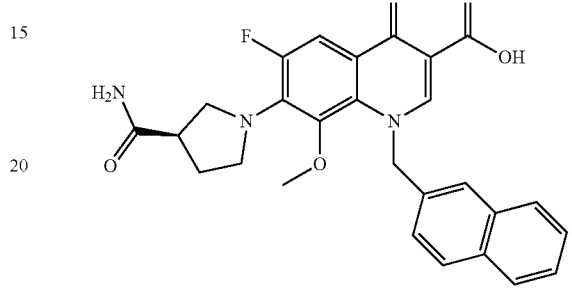
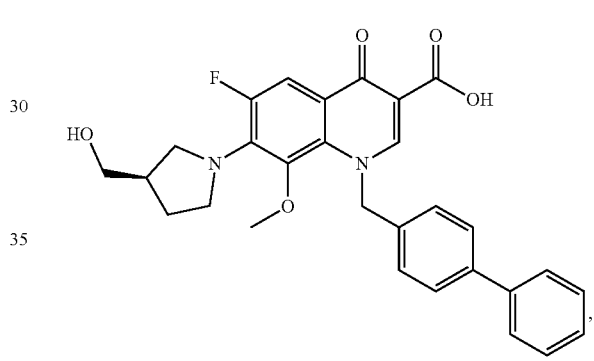
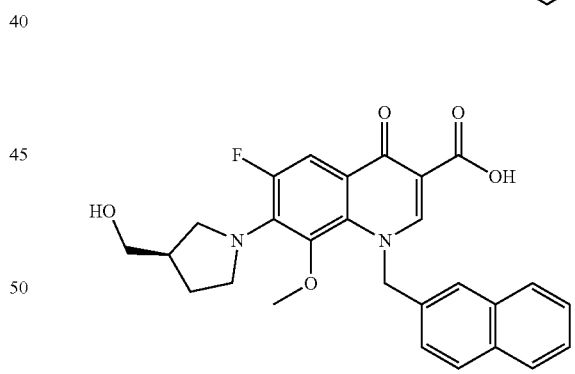
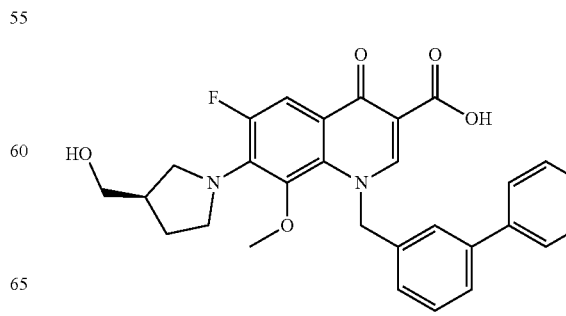

91
-continued
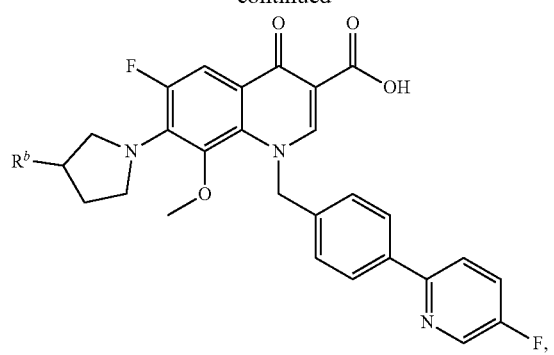
(wherein $R^b$ is —CH$_2$NHCH$_3$, —CH$_2$OH or C(O)NH$_2$),
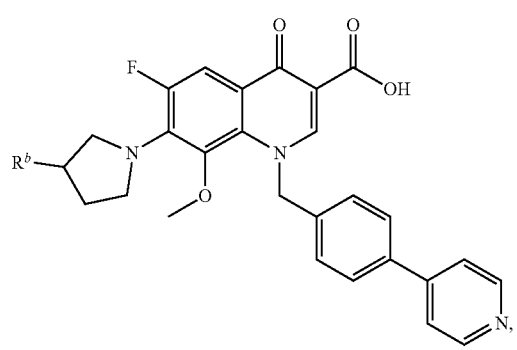
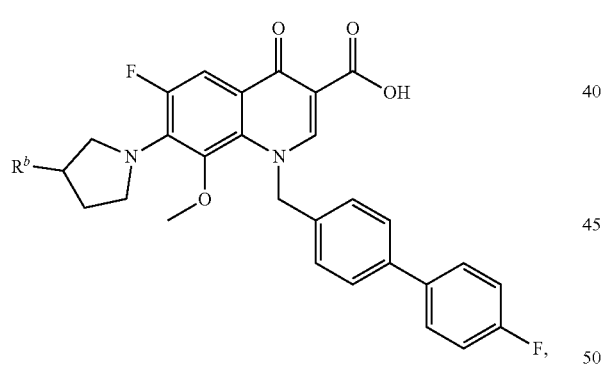
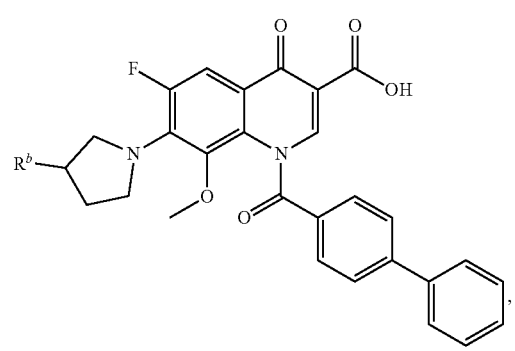
92
-continued
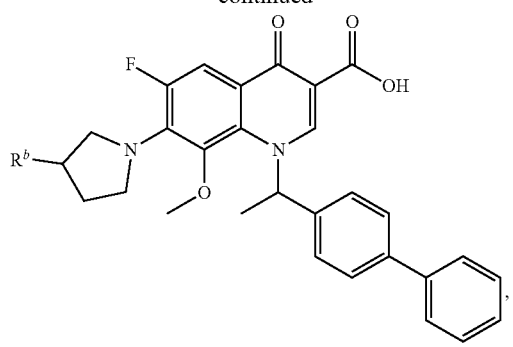
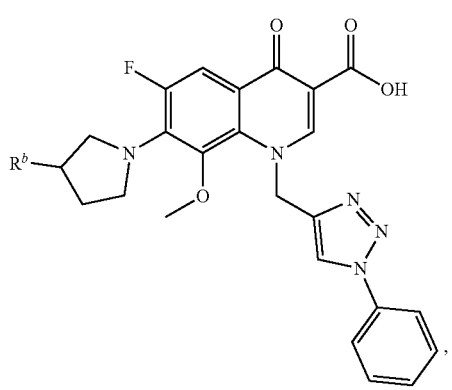
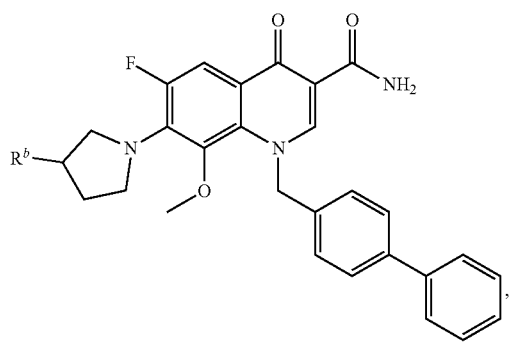
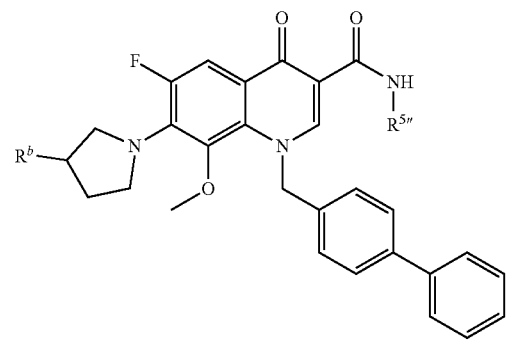
(wherein $R^{5''}$ is H, optionally substituted alkyl or optionally substituted arylalkyl);

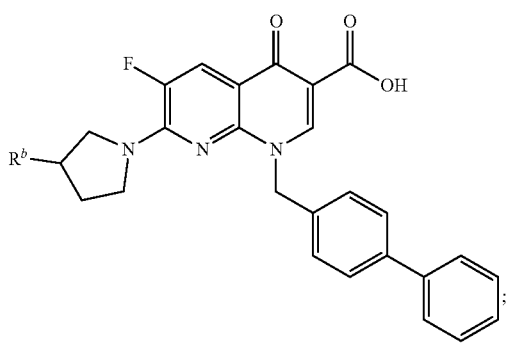
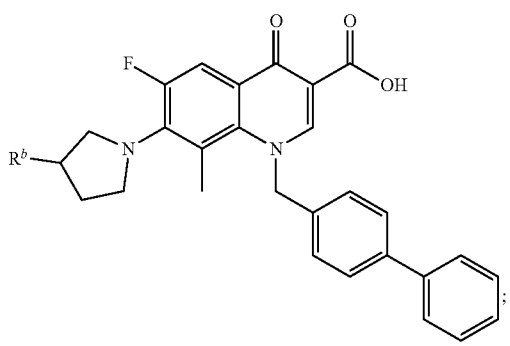
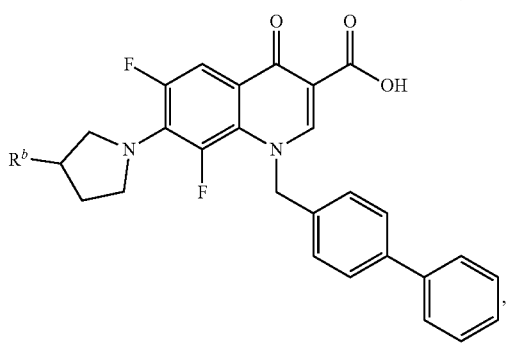
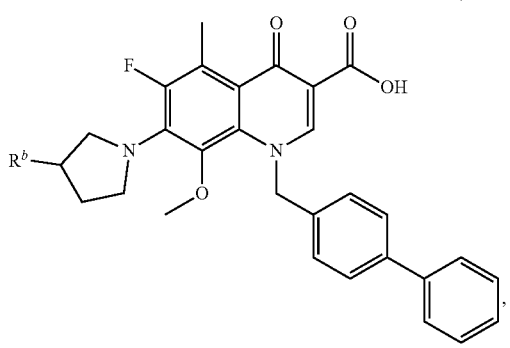
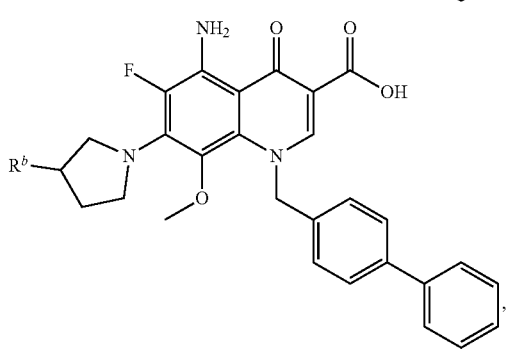
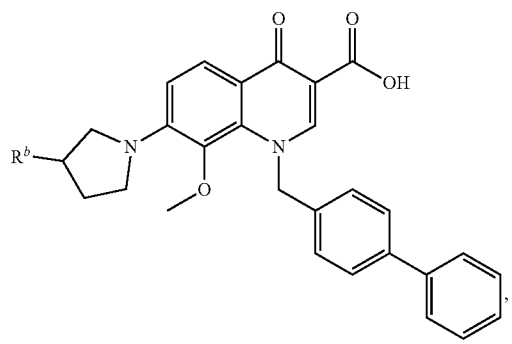
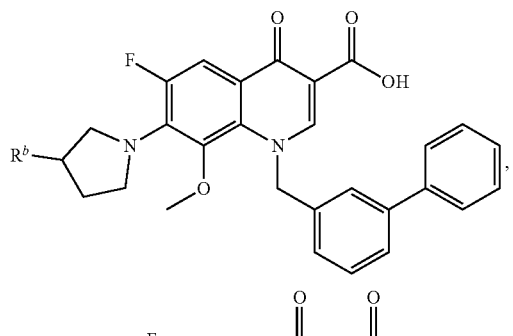
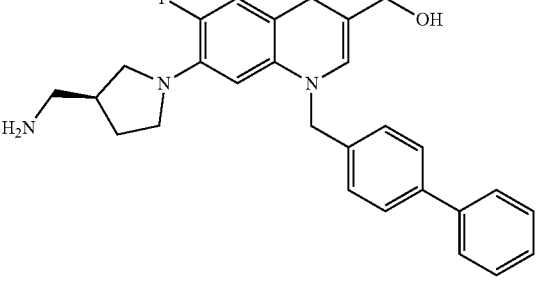
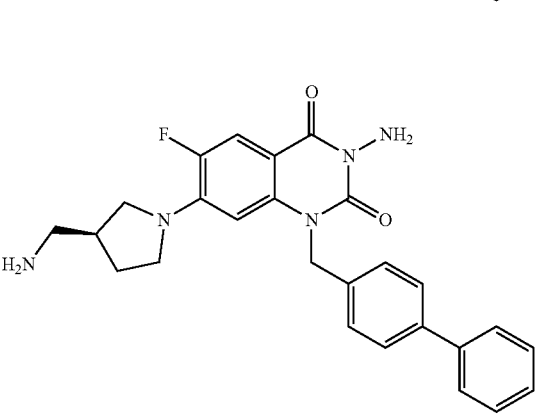
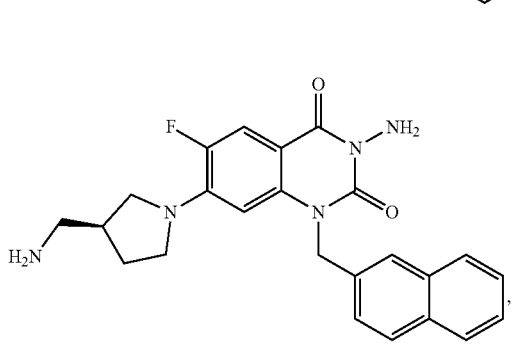

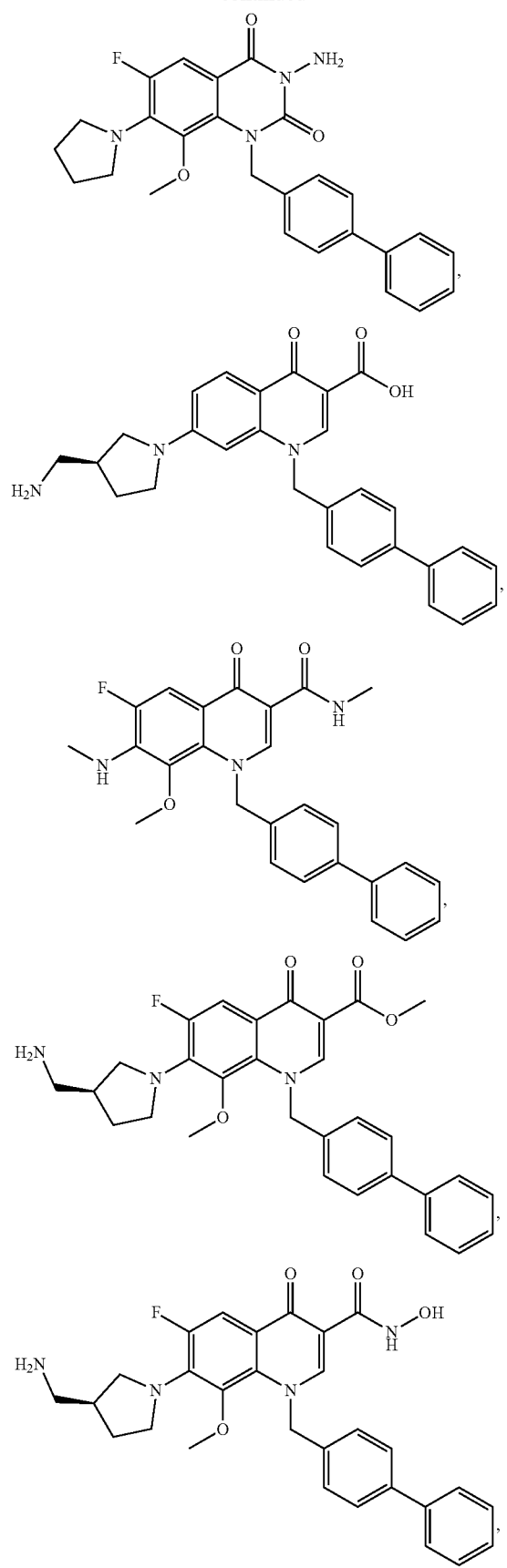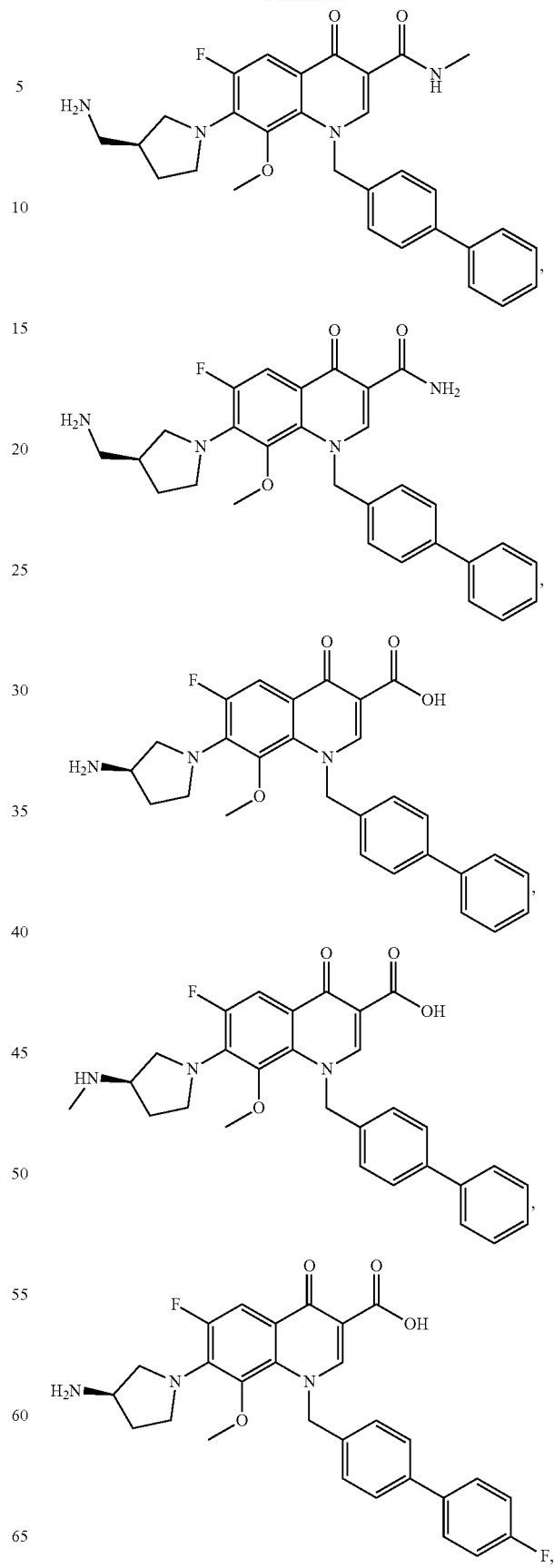

97
-continued
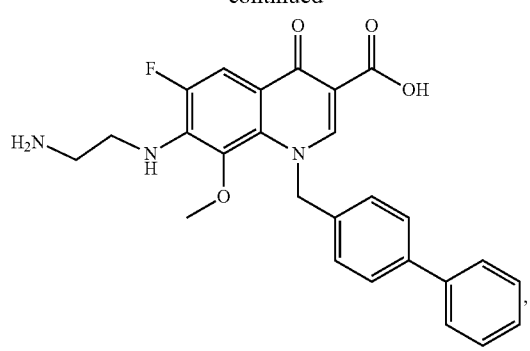
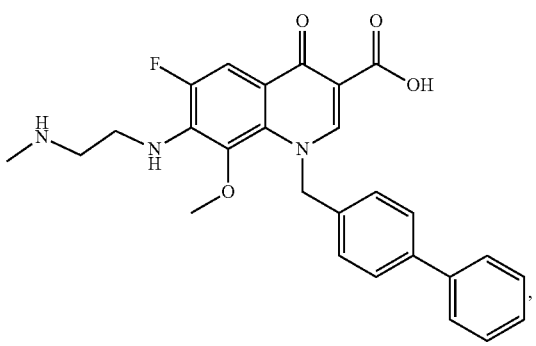
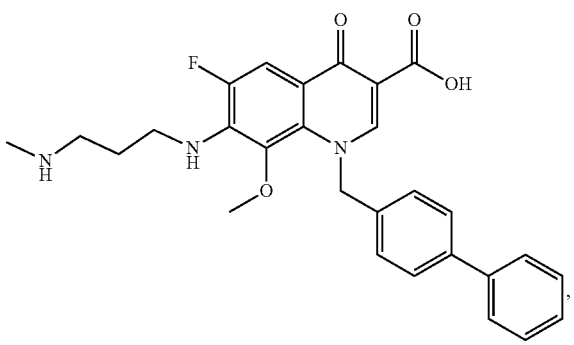
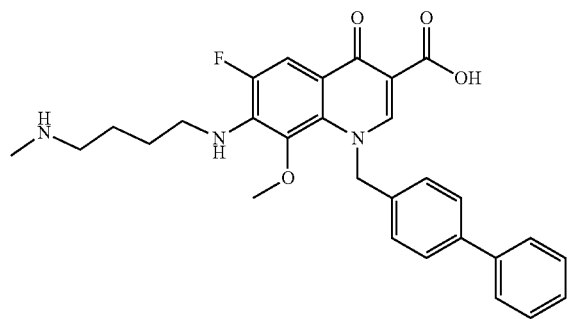
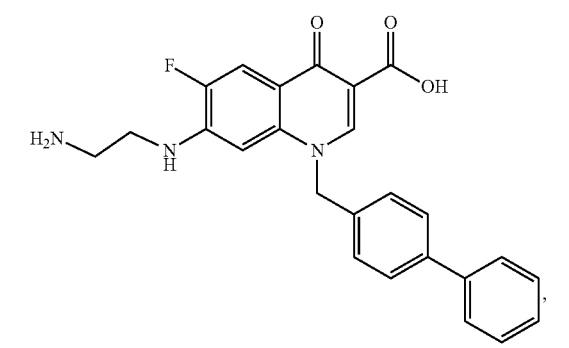
98
-continued
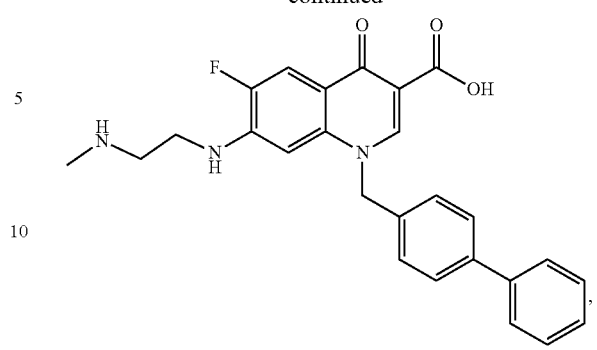
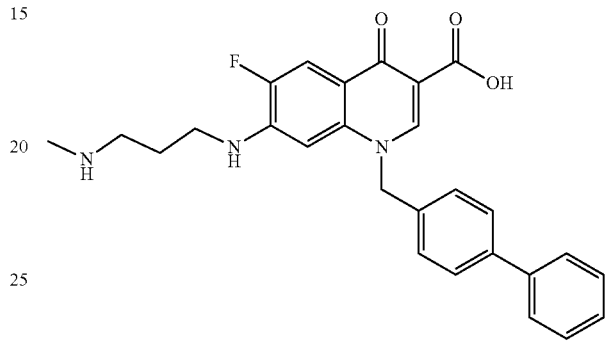
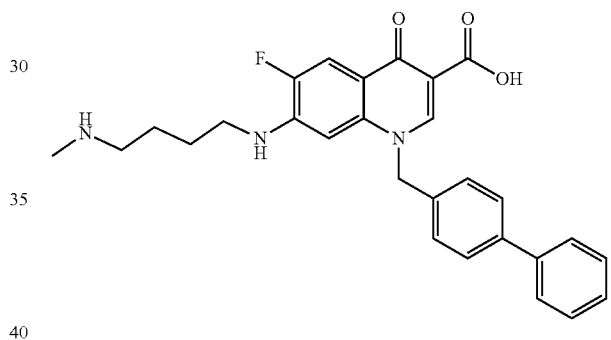
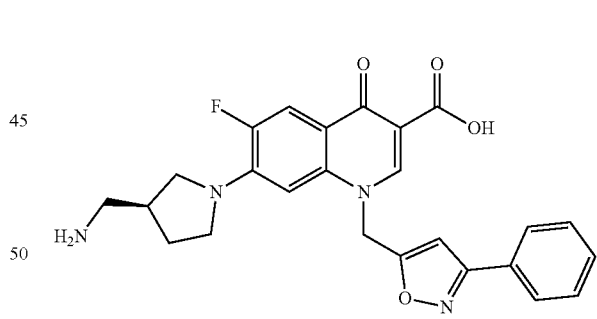
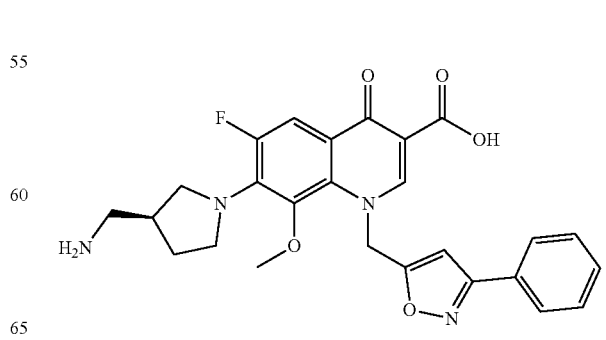

99
-continued
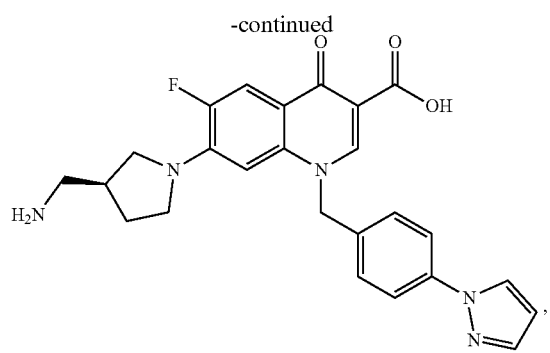
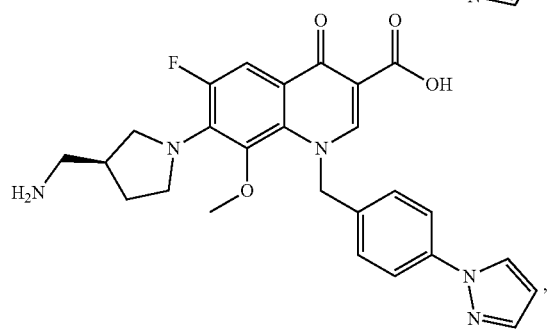
100
-continued
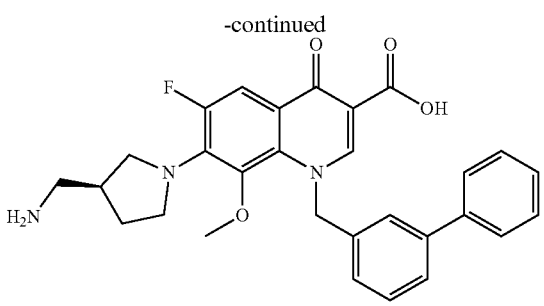
or
a pharmaceutically acceptable salt, polymorph, prodrug, solvate or clathrate thereof.
* * * * *